United States Patent [19]
Lindquist

[11] Patent Number: 5,827,685
[45] Date of Patent: Oct. 27, 1998

[54] METHODS AND COMPOSITIONS OF GENETIC STRESS RESPONSE SYSTEMS

[75] Inventor: Susan Lindquist, Chicago, Ill.

[73] Assignee: Arch Development Corporation, Chicago, Ill.

[21] Appl. No.: 249,380

[22] Filed: May 25, 1994

Related U.S. Application Data

[63] Continuation of Ser. No. 710,187, Jun. 3, 1991, abandoned.

[51] Int. Cl.$^6$ .............................. C12N 15/31; C12N 1/16; C12N 15/63; C07K 14/395
[52] U.S. Cl. .................... 435/69.1; 435/71.1; 435/172.1; 435/172.3; 435/252.3; 435/252.33; 435/255.1; 435/255.2; 435/320.1; 536/23.1; 536/23.74; 536/24.3; 424/139.1; 530/350; 530/387.9; 514/2
[58] Field of Search ................................. 435/69.1, 71.1, 435/172.3, 172.1, 252.3, 252.33, 255.1, 255.2, 320.1; 536/23.74, 24.3, 23.1; 424/139.1; 530/350, 387.9; 514/2

[56] References Cited

U.S. PATENT DOCUMENTS 5,348,945  9/1994  Berberian et al. ..................... 514/21

FOREIGN PATENT DOCUMENTS

WO 90/04604  5/1990  WIPO .

OTHER PUBLICATIONS

Parsell et al., "Hsp104 is a highly conserved protein with two essential nucleotide–binding sites," *Nature*, 353:270–273, 1991.
Sanchez et al., "Yeast HSP104 is required for induced thermotolerance," Thirtieth Annual Meeting of The American Society for Cell Biology, San Diego, California, Abstract # 2822, 1990.
Squires et al., "ClpB is the *Escherichia coli* Heat Shock Protein F84.1," *Journal of Bacteriology*, 173(14):4254–4262, 1991.
Supplemental European Search Report, dated Sep. 16, 1994.
Sanchez & Lindquist, Science, 248:1112–1115, 1990.
Gottesman et al., J. Biol. Chem., 265(14):7886–7893, 1990.
Gottesman et al., PNAS, 87:3513–3517, 1990.
Petersen & Lindquist, Gene, 72(1–2), 161–168, 1988.
Katayama et al., J. Biol. Chem., 263(29):15226–15236, 1988.
Fry et al., PNAS, 83:907–911, 1986.
Shyy et al., Cancer Res., 46:4738–4745, 1986.
Welch et al., J. Cell. Biol., 103:2035–2052, 1986.
Lindquist, Ann. Rev. Biochem., 55:1151–1191, 1986.
Walker et al., J. Mol. Biol., 184:677–701, 1985.
Subjeck et al., J. Cell. Biol., 97:1389–1395, 1983.
Rothstein, Methods in Enzymology, 101:202–211, 1983.
Dialog search report.
S. Raina et al. "A New *Escherichia coli* Heat Shock Gene. htrc, . . . " J. Bacteriol. 172(6) 3417–3426 (Jun. 1990).
W.P. Sheffield et al. "Mitochondnal Precursor Protein" J. Biol. Chem. 265(19) 11069–11076 (Jul. 1990).
K.A. Borkovich et al. "hsp 82 is an Essential Protein that is Required in . . . " Mol. Cell. Biol. 9(9) 3919–3930 (Sep. 1989).
E.A. Craig et al. "Mutations of the Heat Inducible To Kilodolhn" all 38:841–849 (Oct. 1984).

*Primary Examiner*—Rebecca E. Prouty

[57] ABSTRACT

This invention relates to the identification, isolation, purification and manipulation of genetic stress response systems, and more particularly, to genes and expression products of those genes that are components of those systems. These components may be used to protect against potentially toxic stress factors. Stress factors include heat, alcohol and heavy metal ions. A family of stress protector proteins with apparent molecular weights about 100 kd, the hsp100 proteins, are an aspect of this invention. Other stress protector proteins are also within the scope of this invention to enhance or inhibit biological stress response. Applications of this invention to recombinant DNA technology, to commercial methods of food preparation and processing, and to methods of enhancing the stress response of plants and animals, are presented.

33 Claims, 27 Drawing Sheets

ATTGCCAGAGATTCTGCTTTGGATTTAGTTGATATTTCTTGTGCTGGTGTCGCCGTCGCAAGAGATTCTAAGCCAGAAGAATTGGATTCCAA
 L   P   D   S   A   L   D   L   V   D   I   S   C   A   G   V   A   V   A   R   D   S   K   P   E   E   L   D   S   K
GGAACAGTCAATTGCAATTGATTCAAGTAGAGATAAAAGCTCCACACTAAAAGAAAGTAAAGTT
 E   Q   S   I   A   I   D   S   S   R   D   K   S   S   R   E   V   E   C   R   L   H   T   K   R   K   L   K   L
AGCTAGAACAGAAGGAAGCTTCATTGCAAGAAGAATTGGAACCTCTAAGACAACGTTACAATGAAGAAAAGCATGGCCATGAAGAATTGAC
 A   R   Q   K   E   A   S   L   Q   E   E   L   E   P   L   R   Q   R   Y   N   E   E   K   H   G   H   E   E   L   T
ACAAGCTAAAAAGAAATTGGATGAACTGGAAAACAAGGCCCTTGTAGCTGAACGTAGATATGATACTCGTACCGCCTGATTTAAGGTA
 Q   A   K   K   L   D   E   L   E   N   K   A   L   V   A   E   R   R   Y   D   T   R   T   A   D   L   R   Y
CTTCGCCATCCCAGATATCAAAAAGCAAATCGAAAAGCTTGAAGATCAGGTTGCTGAGGAAGAGACGTGCTGGTGCCAACTCCATGAT
 Q   A   K   K   L   D   E   L   E   N   K   A   L   V   A   E   R   R   A   G   A   N   S   M   I
CCAAAATGTGTCAGACAATATCAGACACCATTTCTGACTATCATCTGAAGTGGGGCCAAATGGATGCCATTAAAGCTGTTCCAATGCCGTTAGATTGTC
 F   A   I   P   D   I   K   K   Q   I   E   K   L   E   D   Q   V   A   E   E   E   R   R   A   G   A   N   S   M   I
AAAAATTGATTCATATGGAACGTGATCTGAGTGAAGTTGTCGGTCAGATGGACGCAATTAAAGCTGTGTCCAATGCCGTTAGATTGTC
 Q   N   V   D   S   D   T   I   S   E   T   A   A   R   L   T   G   I   P   V   K   K   L   S   E   S   E   N   E
TAGATCAGGTTAGCTAATCAGGCAACATCCTTCTATTTTAGGTTCTGAATTGTTCGATTGTCTGAATTAAGCGAGAAGTATGCGGTCTCTAAGTGTTGGG
 K   L   I   H   M   E   R   D   L   S   S   E   V   V   G   Q   M   D   A   I   K   A   V   S   N   A   V   R   L   S
TGCTGGATTTTTGTTAATGATGAGGACATGATGATCAGGGTCGATTGTTCTGAATTAAGCGAGAAGTATGCGGTCTCTAAGTGTTGGG
 R   S   G   L   A   N   P   R   Q   P   A   S   F   L   F   G   L   S   G   S   G   K   T   E   L   A   K   K   V
TACCACGGCAGGTTATGTCGGGTACGATGAAGGTGGCTTTTTAACTAACAACTGCAATACAAACCATACTCCGTTTGTATTCGATGA
 A   G   F   L   F   N   D   E   D   M   M   I   R   V   D   C   S   E   L   S   E   K   Y   A   V   S   K   L   L   G
AGTAGAAAAGGCACATCCTGATGTTTTGACTGTCATGTGCTACAAATGTTGGATGATGGTCGAATTACTTCTGGTCAAGGTAAGACGATCGA
 T   A   G   Y   V   G   Y   D   E   G   G   F   L   T   N   Q   L   Q   Y   K   P   Y   S   V   L   L   F   D   E
 V   E   K   A   H   P   D   V   L   T   V   M   L   Q   M   L   D   D   G   R   I   T   S   G   Q   G   K   T   I   D

MNDQTQFTERALTILTLAQKLASDHQHPQLQPIHILAAFIETPEDGSVPYLQNLIEKGRYDYDLF

KKVVNRNLVRIPQQQPAPAEITPSYALGKVLQDAAKIQKQQKDSFIAQDHILFALFNDSSIQQIF  130

KEAQVDIEAIKQQALELRGNTRIDSRGADTNTPLEYLSKYAIDMTEQARQGKLDPVIGREEEIRS

TIRVLARRIKSNPCLIGEPGIGKTAIIEGVAQRIIDDDVPIILQGAKLFSLDLAALTAGAKYKGD  260

FEERFKGVLKEIEESKTLIVLFIDEIHMLMGNGKDDAANILKPALSRGQLKVIGATTNNEYRSIV

EKDGAFERRFQKIEVAEPSVRQTVAILRGLQPKYEIHHGVRILDSALVTAAQLAKRYLPYRRLPD  390

SALDLVDISCAGVAVARDSKPEELDSKEQSIAIDSSRDKSSRERVECRLHTKRKLKLARQKEASL

QEELEPLRQRYNEEKHGHEELTQAKKKLDELENKALVAERRYDTRTAADLRYFAIPDIKKQIEKL  520

EDQVAEEERRAGANSMIQNVVDSDTISETAARLTGIPVKKLSESENEKLIHMERDLSSEVVGQMD

AIKAVSNAVRLSRSGLANPRQPASFLFLGLSGSGKTELAKKVAGFLFNDEDMMIRVDCSELSEKY  650

AVSKLLGTTAGYVGYDEGGFLTNQLQYKPYSVLLFDEVEKAHPDVLTVMLQMLDDGRITSGQGKT

IDCSNCIVIMTSNLGAEFINSQQGSKIQESTKNLVMGAVRQHFRPEFLNRISSIVIFNKLSRKAI  780

HKIVDIRLKEIEERFEQNDKHYKLNLTQEAKDFLAKYGYSDDMGARPLNRLIQNEILNKLALRIL

KNEIKDKETVNVVLKKGKSRDENVPEEAEECLEVLPNHEATIGADTLGDDDNEDSMEIDDDLD  908

FIG. 1E

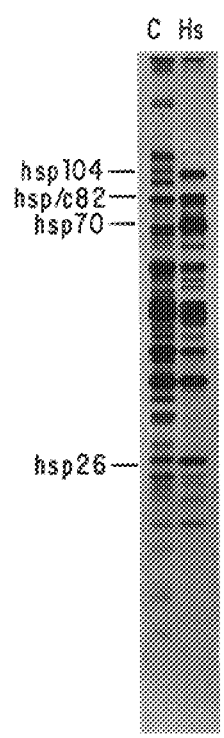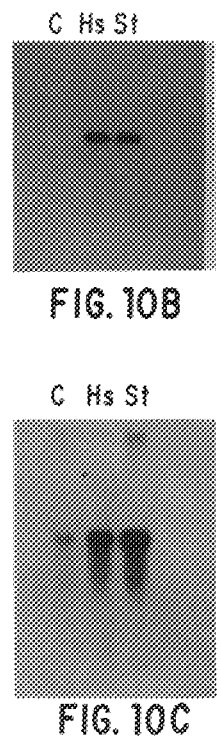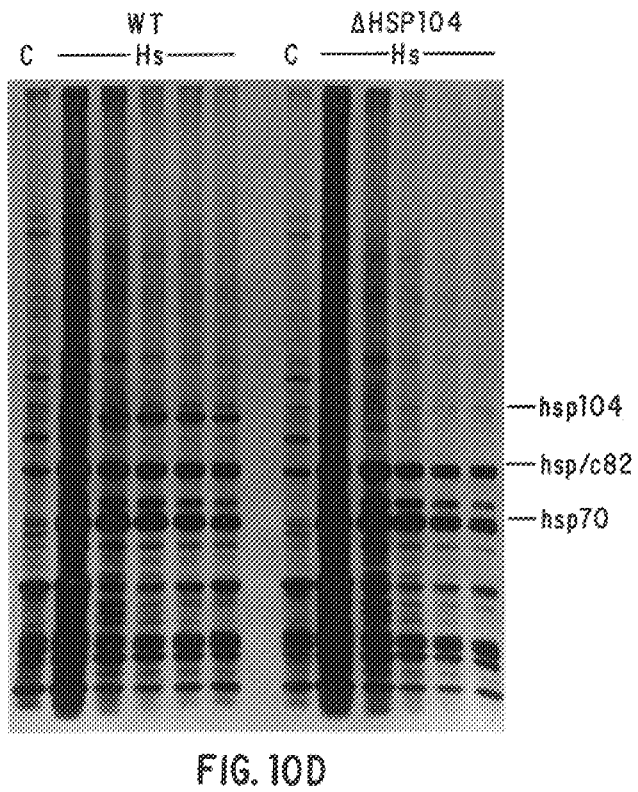
FIG. 10A  FIG. 10B  FIG. 10C  FIG. 10D

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 3727 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:1:

```
TTTCCAATCA  GAGCAAGAGT  AGCAAGGCTT  CTAAAAGCCC  GAAGTGGTCG  AGCTACGCAT      60

TCCCTTCGCG  TGAGACCATC  AAATCTCATG  AGGAGGCCAT  CAAGAAGCAG  AATAAAGCTA     120

TAGACGAGCA  AATAGCTGCT  GCAGTATCCA  AGAATGACTG  CTCTTGCACA  GAACCTCCCA     180

AGAAAAGAAA  GAGGAAATTG  AGACCAAGAA  AGGCGCTGAT  CACCCTGAGT  CCGAAGGCAA     240

TCAAGCATTT  AAGGGCACTG  CTAGCTCAGC  CGGAACCTAA  ATTGATTAGA  GTTAGCGCTA     300
```

```
GAAACCGTGG ATGTTCAGGA CTAACGTACG ATCTACAATA TATGACCGAG CCGGGGAAAT      360
TCGATGAGGT AGTAGAACAA GATGGCGTTA AAATTGTCAT CGATTCAAAG GCGTTATTCA      420
GCATCATTGG AAGTGAAATG GACTGGGTCG ACGACAAGTT GGCCTCTAAG TTTGTCTTCA      480
AGAATCCAAA CTCCAAGGGC ACATGCGGTT GTGGCGAGAG TTTCATGGTT TAAAAACCTT      540
CTGCACCATT TTTAGAAAAA AAGAATCTAC CTATTCACTT ATTTATTCAT TTACTTATTT      600
ATTTACATAT TTATCATACA TATTAACATT GAACCCTCCA TCGTGGTAGT GTTTGCTGTT      660
CCTAACTTTT CTTTCGTTGT TCTTGTAGAT ATATATTTTT CCAGAATTTT CTAGAAGGGT      720
TATTAATTAC AATCTTAAAC GTTCCATAAG GGGCCGCGAT TTTTTGTTC AATTTTCAAC      780
AGGGGGCCCA TCTCAAAGAA CTGCAAATTA TATCACAGTA AAAGGCAAAG GGGCGCAAAC      840
TTATGCAACC TGCCAGATTA TTATATAAGG CATTGTAATC TTGCCTCAAT TCCTTCATAA      900
TTCGTTCCTT TGTCACTTGT TCCTTTTTAC CCTTGAATCG AATCAGCAAT AACAAAGAAA      960
AAGAAATCA ACTACACGTA CCATAAAATA TACAGAATAT ATGAACGACC AAACGCAATT     1020
TACAGAAGG GCTCTAACGA TTTTGACGTT GGCTCAAAAA TTGGCTTCGG ATCATCAACA     1080
TCCACAATTA CAACCTATAC ATATTCTAGC TGCCTTCATT GAAACGCCAG AAGATGGATC     1140
AGTCCCTTAC CTACAGAATC TAATTGAGAA GGGCCGTTAC GACTATGATC TTTTCAAGAA     1200
AGTGGTTAAT AGAAATCTAG TAAGAATTCC TCAACAGCAA CCTGCACCTG CGGAGATAAC     1260
TCCAAGTTAT GCTTTGGGGA AAGTCCTTCA AGACGCTGCT AAGATTCAAA AACAACAGAA     1320
GGACTCATTT ATAGCGCAAG ACCATATATT GTTTGCTCTA TTCAATGATT CGTCTATTCA     1380
GCAAATATTT AAGGAAGCTC AAGTAGATAT TGAGGCCATC AAGCAACAAG CTCTTGAACT     1440
TCGTGGTAAC ACTAGAATTG ACTCTCGTGG CGCTGATACG AACACACCTT TGGAATATTT     1500
ATCAAAGTAC GCCATTGATA TGACTGAGCA GGCTCGTCAA GGTAAACTTG ACCCTGTCAT     1560
CGGCCGTGAA GAAGAAATAA GAAGCACTAT TAGAGTTTTA GCAAGAAGAA TTAAGTCCAA     1620
CCCATGTTTA ATTGGTGAGC CAGGTATCGG TAAGACCGCT ATTATTGAAG GTGTTGCTCA     1680
AAGAATCATT GACGATGACG TTCCCATTAT CTTACAAGGC GCTAAATTGT TCAGTCTAGA     1740
TTTGGCCGCA TTAACCGCAG GTGCTAAATA CAAGGTGAT TTCGAAGAAA GATTCAAAGG     1800
TGTTTTGAAG GAAATCGAAG AATCAAAGAC TCTAATTGTG TTATTCATTG ATGAAATTCA     1860
CATGTTAATG GGTAATGGTA AGGACGACGC TGCTAACATC TTGAAGCCAG CTTTGTCCAG     1920
AGGCCAATTG AAGGTCATCG GTGCCACCAC CAATAACGAA TATAGATCTA TTGTGGAAAA     1980
GGATGGTGCC TTTGAAAGAA GATTCCAGAA AATTGAAGTC GCTGAACCAA GTGTGAGACA     2040
AACAGTGGCC ATATTGAGAG GTCTGCAACC AAAGTATGAA ATACATCATG GTGTAAGGAT     2100
TCTGGATAGC GCCTTAGTCA CTGCTGCTCA ATTAGCCAAG CGTTACTTGC CATATAGAAG     2160
ATTGCCAGAT TCTGCTTTGG ATTTAGTTGA TATTTCTTGT GCTGGTGTCG CCGTCGCAAG     2220
AGATTCTAAG CCAGAAGAAT TGGATTCCAA GGAACAGTCA ATTGCAATTG ATTCAAGTAG     2280
AGATAAAAGC TCTAGAGAGA GAGTAGAGTG CCGACTCCAC ACTAAAAGAA AGTTAAAGTT     2340
AGCTAGACAG AAGGAAGCTT CATTGCAAGA AGAATTGGAA CCTCTAAGAC AACGTTACAA     2400
TGAAGAAAAG CATGGCCATG AAGAATTGAC ACAAGCTAAA AAGAAATTGG ATGAACTGGA     2460
AAACAAGGCC CTTGTAGCTG AACGTAGATA TGATACTCGT ACCGCCGCTG ATTTAAGGTA     2520
CTTCGCCATC CCAGATATCA AAAAGCAAAT CGAAAAGCTT GAAGATCAGG TTGCTGAGGA     2580
AGAGAGACGT GCTGGTGCCA ACTCCATGAT CCAAAATGTG GTCGATTCAG ACACCATTTC     2640
TGAAACAGCT GCAAGATTGA CTGGTATCCC TGTTAAGAAG TTGTCAGAAT CTGAAAATGA     2700
```

| | | | | | | |
|---|---|---|---|---|---|---|
| AAAATTGATT | CATATGGAAC | GTGACTTATC | ATCTGAAGTC | GTGGGCCAAA | TGGATGCCAT | 2760 |
| TAAAGCTGTT | TCCAATGCCG | TTAGATTGTC | TAGATCAGGT | TTAGCTAATC | CAAGGCAACC | 2820 |
| AGCATCCTTC | TTATTTTTAG | GTTTGTCCGG | TTCCGGTAAA | ACTGAATTGG | CTAAAAAAGT | 2880 |
| TGCTGGATTT | TTGTTTAATG | ATGAGGACAT | GATGATCAGG | GTCGATTGTT | CTGAATTAAG | 2940 |
| CGAGAAGTAT | GCGGTCTCTA | AGTTGTTGGG | TACCACGGCA | GGTTATGTCG | GGTACGATGA | 3000 |
| AGGTGGCTTT | TTAACTAACC | AACTGCAATA | CAAACCATAC | TCCGTTTTGT | TATTCGATGA | 3060 |
| AGTAGAAAAG | GCACATCCTG | ATGTTTTGAC | TGTCATGCTA | CAAATGTTGG | ATGACGGTAG | 3120 |
| AATTACTTCT | GGTCAAGGTA | AGACGATCGA | CTGTTCCAAT | TGTATTGTCA | TCATGACTTC | 3180 |
| CAATCTAGGT | GCTGAATTTA | TCAATTCTCA | ACAAGGATCA | AAGATCCAAG | AATCTACCAA | 3240 |
| GAATTTGGTC | ATGGGTGCTG | TTAGGCAACA | TTTCAGACCA | GAATTTTTGA | ACAGAATTTC | 3300 |
| TAGTATAGTC | ATTTTCAACA | AGCTATCTAG | AAAAGCTATT | CATAAGATCG | TGGATATTCG | 3360 |
| TTTGAAGGAA | ATTGAAGAGA | GATTCGAGCA | AAATGATAAA | CATTACAAGT | TGAATTTAAC | 3420 |
| TCAAGAGGCC | AAGGACTTCT | TGGCCAAATA | TGGTTATTCC | GATGATATGG | GTGCACGTCC | 3480 |
| ACTGAACAGG | TTAATTCAAA | ACGAAATTTT | GAACAAACTG | GCACTAAGGA | TCTTAAAGAA | 3540 |
| TGAAATCAAG | GATAAGGAAA | CTGTCAATGT | CGTCTTGAAG | AAGGGTAAAT | CTCGTGATGA | 3600 |
| AAATGTTCCT | GAGGAAGCTG | AAGAATGTCT | GGAAGTTCTA | CCAAATCACG | AAGCTACTAT | 3660 |
| AGGGGCTGAC | ACGTTAGGTG | ATGACGATAA | TGAGGACAGT | ATGGAAATTG | ATGATGACCT | 3720 |
| AGATTAA | | | | | | 3727 |

( 2 ) INFORMATION FOR SEQ ID NO:2:

( i ) SEQUENCE CHARACTERISTICS:
        ( A ) LENGTH: 908 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:2:

```
Met Asn Asp Gln Thr Gln Phe Thr Glu Arg Ala Leu Thr Ile Leu Thr
  1               5                  10                  15

Leu Ala Gln Lys Leu Ala Ser Asp His Gln His Pro Gln Leu Gln Pro
                 20                  25                  30

Ile His Ile Leu Ala Ala Phe Ile Glu Thr Pro Glu Asp Gly Ser Val
             35                  40                  45

Pro Tyr Leu Gln Asn Leu Ile Glu Lys Gly Arg Tyr Asp Tyr Asp Leu
         50                  55                  60

Phe Lys Lys Val Val Asn Arg Asn Leu Val Arg Ile Pro Gln Gln Gln
 65                  70                  75                  80

Pro Ala Pro Ala Glu Ile Thr Pro Ser Tyr Ala Leu Gly Lys Val Leu
                 85                  90                  95

Gln Asp Ala Ala Lys Ile Gln Lys Gln Gln Lys Asp Ser Phe Ile Ala
                100                 105                 110

Gln Asp His Ile Leu Phe Ala Leu Phe Asn Asp Ser Ser Ile Gln Gln
             115                 120                 125

Ile Phe Lys Glu Ala Gln Val Asp Ile Glu Ala Ile Lys Gln Gln Ala
         130                 135                 140

Leu Glu Leu Arg Gly Asn Thr Arg Ile Asp Ser Arg Gly Ala Asp Thr
145                 150                 155                 160
```

```
Asn Thr Pro Leu Glu Tyr Leu Ser Lys Tyr Ala Ile Asp Met Thr Glu
            165                 170                 175
Gln Ala Arg Gln Gly Lys Leu Asp Pro Val Ile Gly Arg Glu Glu Glu
            180                 185                 190
Ile Arg Ser Thr Ile Arg Val Leu Ala Arg Arg Ile Lys Ser Asn Pro
            195                 200                 205
Cys Leu Ile Gly Glu Pro Gly Ile Gly Lys Thr Ala Ile Ile Glu Gly
            210                 215                 220
Val Ala Gln Arg Ile Ile Asp Asp Asp Val Pro Ile Ile Leu Gln Gly
225                     230                 235                 240
Ala Lys Leu Phe Ser Leu Asp Leu Ala Ala Leu Thr Ala Gly Ala Lys
                245                 250                 255
Tyr Lys Gly Asp Phe Glu Glu Arg Phe Lys Gly Val Leu Lys Glu Ile
            260                 265                 270
Glu Glu Ser Lys Thr Leu Ile Val Leu Phe Ile Asp Glu Ile His Met
            275                 280                 285
Leu Met Gly Asn Gly Lys Asp Asp Ala Ala Asn Ile Leu Lys Pro Ala
    290                 295                 300
Leu Ser Arg Gly Gln Leu Lys Val Ile Gly Ala Thr Thr Asn Asn Glu
305                     310                 315                 320
Tyr Arg Ser Ile Val Glu Lys Asp Gly Ala Phe Glu Arg Arg Phe Gln
                325                 330                 335
Lys Ile Glu Val Ala Glu Pro Ser Val Arg Gln Thr Val Ala Ile Leu
            340                 345                 350
Arg Gly Leu Gln Pro Lys Tyr Glu Ile His His Gly Val Arg Ile Leu
            355                 360                 365
Asp Ser Ala Leu Val Thr Ala Ala Gln Leu Ala Lys Arg Tyr Leu Pro
    370                 375                 380
Tyr Arg Arg Leu Pro Asp Ser Ala Leu Asp Leu Val Asp Ile Ser Cys
385                     390                 395                 400
Ala Gly Val Ala Val Ala Arg Asp Ser Lys Pro Glu Glu Leu Asp Ser
                405                 410                 415
Lys Glu Gln Ser Ile Ala Ile Asp Ser Arg Asp Lys Ser Ser Arg
            420                 425                 430
Glu Arg Val Glu Cys Arg Leu His Thr Lys Arg Lys Leu Lys Leu Ala
            435                 440                 445
Arg Gln Lys Glu Ala Ser Leu Gln Glu Glu Leu Glu Pro Leu Arg Gln
    450                 455                 460
Arg Tyr Asn Glu Glu Lys His Gly His Glu Glu Leu Thr Gln Ala Lys
465                     470                 475                 480
Lys Lys Leu Asp Glu Leu Glu Asn Lys Ala Leu Val Ala Glu Arg Arg
                485                 490                 495
Tyr Asp Thr Arg Thr Ala Ala Asp Leu Arg Tyr Phe Ala Ile Pro Asp
            500                 505                 510
Ile Lys Lys Gln Ile Glu Lys Leu Glu Asp Gln Val Ala Glu Glu Glu
            515                 520                 525
Arg Arg Ala Gly Ala Asn Ser Met Ile Gln Asn Val Asp Ser Asp
    530                 535                 540
Thr Ile Ser Glu Thr Ala Ala Arg Leu Thr Gly Ile Pro Val Lys Lys
545                     550                 555                 560
Leu Ser Glu Ser Glu Asn Glu Lys Leu Ile His Met Glu Arg Asp Leu
                565                 570                 575
Ser Ser Glu Val Val Gly Gln Met Asp Ala Ile Lys Ala Val Ser Asn
            580                 585                 590
```

|     |     |     |     |     |     |     |     |     |     |     |     |     |     |     |
|-----|-----|-----|-----|-----|-----|-----|-----|-----|-----|-----|-----|-----|-----|-----|
| Ala | Val | Arg 595 | Leu | Ser | Arg | Ser | Gly 600 | Leu | Ala | Asn | Pro | Arg 605 | Gln | Pro | Ala |
| Ser | Phe 610 | Leu | Phe | Leu | Gly | Leu 615 | Ser | Gly | Ser | Gly | Lys 620 | Thr | Glu | Leu | Ala |
| Lys 625 | Lys | Val | Ala | Gly | Phe 630 | Leu | Phe | Asn | Asp | Glu 635 | Asp | Met | Met | Ile | Arg 640 |
| Val | Asp | Cys | Ser | Glu 645 | Leu | Ser | Glu | Lys | Tyr 650 | Ala | Val | Ser | Lys | Leu 655 | Leu |
| Gly | Thr | Thr | Ala 660 | Gly | Tyr | Val | Gly | Tyr 665 | Asp | Glu | Gly | Gly | Phe 670 | Leu | Thr |
| Asn | Gln | Leu 675 | Gln | Tyr | Lys | Pro | Tyr 680 | Ser | Val | Leu | Leu | Phe 685 | Asp | Glu | Val |
| Glu | Lys 690 | Ala | His | Pro | Asp | Val 695 | Leu | Thr | Val | Met | Leu 700 | Gln | Met | Leu | Asp |
| Asp 705 | Gly | Arg | Ile | Thr | Ser 710 | Gly | Gln | Gly | Lys | Thr 715 | Ile | Asp | Cys | Ser | Asn 720 |
| Cys | Ile | Val | Ile | Met 725 | Thr | Ser | Asn | Leu | Gly 730 | Ala | Glu | Phe | Ile | Asn 735 | Ser |
| Gln | Gln | Gly | Ser 740 | Lys | Ile | Gln | Glu | Ser 745 | Thr | Lys | Asn | Leu | Val 750 | Met | Gly |
| Ala | Val | Arg 755 | Gln | His | Phe | Arg | Pro 760 | Glu | Phe | Leu | Asn | Arg 765 | Ile | Ser | Ser |
| Ile | Val 770 | Ile | Phe | Asn | Lys | Leu 775 | Ser | Arg | Lys | Ala | Ile 780 | His | Lys | Ile | Val |
| Asp 785 | Ile | Arg | Leu | Lys | Glu 790 | Ile | Glu | Glu | Arg | Phe 795 | Glu | Gln | Asn | Asp | Lys 800 |
| His | Tyr | Lys | Leu | Asn 805 | Leu | Thr | Gln | Glu | Ala 810 | Lys | Asp | Phe | Leu | Ala 815 | Lys |
| Tyr | Gly | Tyr | Ser 820 | Asp | Asp | Met | Gly | Ala 825 | Arg | Pro | Leu | Asn | Arg 830 | Leu | Ile |
| Gln | Asn | Glu 835 | Ile | Leu | Asn | Lys | Leu 840 | Ala | Leu | Arg | Ile | Leu 845 | Lys | Asn | Glu |
| Ile | Lys 850 | Asp | Lys | Glu | Thr | Val 855 | Asn | Val | Val | Leu | Lys 860 | Lys | Gly | Lys | Ser |
| Arg 865 | Asp | Glu | Asn | Val | Pro 870 | Glu | Glu | Ala | Glu | Glu 875 | Cys | Leu | Glu | Val | Leu 880 |
| Pro | Asn | His | Glu | Ala 885 | Thr | Ile | Gly | Ala | Asp 890 | Thr | Leu | Gly | Asp | Asp 895 | Asp |
| Asn | Glu | Asp | Ser 900 | Met | Glu | Ile | Asp | Asp 905 | Asp | Leu | Asp |

METHODS AND COMPOSITIONS OF GENETIC STRESS RESPONSE SYSTEMS This application is a continuation of application Ser. No. 07/710,187, filed Jun. 3, 1991 now abandoned.

The government may own certain rights to the present invention pursuant to NIH grant #5-R01 GM 35482.

BACKGROUND OF THE INVENTION

1. Field of the Invention

This invention relates to the isolation, purification and manipulation of genetic stress response systems, and more particularly, to genes that are components of those systems and to expression products and promoters of those genes. This invention also relates to methods to protect organisms against potentially toxic stress factors, and conversely, methods to harm organisms by tampering with their stress response systems, so that they cannot protect themselves against potentially toxic stress factors. Applications of this invention to recombinant DNA technology, to commercial methods of food preparation and processing, and to methods of enhancing the stress response of plants and animals, are presented.

2. Description of Related Art

Genetic systems which permit organisms to respond defensively to stress have been inferred from empiric observations. One of the major stresses which triggers a response from intact organisms, tissues or cultured cells, is temperature, both extreme heat and extreme cold. In this context "extreme" means temperature ranges that are undesirable for normal physiological functioning and/or survival of a particular genus and species. There appears to be an almost universal response of organisms to heat shock, that response being to produce a small number of proteins. When cells are exposed to mildly elevated temperatures, they respond by producing a small number of proteins called the heat-shock proteins, or hsps (See review by Lindquist, 1986, for a general treatment of the heat shock response and the review by Lindquist and Craig, 1988, for a detailed description of what is known about the functions of the heat shock proteins; Hemmingsen et al., 1988; Deshaies et al., 1988; Chirico et al., 1988; Kang et al., 1990; Cheng et al., 1989; Reading et al., 1989; Borkovich et al., 1989; Picard et al., 1990; Rothman et al., 1989.) This response is the most highly conserved genetic regulatory system known. In both eukaryotic and prokaryotic organisms, heat shock genes have been localized and found to be scattered among various chromosomal locations.

The heat-shock response was first discovered in the fruit fly, *Drosophila melanogaster*. Since then, it has been found in virtually all organisms, including bacteria, plants, warm and cold blooded vertebrates, protozoa, insects, sea urchins, slim molds, and fungi. (The single known exception is a few species of Hydra.) In multicellular organisms, the response is observed in virtually every tissue, and at every stage of development. The response can also be induced by a variety of other stress treatments, such as exposure to ethanol, anoxia, and heavy metal ions.

Exposing cells and organisms to mild stress, such as moderately warm temperatures and low concentrations of ethanol, also induces tolerance to more extreme stresses such as higher temperatures and higher concentrations of ethanol. Because of the general correlation between the induction of tolerance and the synthesis of heat shock proteins, for many years it has been postulated that heat shock proteins might play an important role in the acquisition of tolerance. However, the results of several experiments call this into question. For example, it has been reported in several organisms that inhibiting the synthesis of heat shock proteins does not inhibit the induction of tolerance. (See review by Li, 1985 for more detailed discussion.) Genetic tests of the function of the heat shock proteins also suggested the proteins might not be involved in thermotolerance. In particular, several of the genes encoding heat shock proteins have recently been mutated. One of these mutations (in hsp26) has no affect on the ability of a cell to withstand high temperatures (Petko and Lindquist, 1986). Some of these mutations (e.g. mutations in hsp60, hsp70, and hsp82) affect the ability of cells to grow at normal temperatures and at moderately warm temperatures. For example, cells need to make hsp82 in order to live at any temperature, but they need even higher concentrations of the protein to live and grow at higher temperatures (Borkovich et. al., 1989). These mutations either do not affect the ability of an organism to tolerate extreme temperatures or actually increase its ability to survive at extreme temperatures. (For hsp70 mutation effects see Craig and Jacobsen, 1984.)

Mutations in another heat shock gene, ubiquitin, affect the ability of cells to survive chronic exposure to temperatures at the very upper end of their normal growth range, but again, these mutations produced cells which survived extreme temperatures as well as, or better than, the wild-type (Findlay and Varshevsky, 1987). Thus most of the heat shock proteins examined to date play vital roles in the cell at normal temperatures. Additionally, they help to extend the normal temperature growth range of a cell. In addition to being universal, these proteins appear to be highly conserved not only in their protein coding sequences, but also in their regulatory sequences. These findings suggest an evolutionary importance for the role of genes which encode these proteins. Ubiquitin and the hsp proteins may be complementary methods of dealing with a common stress problem, that is, the production of denatured protein aggregates in heat shocked cells.

The heat-shock response of *Drosophila melanogaster*, the organism in which the response was discovered, is the most well characterized among higher eukaryotes. The intensity of the Drosophila response is particularly striking and provides one of the best examples of a reversible, global redirection of macromolecular synthesis (Lewis et al., 1975; Chomyn et al., 1979; DiDomenico et al., 1982). Immediately after a shift from 25° C. (the normal growing temperature of Drosophila tissue culture cells) to 37° C. (a heat-shock inducing temperature) transcription is redirected from the synthesis of normal 25° C. mRNAs to the synthesis of heat-shock mRNAs, the most abundant of which is hsp70 mRNA (Ashburner, 1970; Tissieres et al., 1974; McKenzie et al., 1975; Spradling et al., 1975; McKenzie and Meselson, 1977). At the same time, pre-existing mRNAS are translationally repressed while newly transcribed heat-shock mRNAs are translated at very high rates (Mirault et al., 1978; Lindquist, 1980a; Scott and Purdue, 1981). This translational pattern persists as long as the temperature remains elevated. When the cells are returned to 25° C., heat-shock protein synthesis is repressed and normal protein synthesis is restored (DiDomenico et al., 1982a; Lewis, 1975; Chomyn et al., 1979).

In microorganisms such as the yeast *Saccharomyces cerevisiae* and the bacterium *Escherichia coli*, heat shock proteins are also induced very rapidly after a shift to high temperatures. However, the synthesis of normal cellular proteins is not as severely impaired and during continued exposure to moderately high temperatures (i.e., 37°–40° C.)

growth may resume after heat shock proteins have accumulated. At yet higher temperatures, heat-shock protein synthesis continues until, eventually, cells begin to die.

From these results and subsequent studies on a number of other organisms, it has been suggested that the heat response is transient in most organisms. When organisms are returned to normal temperatures after brief exposure to high temperatures, normal patterns of protein synthesis are restored and growth resumes. When maintained at moderately warm temperatures, growth resumes after a temporary pause. When maintained at higher temperatures, heat shock protein synthesis continues until the cells slowly begin to die. The metabolic state or developmental stage of the cell may affect response.

Examples of Heat Induced Proteins

Previously reported heat shock proteins and other similar proteins appear to play essential roles in growth and metabolism at normal temperature (e.g., hsp70, hsp60, hsp62). Heat shock proteins have been assigned names corresponding to their approximate apparent molecular weight. Hsp70 is the most highly conserved of the hsp proteins. The complete amino acid sequence of hsp70 proteins from various organisms is presented in a review by Lindquist (1986).

Many differences among species are due to homologous substitutions in hsp70. Other differences may represent responses during evolution to the necessity to survive in ecological niches having different temperatures. In addition, in Drosophila, Saccharomyces, and all eukaryotes analyzed, hsp70 genes appear to belong to a multi-gene family whose members respond to temperature in different ways; some members are synthesized at low temperatures and some are targeted to different cellular compartments.

In another size range, all eukaryotic cells studied to date appear to produce a prominent heat-shock protein in the range of 82–90 kd e.g., hsp 82 and 90. Hsp90 has been found to be a major component of several steroid receptor complexes. It also complexes with various oncogenic protein kinases.

Most eukaryotic cells produce proteins in the range of 100 to 110 kD after exposure to high temperatures (Lindquist and Craig, 1988). To date, these proteins have been studied only in mammalian and yeast cells. In mammalian cells, investigations focus on the mammalian 110 kD protein concentrates in the nucleoli of these cells. (Subjeck et al, 1983). Interestingly, the precise staining pattern obtained with anti-hsp 110 antibody is dynamic, changing with growth state, nutritional conditions and heat shock (Subjeck et al, 1983; Shyy, et al, 1986; Welch and Suhan, 1985). Prior to the present invention, the relationships between the mammalian 110 kD protein, the yeast hsp 104 protein, and the high molecular weight heat shock proteins of other organisms were unknown.

There is also a large category of smaller molecular weight hsp proteins which, although varying in size and number in different species, are said to be homologous, i.e. to show identity for certain percentages of their amino acid sequences. For example, in Drosophila, designations for such proteins are hsp22, 23, 27, and 28.

Prokaryotic heat-inducible genes homologous to several eukaryotic heat-shock genes have been reported. Members of the hsp60, hsp70 and hsp90 family were identified in *E. coli* and a member of the small hsp family was identified in mycobacteria. However, until the work pertaining to this invention, there was no evidence that any prokaryotic proteins were homologous to the yeast hsp104 protein.

Tolerance

Mild heat pretreatments are able to effect thermotolerance. If cells are shifted directly to an extreme temperature, lethality is likely. However, at a more moderate elevated temperature, hsp synthesis is induced. If the cells are later exposed to extreme temperatures, there is a dramatic increase in survival compared to the initial lethality response. At stages in development in which hsps cannot be induced, organisms are extremely sensitive to heat and thermotolerance cannot be induced. This phenomenon has been observed in a wide variety of plants, animals, fungi, and bacteria.

These observations suggest that hsps may play a role in thermotolerance. This proposed function, however, has been controversial (Riabawal et al., 1988; McAlister et al., 1980; Li and Laszlo, 1982; Hall, 1983; Widelity et al., 1986; Carper et al., 1987). Mutations in most heat shock protein genes do not compromise thermotolerance. Also, certain inhibitors which block the synthesis of hsps have been reported not to interfere with thermotolerance.

Stresses Other Than Heat

Interestingly, in many organisms such as Drosophila, chirlurus, and yeast, proteins found initially by their induction due to heat shock are similar in structure to those found to be induced by a wide variety of other stresses, for example, alcohol, anoxia, and metals such as cadmium and sodium arsenate. A compilation of the various inducers is provided by Nover (1984), and a summary is presented in Lindquist (1986).

Some of these inductions have only been tested in a small number of organisms and may be unique to particular biological circumstances, but it is clear that others are universal, or nearly universal. Among the most common inducers are ethanol and heavy metal ions. The assumption that these inductions have biological significance rests upon the observation that they are generally associated with increased tolerance, both to the inducing agent itself and to other types of stress. For example, pre-treatments with moderate concentrations of ethanol induce tolerance to yet higher concentrations of ethanol and, at the same time, tolerance to high temperatures. In a complementary fashion, mild heat treatments induce tolerance to both higher temperatures and to high concentrations of ethanol.

This phenomenon is called cross tolerance, and it has been postulated that the heat-shock proteins are responsible for it. Whether individual hsps are of the same relative importance in tolerance to different types of stress was unclear prior to the work described in this invention. Indeed, some investigators have questioned whether hsps play any role at all in tolerance to certain types of stress.

The nucleotide sequences responsible for induction of one of the hsp70 genes of human cells that is induced by heat, cadmium, the adenoma virus Ela protein, and the addition of serum to serum starved cells has been mapped. In this system there appear to be different sequences responsible for the cadmium and heat shock induction, than for the serum stimulation and possibly the viral induction.

Regulation of Stress Response

A striking feature of heat-shock gene expression is that the responses of different organisms, and, indeed, of different cell types within an organism are regulated in different ways. In *E. coli* and in yeast the response is controlled primarily at the level of transcription. In Drosophila regulation is exerted on transcription, translation, and message turnover. 5' upstream sequences are postulated to serve in the transcriptional activation; the activation site maps to a consensus element shared by all eukaryotes. A synthetic promoter sequence derived from this consensus region seems to be sufficient for at least partly heat-inducible transcription in heterologous systems. The consensus element sequence (HSE) and a heat-shock transcription factor (HSTS) that binds to the HSE, have been isolated and characterized. Most heat shock genes appear to contain multiple consensus elements.

Heat shock proteins are also regulated at the translational level in most organisms. In Drosophila the translation of heat shock proteins depends upon sequences in the 5' region. Few inducers are able to effect this translational response. When hsps have accumulated in sufficient quantities, the translation of pre-existing non-heat shock messages is restored and the translation of heat-shock messages is repressed.

Despite many intriguing empiric observations of stress response, major unanswered questions remain about stress-response systems, including how they function to exert their protective and tolerance-inducing effects, and what is the extent of inducible stress and specific stress ranges. The specific protective mechanisms of stress response have proven elusive quarry. Components of the systems have generally not been identified, isolated and purified.

Understanding these mechanisms and identifying, isolating and purifying their components, would provide methods for controlling the responses of an organism to its environment. For example, teratogens that cause developmental malformations, also induce hsps. This may be the cause of the malformations; alternatively, the well-known variation in individual responses to teratogens may reflect differences in their genetic stress response. If the latter is the case, malformation risk may be reduced by enhancing the stress response systems. The present invention elucidates some of these genetic stress-response mysteries and discloses the isolation, purification and manipulation of stress response system components. Clinical and commercial uses of stress response systems are described which have not been previously developed.

GENERAL DESCRIPTION OF THE INVENTION

The present invention relates to methods and compositions which result from the identification, isolation, purification and manipulation of components of stress response systems. In particular, aspects of the invention disclosed herein, are genes and gene expression products which are capable of protecting cells and organisms from succumbing to potentially toxic stress factors in their environment. These components have been harnessed to make them commercially and clinically useful. Applications include control of pathogens and pests, improvement in food processing, enhancement of agricultural productivity, improvement of cancer therapy, in particular that employing heat, and prevention of developmental anomalies caused by teratogens. The applications may be grouped into the following general categories: enhancing the stress-response capabilities of cells, tissues or organisms and increasing their tolerance to stress; conversely, rendering cells, tissues and organisms more sensitive to stress, and inhibiting or reducing their tolerance to stress.

The ability of an organism to withstand exposure to many forms of physical stress, such as high temperatures, ethanol, heavy metal ions, and long term storage in the cold, is altered by altering the expression of genes encoding stress protector proteins.

For purposes of this invention, stress is defined as any factor or agent which is potentially deleterious to the cell, generally being a value outside of the physiological range at which the organism is able to function. Heat stress, for example, is defined as those temperatures that are at least at the upper or lower end of the organism's natural growth range.

The stress response system of the present invention comprises a regulatory system which is capable of a enabling structural genes to be expressed. At least one promoter or regulatory area is necessary for operation of the genetic stress response system. In an illustrative embodiment, this promoter is inducible by at least one environmental stress factor. Factors found to be inducers include heat, ethanol, cadmium, sodium arsenite, and nitrogen starvation. Alternatively, heterologous promoters for example, promoters induced by hormones or sugars, are suitable promoters. In an illustrative embodiment a heterologous promoter is a hormone, such as deoxycorticosterone or deacylcortivazol. Sugars such as galactose or glucose may also act as inducers. The promoter may also be constitutive. Of great use to commercial and clinical applications of stress protector protein encoding genes is that by placing the coding sequences under the control of various promoters, e.g., the galactose regulated promoter gal 1, the thermotolerance of cells varies with the presence or the absence of the sugar. That is, it is easily subject to heterologous control with exposure to stress.

The genetic stress response (stress protector) system comprises at least one structural gene whose expression is under the control of the promoter. The structural gene is capable of encoding a protein which is capable of protecting a cell, tissue or organism against potentially toxic effects of stress factors.

Stress response factors which induce the stress response system include heat, ethanol, arsenate, starvation, or cadmium. Remarkably, the stress protected against may comprise a stress different from that used as an inducer. In fact, the promoters may be induced by non-stress factors, yet the subsequent expression of the stress response genes will protect against stress. Conversely, the promoter region of the stress response system may be attached to structural genes that produce products other than stress response proteins. If these genes are placed under the control of the stress inducible promoter, their production can be controlled by exposure to environmental stress.

In an illustrative embodiment, these proteins comprise the family designated the hsp100 proteins. This stress-response system has been identified, isolated, purified, manipulated and applied in the present invention. It has some similarities to other stress response systems, but it differs from all others in two respects. First, the hsp100 proteins are the only proteins to date with a demonstrated function in protecting organisms from several different types of extreme stress. Second, they are apparently not necessary for cellular functioning except when stress is present, that is, the are not a vital component of normal physiological functioning. An advantage of this property is that components of this system can be altered without disturbing other cellular functions which must remain intact for normal life.

Proteins in the hsp100 family have apparent molecular weights in approximately the range 80–120 kd as determined by SDS polyacrylamide gel electrophoresis. The apparent molecular weights have also been estimated from the nucleic sequences encoding the proteins. The structure of the hsp100 proteins includes two nucleotide binding sites. FIG. 1A, FIG. 1B, FIG. 1C and FIG. 1D shows the nucleotide sequence from positions 1 to 3727 of the *Saccharomyces cerevesiae* HSP104 gene and its predicted protein product; 1,000 nucleotide of upstream sequence and the full coding sequence are shown. Each line is 90 nucleotides long. Each site is composed of two parts, as underlined in FIG. 1E, a glycine flexible loop and a beta strand. In an illustrative embodiment, the nucleotide binding sites are ATP, binding sites. At least one of these sites is essential for stress protection.

The hsp100 proteins generally have an amino acid sequence of about 900 residues and show particularly high levels of homology in regions surrounding the two nucleotide binding sites.

Proteins that are expressed by the hsp100 structural genes are members of a family of proteins designated here as hsp100 because the apparent molecular weights of the most prominent heat-inducible members are in the 80–120 kd range. They also share other properties and sequence homologies with the Clp family (FIG. 2A, FIG. 2B and FIG. 2C).

The hsp100 family of proteins is very highly conserved, comparable to other hsps families. The family most likely plays a major role in thermotolerance in all organisms. Proteins in this family exhibit similarities to the ClpA protein but are even more highly homologous to ClpB protein of E. coli.

Clp family members identified by sequence homology appear to be mitochrondrial. This may be a characteristic of the family. They are likely to be chaperone proteins that facilitate the export of proteins needed for stress-respnse, directly or indirectly establishing the correct protein assembly. A function of ClpB type proteins may be to protect protein from denaturation when stressed.

That a single family of proteins plays such a pivotal role in protecting organisms against the toxic effects of disparate stresses such as heat, ethanol, and arsenite, as well as against the damage that accumulates during long term storage at low temperatures, suggests that tolerance is mediated under these different conditions through a common biochemical pathway. By inference, it also suggests that the lethal lesions induced by such exposures are similar.

In an illustrative embodiment of the present invention the hsp100 protein comprises hsp104. Prior to this invention, heat shock proteins had been suspected to protect cells from a wide variety of stresses. However, it was not clear whether any one protein would function in protection against very different types of stress. Indeed, many investigators questioned the importance of heat-shock proteins in stress tolerance. The isolation, purification and manipulation of the hsp104 mutation demonstrated that the hsp104 protein plays an essential role in an extraordinary variety of circumstances. For example, it protects cells from heat, ethanol and sodium arsenite.

Hsp104 plays a vital role in protecting yeast cells from killing by high temperatures and other types of stress, such as ethanol and heavy metal ions. Electron microscopy demonstrates that one major protective function of the protein is to prevent the accumulation of massive aggregates of cellular components in the nucleus and cytoplasm at high temperatures. Although of vital importance in resistance to stress, the protein is not required for normal growth, at either high or low temperatures. Sequence analysis reveals that the protein is a member of the highly conserved clpA/clpB protein family which was first identified in E. coli but not known to be induced by high temperatures or other types of stress, nor to have any general protective functions. The yeast protein is more closely related to clpB than to clpA. Analysis of proteins and RNAs demonstrates that ClpB is induced at high temperatures and that additional heat-inducible members of this family are present in mammalian cells and in Schizosaccharomyces pombe. Thus hsp104 is a member of a new class of high conserved heat-shock proteins, the hsp100 family, which plays an important role in the ability of most organisms to tolerate extreme stress.

The inference from the effects observed with hsp100 gene mutations is that the wild-type gene products have the properties that are reduced by the mutation.

Mutations in the hsp104 gene of Saccharomyces cerevisiae were introduced into the genome by gene conversion using the constructs illustrated in FIG. 3A, FIG. 3B, FIG. 3C, FIG. 3D and FIG. 3E. Mutations do not noticeably effect general fitness. That is, the mutant cells grow as well as wild-type cells at normal temperatures (FIG. 4A) (in some media, they actually grow better than wild-type cells). Moreover, unlike cells carrying mutations in certain other heat shock genes, cells carrying mutations in the hsp104 gene grow as well as wild-type cells at the upper end of the natural temperature range of yeast cells (FIG. 4A) and do not lose viability even during prolonged incubation at 38.5° C. (FIG. 4B). Thus, the mutation does not reduce survival by making cells sick in a general way and thereby reducing their ability to survive stress. The mutation specifically effects a special pathway which exists to allow them to cope with physical stress.

The mutations in the hsp104 gene have several effects:

a) they greatly reduce the ability of log phase, fermenting yeast cells to acquire tolerance to high temperatures (FIG. 5B and FIG. 5C);

b) they greatly reduce the basal thermotolerance of respiring yeast cells, stationary phase cells and spores (FIG. 6A, FIG. 6B, FIG. 6C, FIG. 6D, FIG. 6E, FIG. 6F, FIG. 7A and FIG. 78);

c) they greatly reduce the ability of respiring yeast cells to acquire tolerance to high temperatures (FIG. 6A, FIG. 6B, FIG. 6C, FIG. 6D, FIG. 6E and FIG. 6F);

d) they greatly reduce the ability of yeast cells to tolerate high concentrations of ethanol (FIG. 8A and FIG. 8B);

e) they reduce the ability of yeast cells to tolerate exposure to heavy metal ions such as sodium arsenite (FIG. 9A, FIG. 9B and FIG. 9C);

f) they reduce the ability of yeast spores to tolerate long-term storage in the cold (Table 1);

g) they reduce the ability of cells to tolerate desiccation;

h) they cause slightly higher rates of growth in some media, notably acetate which forces them into respiratory metabolism (Table 2).

Notably, the fact that these mutant phenotypes can be reversed by transforming cells with a copy of the wild-type hsp104 gene demonstrates that they are a direct consequence of the absence of hsp104 in the mutant (for example, FIG. 5C).

Additional points of interest are that by adding extra copies of the wild-type stress response gene to yeast cells, the cells natural ability to survive high temperatures is increased.

Hsp104 is the largest protein reported in yeast cells that is strongly heat inducible (FIG. 10A, FIG. 10B, FIG. 10C and FIG. 10D). It is characterized by an apparent molecular weight of approximately 104 kd after SDS-polyacrylamide electrophoresis. Also, the amino acid sequence derived from the gene sequence predicts a molecular weight of 102.1 kd. In glucose media, hsp104 is not detectable at normal growth temperatures, but becomes a major product of protein synthesis shortly after a shift to high temperatures.

Interestingly, hsp104 is also expressed at normal temperatures during growth on acetate or galactose, media that support higher rates of respiration than glucose (FIG. 11A, FIG. 11B and FIG. 11C). This higher basal expression confers cells with higher basal levels of thermotolerance, and is presumably of selective advantage. However, at least in acetate, hsp104 expression also produces a selective disadvantage, slower rates of growth and lower stationary phase cell densities. One explanation for this phenomenon is suggested by considering the preferred substrate for yeast growth, glucose, and the first secreted product of its catabolism, ethanol. Under normal circumstances, yeast cells switch to the respiration of ethanol when glucose is exhausted and ethanol concentrations have increased. It is exactly at this point of the growth curve that hsp104 is induced. Because ethanol is itself toxic, and because hsp104 plays an important role in mitigating this toxicity, the induction of hsp104 in respiring cells may simply be a general protective response. That is, under natural conditions, increased protection may be worth a possible reduction in growth rate during extended respiratory growth. It is important to note, however, that under other circumstances the expression of hsp100 in the absence of stress does not have detrimental effect on growth or viability. For example, when the coding sequences of the hsp014 gene were placed under the control of a galactose-inducible promoter, or a steroid hormone-inducible promoter, induction did not noticeably affect the growth rate of the cells. It did, however, increase their ability to tolerate heat.

Immunofluorescent localization shows the hsp104 protein to be present throughout the cell, with more intense concentration in the nucleus during exposure to extreme temperatures (FIG. 12A and FIG. 12B). Presumably, it affects a large number of biochemical processes in the cell. RNA splicing is blocked in most organisms at high temperatures and protected by conditioning heat pretreatments. Splicing is protected by heat pretreatments to nearly the same extent in mutant and wild-type cells. However, once splicing is disrupted (e.g., by a sudden heat shock at 41° C.), the process recovers much more rapidly in the wild-type than in the mutant. It may be that other heat shock proteins play more important roles in protecting vital cellular processes from disruption (Skawya, 1990; Pelham, 1986; Rothman, 1989; Riabowal, 1988), while hsp104 is specialized to repair damage once it has been done. Electron microscopy demonstrates that mutant cells accumulate large aggregates of cellular components at high temperatures (FIG. 13A, FIG. 13B and FIG. 13C). Wild-type cells accumulate similar aggregates but at a very greatly reduced frequency. Thus, one function of the protein appears to be to prevent the denaturation and aggregation of cellular components or to promote the rapid renaturation and disaggregation of such components after they have been damaged.

The hsp104 mutation provides information on the action of other tolerance factors in yeast cells and demonstrates that the relative importance of hsp104 versus these other factors varies considerably with different types of stress. During exposure to extreme heat (55° C.) or very high concentrations of ethanol (20%), 1,000 to 10,000 fold differences in survival are seen between mutant and wild-type cells after a mild heat pretreatment (e.g. 30 minutes at 37° C.). Mutant cells produce all of the other known stress proteins but are specifically missing hsp104. Under such conditions, mutant cells display little or no residual tolerance. That is, differences between cells given a conditioning pre-treatment or not, are small. Under less extreme conditions, lower temperatures (44° C.–50° C.) or lower concentrations of ethanol (10–17%), 10 to 100 fold differences in survival are observed between the mutant and wild-type cells. In these cases, pre-treated and naive mutant cells do differ, with pretreated cells showing at least a transient ability to resist killing. With sodium arsenite, differences between the mutant and wild-type are more modest, between 2 and 10 fold. In this case, the importance of other inducible tolerance factors is even more apparent. Pre-treated mutant cells show substantial and sustained tolerance compared to naive cells.

Hsp104 is a highly conserved protein. Closely related, heat-inducible genes have been detected in mammals, Drosophila, trypanosomes, plants, and bacteria (FIG. 14A, FIG. 14B, FIG. 14C, FIG. 14D, FIG. 14E and FIG. 14F). In this respect hsp104 is comparable to the other heat-shock proteins, hsp70, hsp90, and hsp60. However, the biological role of hsp104 appears to differ from that of the other major heat-shock proteins in an important way. Hsp70, hsp90, and hsp60 either play vital roles in normal growth and development themselves or have close relatives that do. There is no evidence for such a role for hsp104. Deletion of the gene has no effect on the rate of growth in glucose at either 25° C. or at 37° C. In fact, in acetate media, growth rates actually increase when the HSP104 gene is deleted.

With regard to killing by copper or cadmium, the hsp104 protein is of little or no protection. Both copper and cadmium are capable of inducing tolerance to higher concentrations of copper and cadmium. However, this tolerance is not significantly compromised by the hsp104 mutation. Thus, all agents that induce the heat-shock response may not rely upon the same protective mechanisms. It is not surprising that there should be fundamental differences in the toxicities of certain hsp inducers, but to date these have been difficult to assess. The hsp104 mutation provides a genetic tool for dissecting the causes of lethality under different types of stress.

The yeast life cycle proceeds from ascospores produced by meiosis through spore germination, said spores going through a process of mitosis (cell division). The resulting haploid cells are then able to combine into a diploid zygote by nuclear fusion. These diploid cells then undergo further cell division to bud off new cells. Hsp104 is induced during life cycle transition to stationary phase growth and is induced early in the process of sporulation (FIG. 11A, FIG. 11B and FIG. 11C).

In many organisms hsps are highly induced not only in response to heat, but also during the course of normal development. In Saccharomyces, hsp26, hsp82, hsp104, and at least one member of the hsp70 family are induced in stationary phase and during ascospore development (FIG. 11A, FIG. 11B, and FIG. 11C). The biological significance of developmental hsp inductions has been unclear. For example, deletion of the HSP26 or the HSP82 gene of yeast has no effect on sporulation itself nor on the long-term viability or thermotolerance of stationary phase cells and spores. The hsp104 mutation, however, has a profound effect on these cell types. They are severely compromised in their ability to withstand heat. Moreover, they do not withstand long term storage as well as wild-type cells, even at 4° C.

Additional members of this heat-inducible protein family were found in human cells and *Schizosaccharomyces pombe*. Subclones of the HSP104 gene, containing either the amino-terminal half or the carboxy-terminal half of the coding sequence, hybridize to heat-inducible RNAs of the appropriate sizes from these organisms (FIG. 14C, FIG. 14D and FIG. 14E). Moreover, antibodies raised against HSP104 peptides cross react with a heat-inducible polypeptide of approximately 105 kD from *S. pombe* and with two polypeptides of approximately 110 kD in both Chinese hamster ovary cells and in HeLa cells (FIG. 14C, FIG. 14D, FIG. 14E, and FIG. 14F). In both mammalian cell types, one protein is constitutive and the other heat-inducible.

Hsp104 appears to be a member of the ClpA/ClpB gene family, first identified in *E. coli* (FIG. 2A, FIG. 2B and FIG.

2C). The ClpA protein was reported not to be induced by heat. The ClpB messenger RNA and protein are induced at high temperatures (FIG. 14A and FIG. 14B), and the physical properties of HSP104 are similar to those previously reported for ClpA. Hsp104 shares with the other members of the ClpA/ClpB family two regions of amino acid sequence that are homologous to other known nucleotide binding sites. The ClpA protein is the only protein in this family that was previously known to employ ATP for its functioning. Site-directed mutagenesis, a technique used in yeast by those of skill in the art, demonstrates that generally both ATP sites are required for hsp104 to function in thermotolerance (FIG. 15C and FIG. 15F).

This invention also relates to a genetic construct comprising at least one regulatory element and at least one structural gene, said structural gene being capable of producing a protein expression product which counteracts potentially toxic effects of environmental stress factors. This genetic construct comprises the components of a stress response system that protects the organism against stresses including heat, cold, ethanol, arsenite, starvation or desiccation. Promoters of the genetic construct generally used include those capable of initiating the expression of a protein in response to stress. Alternatively, other regulatory factors such as those that respond to hormones or sugars, or those than provide for constitutive expression can be used to induce the protein.

The structural gene of the present invention comprises a nucleic acid segment having a nucleotide sequence coding for a stress response protein. This protein has the properties of the hsp100 family disclosed herein. That is, the protein is capable of protecting against stress, and shows at least 25% amino acid sequence homology with the sequence shown in FIG. 1A, FIG. 1B, FIG. 1C, FIG. 1D and FIG. 1E.

This invention does not relate only to a specific nucleic acid sequence, but rather to a nucleotide sequence homologous and functionally equivalent to that shown in FIG. 1A, FIG. 1B, FIG. 1C and FIG. 1D which encodes the amino acid sequence essentially as set forth in FIG. 1A, FIG. 1B, FIG. 1C, FIG. 1D and FIG. 1E, or the biologically functional equivalent thereof. In addition, segments within the sequence are within the scope of the invention. In an illustrative embodiment, the nucleotide sequence segment contains bases capable of encoding for an amino acid sequence sufficient to protect an organism or a cell against stress. This would include at least one nucleotide binding site. In an illustrative embodiment, the nucleic acid segment may be composed of DNA, for example, that encoding hsp104, a sequence of about 3.6 kb.

The nucleic acid segment comprises a sequence which corresponds to at least a 14 base pair long region, said region capable of hybridizing to the nucleic acid sequence of FIG. 1A, FIG. 1B, FIG. 1C and FIG. 1D or to its complement. A hybridizing segment of at least 20 nucleotides is also contemplated up to about 40 nucleotides.

This invention also relates to a method of constructing strains or genetic variants of organisms with alterations in a genetic stress response system or components thereof. In an exemplary embodiment of such a method, genetic constructs comprising at least one nucleic acid segment capable of encoding a stress response protein are prepared. Provision is made for placing this nucleic acid segment under regulatory control as disclosed herein. This regulatory control and nucleic acid system is then incorporated into the yeast cell. Methods of incorporation may comprise those methods well known to those skilled in the art, for example, electroporation, transformation microinjection, and the like.

Finally, to produce the strains that have incorporated the genetic construct containing the stress response system, cells will be placed under conditions which are conducive to growth or reproduction. These conditions are well know to those skilled in the art, for example, microorganisms can be plated on agar media or grown in liquid media. Multiple copies of the nucleic acid segments encoding stress protector proteins may also be incorporated.

There are several methods for preparing a stress response protein. In an exemplary embodiment, a recombinant vector is prepared and incorporated into a cell, and the recombinant vector is expressed in the host to produce the protein. If desired, the protein may be isolated from the host cell and also further purified. This protein may then be employed to alter the tolerance of an organism to stress by direct application (e.g., microinjection, electroporation, or lipofection). In another exemplary embodiment, the protein itself may be added to sensitive biological materials in vitro and employed to protect them and processes in which they participate from damage by denaturation, stress, or long term storage.

A recombinant vector may be produced by standard methods well known to those skilled in the art (See Material and Methods herein). The vector generally includes a nucleic acid segment, said segment capable of encoding at least one stress response protein. In an illustrative embodiment, the recombinant segment corresponds to bases specifying the amino acids number 1 to 909 in accordance with FIG. 1A, FIG. 1B, FIG. 1C, FIG. 1D and FIG. 1E. This is the complete coding sequence. In another illustrative embodiment, the segment corresponds to the bases encoding amino acids 150 to 400 or amino acids 550 to 750. These are highly conserved regions including the nucleotide binding domains. The recombinant segment will generally be under the control of an effective promoter, as disclosed herein.

Methods of preparing nucleic acid segments which comprise at least the functional stress response portion of the coding sequence include obtaining genomic nucleic acids from eukaryotic or prokaryotic cells which comprise at least one coding region capable of expressing an active stress response protein, preparing recombinant clones which include at least one of the coding regions for the stress response protein, and selecting clones which comprise the desired amplified nucleic acid segment. Amplification may be accomplished by the polymerase chain reaction. Host cells will generally comprise in addition to the genetic construct for stress response, a promoter which provides for transcription of the gene and a translation initiative site which provides for expression of the protein from the gene transcript. Host cells may be eukaryotic cells, for example, yeast or human cells, or bacterial cells, for example, a lactobacillus or *E. coli*.

One of the important properties of the stress response system disclosed herein is to be able to induce tolerance to stress factors. This phenomenon refers to increasing the cell's or organism's ability to survive severe stress treatments which would otherwise be injurious causing the organism to produce the stress-protective protein.

The expression of a protein from the family hsp100 induced by stress, need not be induced by the same stress for which protection is being sought. Alternatively, the protein could be induced by other specific inducers that the recombinant gene is engineered to respond to, such as a sugar or a hormone. In another exemplary embodiment, the organism is engineered to produce the protein in the absence of specific inducers. This should result in higher constitutive or basal thermotolerance.

In another embodiment, the proteins may be introduced into the organism to induce tolerance. The degree of tolerance induced will be proportional to the number of copies of the gene or the plurality of proteins introduced into the cells of the organism, until saturation is reached.

The proteins may be introduced into in vitro compositions to facilitate biological process. Examples are in vitro photosynthesis or production of products using biological processes that have protein intermediates. Any process which depends upon proteins maintaining their proper structure and proper interactions with other proteins, and which are compromised and limited by protein denaturation or aggregation, will benefit from addition of stress protector proteins. These proteins prevent denaturation or aggregation, or repair of such damage already accumulated. This intervention facilitates processes being run at higher pressures, or for longer periods of time, than without the stress protection proteins.

This invention also relates to methods of detecting a stress response (strss protector) protein. These methods are of value in determining and predicting the response of a particular set of cells or an organism to stress, or to identifying homologous genes. In an exemplary embodiment, the method consists of preparing antibodies directed against the protein, reacting tissue samples with the labelled antibodies, and detecting the antibody-protein immune complexes. Hsp100 related proteins might also be assayed by other immunological methods such as western blotting or enzyme-linked immunoabsorption assays. Antibodies are prepared by purifying the protein or a segment of the protein or by synthesizing a segment of the protein that is sufficient to induce specific antigenicity, injecting the purified protein into rabbits or other animals capable of producing antiserum, and extracting the antiserum directed to the protein, from the rabbit. These immune complexes may be assayed by many different methods, for example, with labelled protein, or labelled secondary antibody. Alternatively, the antibodies directed against the stress protein can be directly labelled with, for example, biotin, fluorescein, or radioactive compounds. Monoclonal antibodies are also contemplated by this invention.

A method of detecting a nucleic acid segment encoding for at least a fragment of a stress protector protein in biological samples consists of preparing a nucleic acid probe which is capable of hybridizing to a nucleic acid segment substantially as set forth in FIG. 1A, FIG. 1B, FIG. 1C and FIG. 1D, or a functional equivalent thereof, labelling the probe, incubating the probe with the biological sample to be tested under selective conditions appropriate for the formation of specific hybrids, and detecting the formation of specific hybrids between the probe and the nucleic acid segment in the biological sample by detecting the label. The formation of such hybrids is indicative of the presence of the desired nucleic acid segment. Another method of detection consists of preparing oligonucleotide probes complementary to any separate sequences in the gene and using them to amplify the intervening sequences or divergent sequences in the target gene by the polymerase chain reaction (PCR amplification). This method is well known to those of skill in the art.

Antagonists of a nucleic acid segment capable of encoding hsp100 stress proteins, or inhibitors of said proteins may be also prepared. The purpose of antagonists, antisense molecules, blockers, neutralizing antibodies, peptide inhibitors, and the like, is to disrupt the functioning of the stress response system. Such agents, therefore, are suitable for use as part of a method for destroying, altering, or inactivating cells. An illustrative example of such a method comprises treating cells with at least one of the antagonists, neutralizing antibodies, blockers or inhibitors, and exposing the cells to a stress which would not be severely toxic to the cell in absence of the antagonist. The stresses to which a cell may be exposed may comprise temperatures which are toxic to the cells without the expression of heat-shock genes, for example, in yeast cells, this would be temperatures of about 50° C. at least.

In an illustrative embodiment of a method for destroying, altering or inactivating cells, a nucleic acid sequence capable of coding for a stress response protein may be prepared. At least one mutation is introduced into the nucleic acid sequence sufficient to disrupt the expression of the sequence in the form of a functional stress response protein. Any method of inducing mutations is within the scope of the present invention. Site specific mutagenesis is currently the preferred method. The mutated nucleic acid sequence is then delivered to cells. In one exemplary embodiment, the mutated gene may be used to replace the wild-type gene by gene conversion. This is the method that was employed to create mutations in the yeast hsp104 gene. In another embodiment, the cells may be transformed with genes constructed to produce nucleic acids that are complementary to the hsp100 transcripts (antisense transcripts). The antisense transcript hybridizes to the transcript of the normal gene and prevents its expression. This antisense method has been used to reduce the expression of other genes including heat-shock genes, e.g. hsp70 (See Materials and Methods). In another embodiment, a mutated gene is constructed which produces a faulty protein which interacts with the cells normal stress protector protein, blocking its expression. This creates a dominant negative mutation. For example, a carboxy-terminal deletion of hsp70 had a severe dominant negative effect on thermotolerance, although a minor effect an regulation. An amino-terminal deletion had the converse effect.

Cells transformed with mutated genes may then be exposed to certain levels of stress which are capable of causing the cells to die at an increased rate. This type of method is useful for preparation of recombinant cells and transgenic organisms whose viability may then be controlled by stress exposure.

Methods for destroying, altering or inactivating cells are also useful for cells that are in a disease related tissue. In these applications the method may be used to destroy the tissue by altering its stress response system and exposing the tissue to stress, thus alleviating symptoms of the disease. In an illustrative embodiment, the disease related tissue is a tumor and the tumor is thereby rendered more sensitive to stress. Mutations may be directed to the nucleic acid of the cell or organism itself to render the genes incapable of being expressed as a stress response protein. Alternatively, antibodies against the stress-protective protein or inhibitors of its function can be employed to block tolerance to stress.

One of the most exciting uses for the stress response system is to control an organism's response to stress. In this application a genetic construct is prepared comprising a stress response gene capable of being expressed, and a genetic promoter which is inducible by the stress. The genetic construct is introduced into the organism. The organism is then exposed to at least the level of stress capable of inducing expression of the stress response gene.

For certain applications, it will be useful to select a genomic DNA fragment from another organism which contains a nucleic acid sequence capable of producing a stress response protein. In an illustrative embodiment, a cross-reacting antiserum is applied to an expression library of DNA fragments from the organism cloned into a vector. The recombinant vectors that give positive signals with the antiserum are selected. The positive clones are then analyzed for the presence of a DNA fragment coding for a stress response protein.

Numerous industrial applications of this stress response system are within the scope of the present invention. An illustrative embodiment is the preparation of processed products wherein organisms are routinely used to process a food product such as beer, cheese or sake. These foods would benefit from applications of these methods because the organisms could be removed without employing a stress level which may be damaging the quality of the food itself. An improved method for removing the organism after the process is complete makes use of the stress response system of the present invention. For example, at least one mutation is induced in the nucleic acid sequence coding for a stress response protein of the food processing organisms. The mutations are sufficient to make the organism incapable of tolerating certain levels of stress. The mutated organisms may then be used to process the product as usual. After the product is processed it may be exposed to levels of stress which are now toxic to the mutated organisms. These stresses might include heat, ethanol, long-term storage, or a combination of such stresses.

One of the concerns surrounding the release of recombinant organisms produced by genetic engineering methods into the environment, is that these organisms may become disruptive because they are now not under control. Methods of the present invention may be used to control such recombinant organisms. The stress response system of the recombinant organism is altered to prevent survival, except in a particular environmental niche. After release of the organism into a natural environment, the level of stress response is predetermined such that if the organism moves beyond the desired ecological niche, it will be rendered incapable of surviving.

A similar method may be used for pest control by forming recombinant pests that comprise a genetic construct with an impaired ability to respond to environmental stress by producing the appropriate stress protective proteins. These recombinant pests may then be interbred with natural pest populations whereby the defective stress response constructs are spread within the population. Eventually the pest population may be exposed to artificial stress, or in their natural life cycles, they will encounter lethal stress ranges and be destroyed. For example, eliminating the expression of hsp104 actually gives yeast cells a growth advantage in acetate media. In mixed populations, in the absence of stress, cells carrying such mutations should therefore be able to outcompete other yeast for growth in such media. When exposed to stress, however, the organisms carrying such mutations would be destroyed.

In a different type of application, the objective may be to enhance or trigger the expression within a host of a stress response protein, even in the absence of stress. This may be achieved by delivering a vector in vitro to cells derived from the host tissue. The vector should comprise at least one promoter region and at least one structural gene capable of coding for a stress response protein. These cells which now contain the stress response system may be reintroduced into the host tissue and the genes within the vector may be activated by exposing the tissue to a factor which will induce the promoter. Activation of the structural genes will then enhance the level of the stress response protein in the cells at a level proportional to the number of copies introduced. This will give cells carrying the gene an advantage for survival.

The methods of the present invention may be used to enhance plant crop productivity or animal survival. Both plants and animals that are raised for agricultural purposes have problems when encountering certain levels of environmental stress. By incorporating into the plant or animal a genetic construct capable of enhancing production of stress response proteins, and then either exposing the plant or animal to stress, or placing it in its natural environment, the stress induced proteins will be sufficient to protect the organism from deleterious or toxic effects of the environment.

A method for preserving the quality of organs or tissues stored at cold temperatures is to introduce genes functionally related to a plurality of genes coding for the cold stress response proteins into the genetic complements of the cells or tissues to be preserved. Alternatively, the protein itself or a functional fragment of the protein might be introduced into the cells by methods such as lipofection or electroporation. The enhanced levels of protective proteins in these cells would maintain the viability of the tissue longer than do currently standard methods.

In cases where it is not practical to introduce such genes or proteins into cells, assays for expression of the protective genes or proteins could be employed to optimize treatment of the cell or tissues prior to storage. In an illustrative embodiment, blood cells could be exposed prior to storage to conditions which maximize the expression of the protective hsp100-related proteins without injuring the cells. Antibodies against the protein or nucleic acid probes could be employed to maintain the level of induction of the protective protein to ensure that the optimum response was achieved prior to storage. Such a method is broadly applicable to the storage of microorganisms, plants, cells, tissues, and even whole organisms.

Limitations on biological processes imposed by the build-up of aggregated or denatured proteins, will be eliminated or reduced by introduction of stress response proteins. The processes that will benefit from the methods of the present invention include any process that depends on proteins maintaining their structure and proper interactions with other proteins. These processes are compromised when proteins are denatured or aggregated during the process. These problems develop when proteins are exposed to denaturing temperatures, high pressures, or long processing times. The result is impairment of the process.

Introduction of stress protector proteins into the processes before the degradation and aggregation will prevent such problems developing. If introduced after the process is underway, the stress protector proteins can repair already aggregated or denature proteins. Addition of the stress response proteins, or at least fragments of the protein sufficient to prevent protein denaturation or aggregation, or to repair such damage, will facilitate and extend the processes. Examples of stress protector proteins are hsp104 and 70.

BRIEF DESCRIPTION OF THE DRAWINGS

Figure 1A:
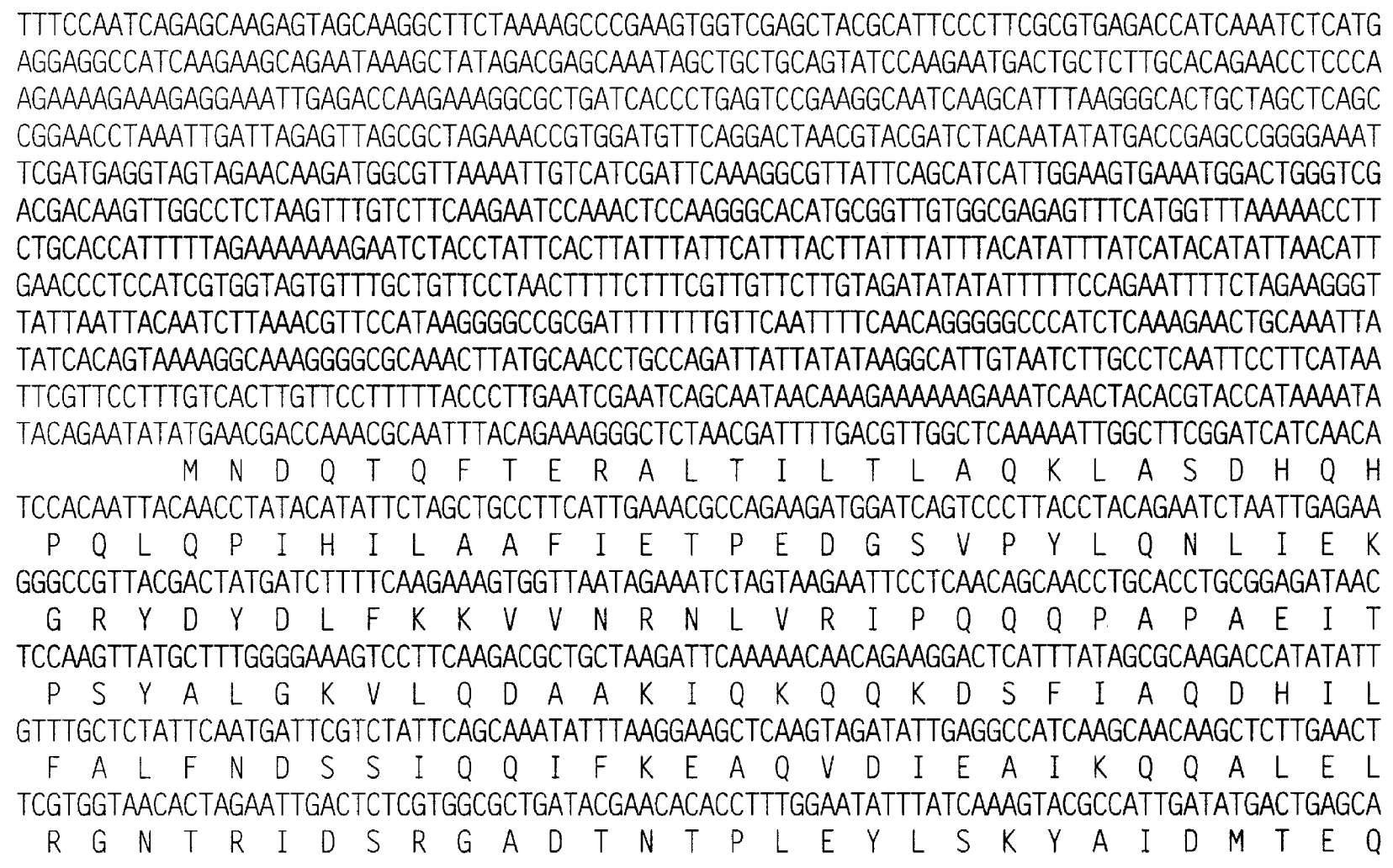
Figure 1B:
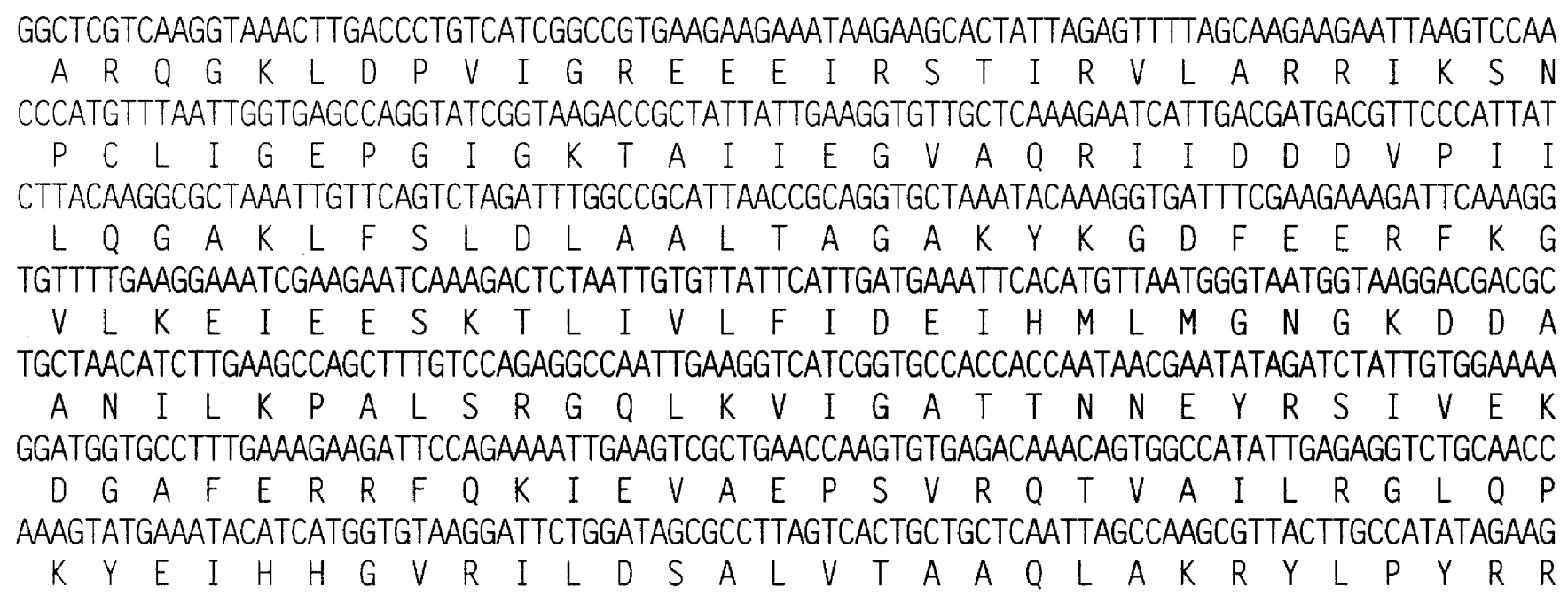
Figure 1D:
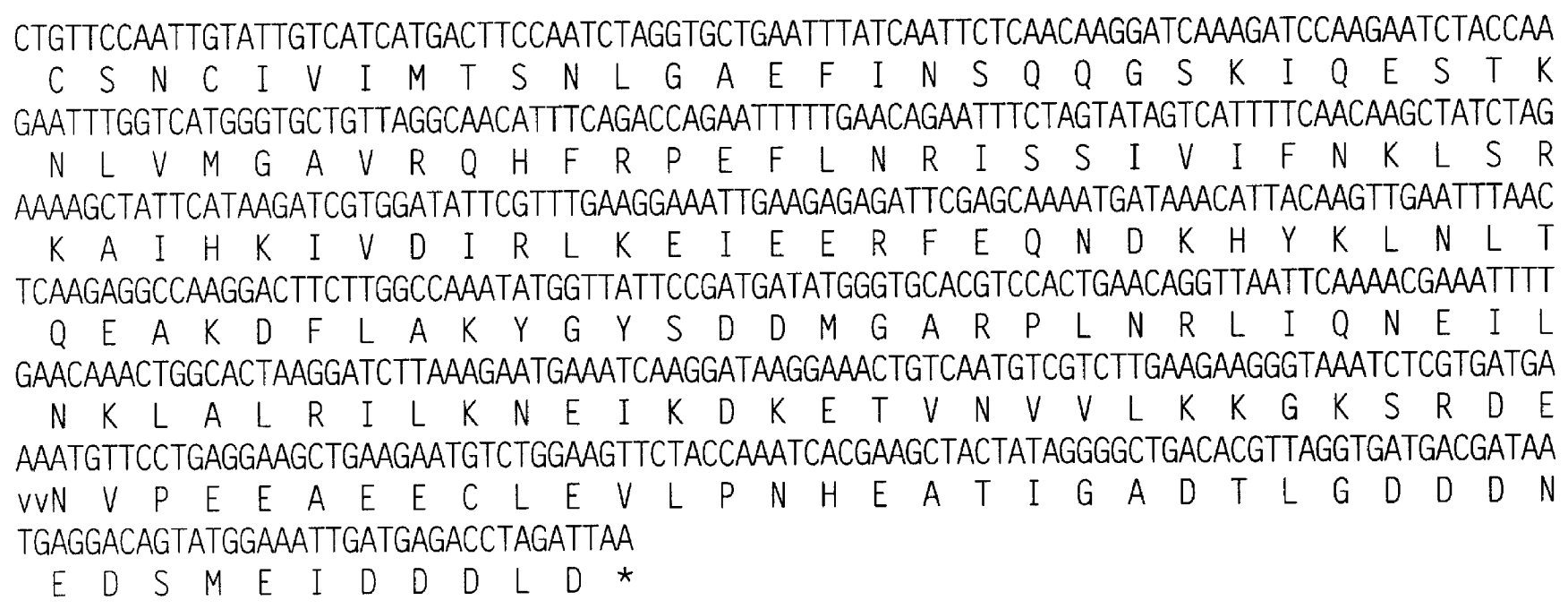

FIG. 1A, FIG. 1B, FIG. 1C, FIG. 1D and FIG. 1E FIG. 1E Amino acid sequence of the hsp104 protein; FIG. 1A, FIG. 1B, FIG. 1C and FIG. 1D). Sequence range: 1 to 3727 of the *Saccharomyces cerevisiae* HSP104 gene and its predicted protein product; 1000 nucleotides of upstream sequence and the full coding sequence, are shown. Each line is 90 nucleotides long.

FIG. 6A, FIG. 6B and FIG. 6C survival of mutant and wild-type cells at 50° C. without pretreatment at 37° C., basal thermotolerance; FIG. 6D, FIG. 6E and FIG. 6F after pre-treatment at 37° C.

FIG. 8A Thermotolerance after ethanol pre-treatment; FIG. 8B effect of pre-treatment by ethanol on ethanol tolerance.

FIG. 9A) Survival of mutant and wild-type cells after pre-treatment with arsenite and exposure to 50° C.; FIG. 9B) and FIG. 9C) colony forming capacity as a function of arsenite exposure.

FIGS. 10A–10D. Induction of hsp104 by heat or stationary phase arrest: FIG. 10A) Protein synthesis; FIG. 10B) Western blot; FIG. 10C) Northern blot; FIG. 10D) Protein synthesis in mutant vs. wild-type cells.

FIG. 11A) glucose or galactose; FIG. 11B) late stationary phase and sporulation; FIG. 11C) ethanol, arsenite or copper sulfate.

FIG. 13B) wild-type cells at high temperature; FIG. 13C) mutant cells at normal temperature.

FIG. 14A) Heat-inducibility of the ClpB messenger RNA; FIG. 14B) Heat inducibility of the ClpB protein; FIG. 14C) Hybridization of probes from the amino-terminal half of the hsp104 coding sequence, to total cellular RNAs from control and heat-shocked cells of widely divergent species—*S. pombe* and human cells. AN RNA homologous to hsp104 is induced of the size expected to encode a member of the hsp100 family; FIG. 14D) Antibodies raised against portions of the *S. cerevisiae* hsp104 protein react with heat-inducible proteins of the correct size in *S. pombe*; FIG. 14E) Antibodies raised against portions of the *S. cerevisiae* hsp104 protein react with heat-inducible proteins of the correct size in *S. pombe* in human cells; and FIG. 14F) Antibodies raised against portions of the *S. cerevisiae* hsp104 protein react with heat-inducible proteins of the correct size in *S. pombe* in chinese hamster ovary cells.

FIG. 18A) Antisense mutant cell line; FIG. 18B effect of extra copy of hsp70; FIG. 18C wild-type; FIG. 18D composite graph of FIGS. 18A–18C.

DESCRIPTION OF THE PREFERRED EMBODIMENTS

This invention identifies a new family of highly conserved stress response proteins which appear to play important roles in the ability of most organisms to tolerate extreme stress. These proteins are designated the hsp100 family, for purposes of this invention. The gene encoding one of the proteins, hsp104, and its promoter has been cloned. (FIGS. 1A–1E) Other hsp100 genes have been identified by sequence homologies. The stress protector proteins have been purified (See Materials and Methods).

To clone the gene for the protein encoding a member of the hsp100 family, the largest yeast heat-shock protein, hsp104, an antibody against the protein was produced and used to screen a library of yeast DNAs inserted into an expression vector in *E. coli*. Positive clones were subcloned into appropriate vectors for more detailed analysis of the gene.

Deletion mutations were induced in the gene by the site-directed gene conversion technique (Rothstein, 1983). The deletion mutation was marked by the insertion of a selectable auxotrophic marker (FIGS. 3A–3E).

Figure 4A:
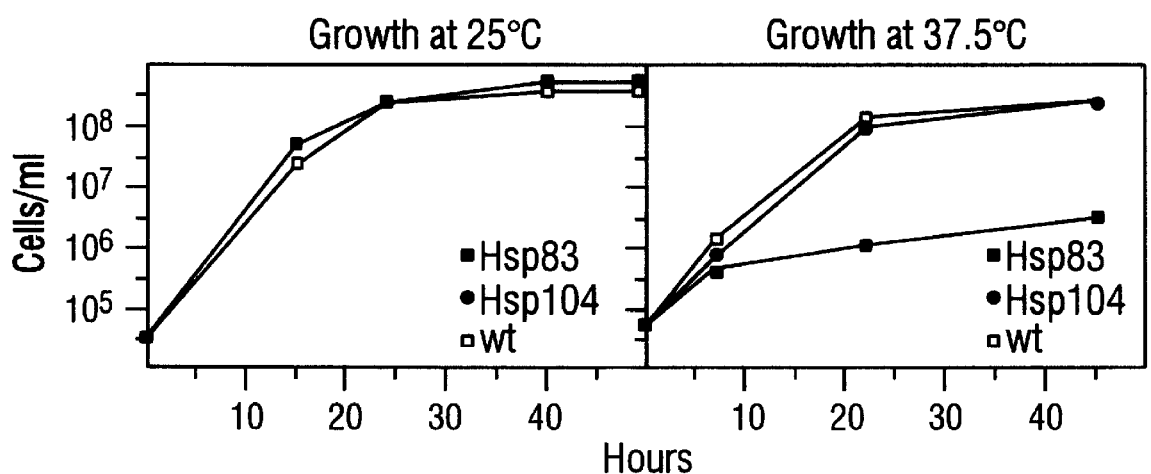
FIGS. 4A and 4B. Mutation of the HSP104 gene does not affect (FIG. 4A) growth at 25° C. or at 37.5° C., or (FIG. 4B) long-term survival at 38.5° C.
Figure 4B:
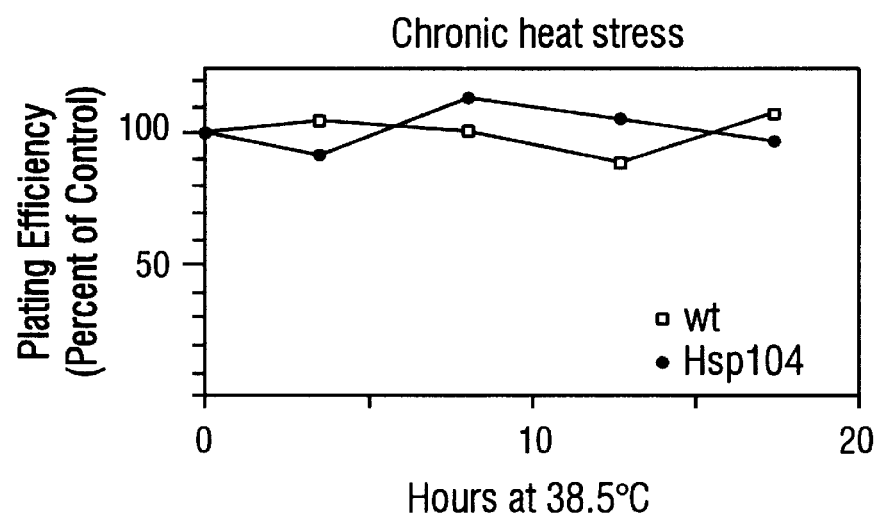

The ability of mutant and wild-type cells to grow at normal temperatures (25° C.) and at moderately elevated temperatures (37° C.) was compared. At each temperature, both mutant and wild-type grew at the same rate (FIG. 4A) Mutant cells also survived long incubations (up to 15 hours) at 38.5° C. as well as wild-type cells (FIG. 4B). This demonstrates that the mutation does not cause a general lack of fitness.

Figure 5A:
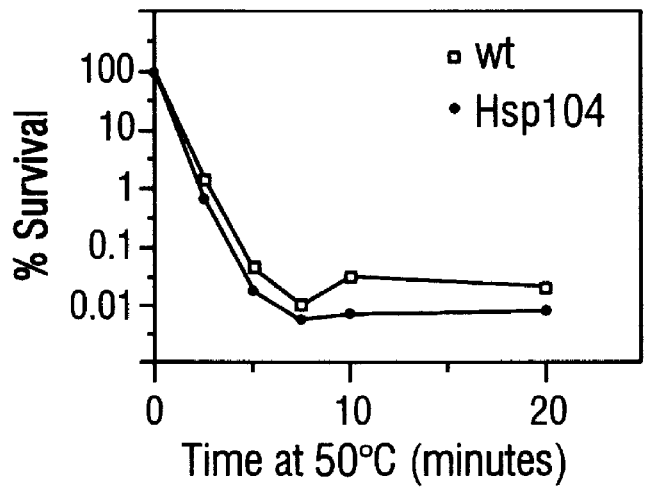
FIGS. 5A–5C. Mutation of the HSP104 gene affects the induction of thermotolerance.
Figure 5B:
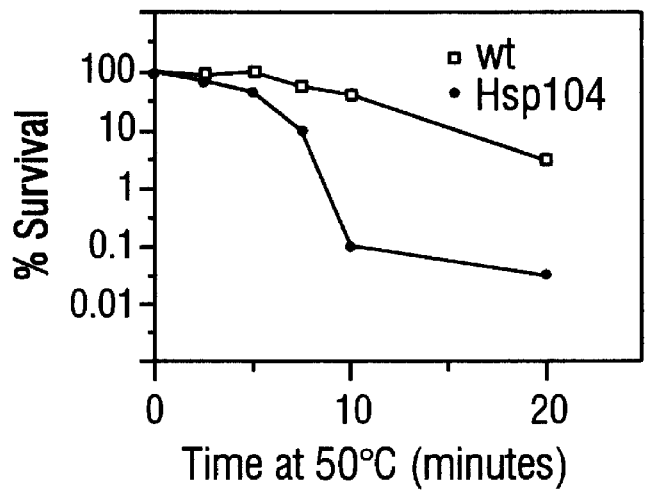
Figure 5C:
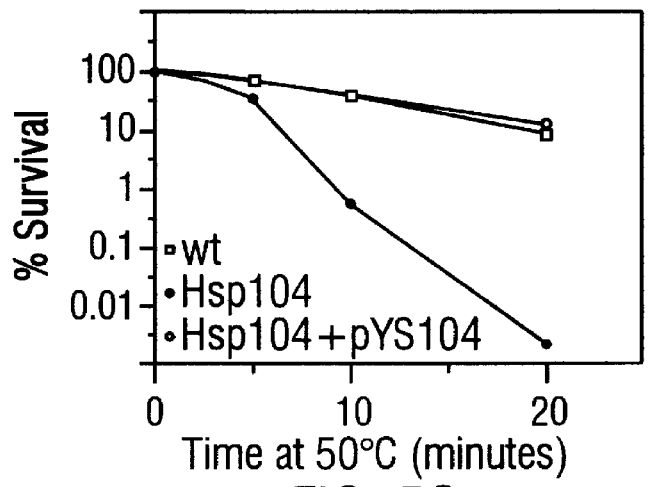

The ability of mutant and wild-type cells to survive high temperatures was compared. Cells carrying the hsp104 mutation had a greatly reduced ability to tolerate exposure to 50° C. After 20 minutes, a one hundred fold difference in survival was seen in mutant and wild-type cells (FIGS. 5A–5C).

It was demonstrated that reduced survival at high temperatures was the result of the hsp104 mutation, and not of any other accidental change that might have taken place in the cells. To do so, the entire wild-type gene, including regulatory flanking regions (FIGS. 3A–3E), was cloned and put back into the strain carrying the mutation. This restored the ability of the cells to tolerate extreme temperatures (FIG. 5C).

Figure 6A:
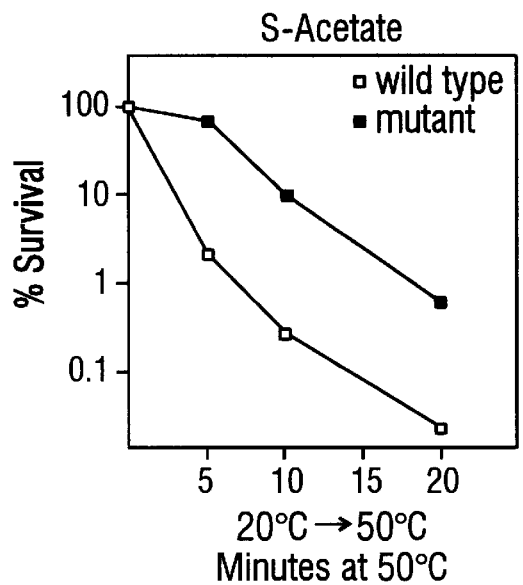
FIGS. 6A and 6F. Colony forming ability of cells grown in acetate, galactose or glucose and incubated at 50° C.
Figure 6B:
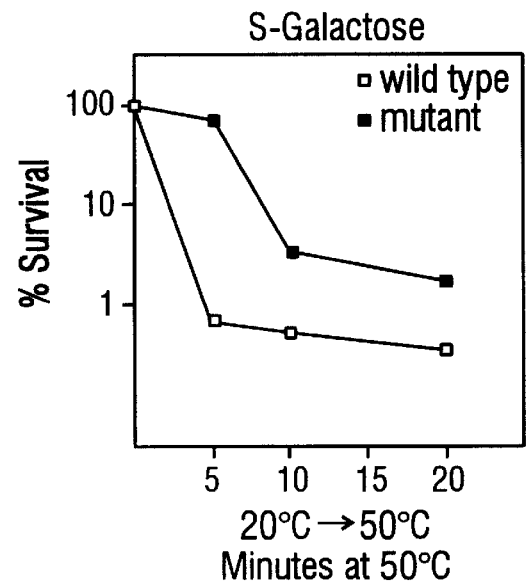
Figure 6C:
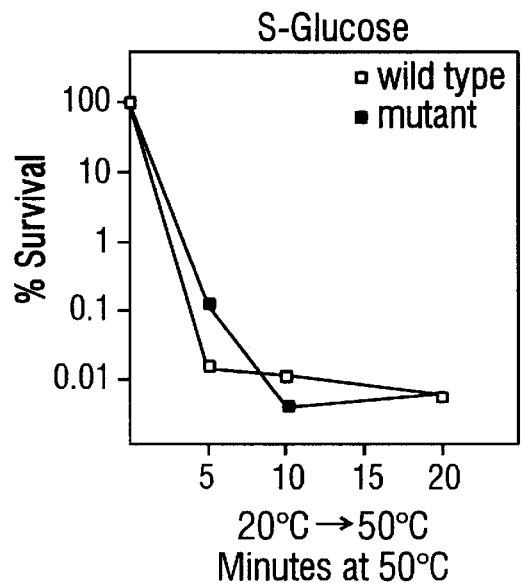
Figure 6D:
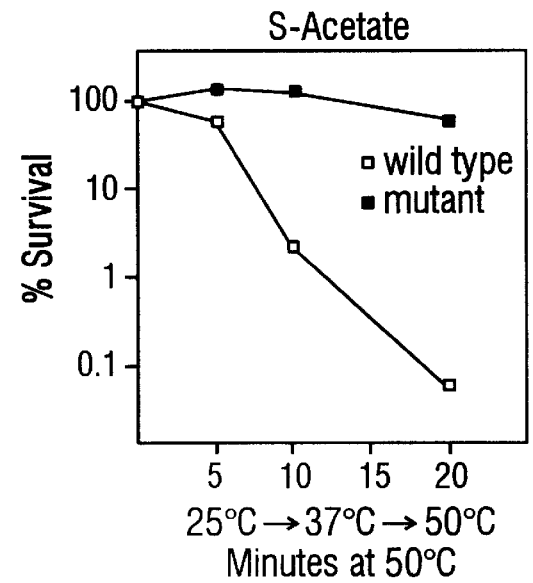
Figure 6E:
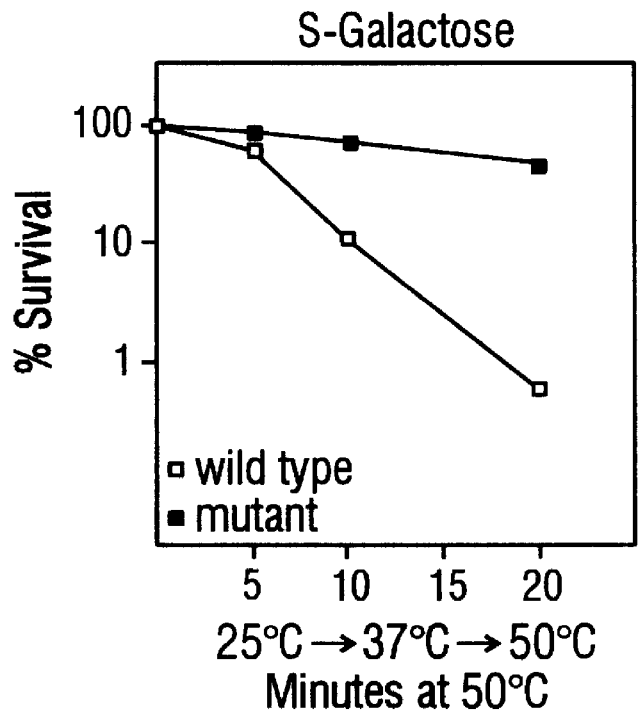
Figure 6F:
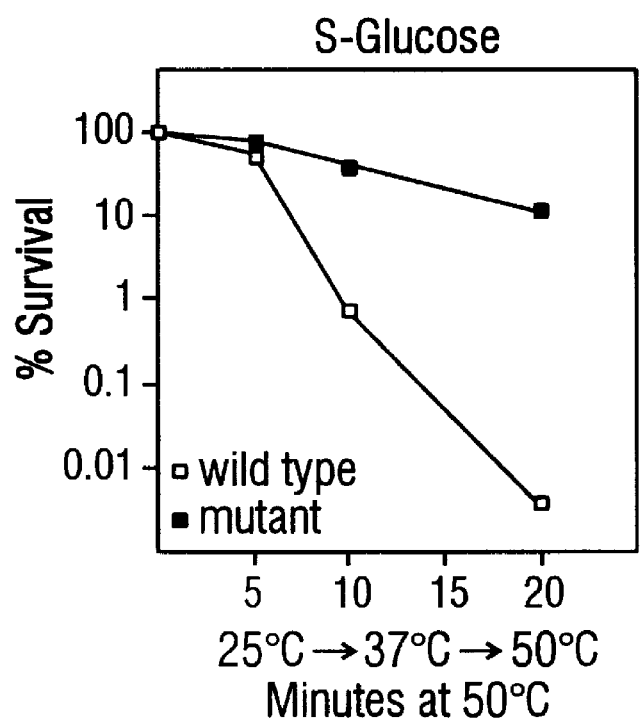
Figure 7A:
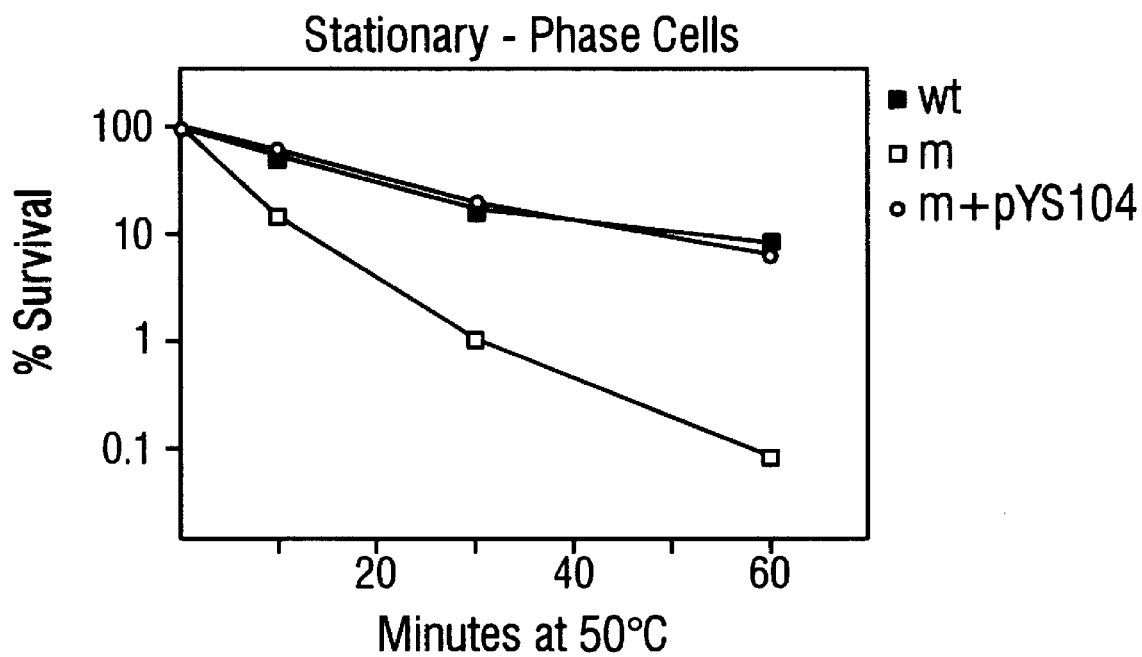
FIGS. 7A and 7B. Mutations in the HSP104 gene reduce the naturally high thermotolerance of stationary phase cells and spores.
Figure 7B:
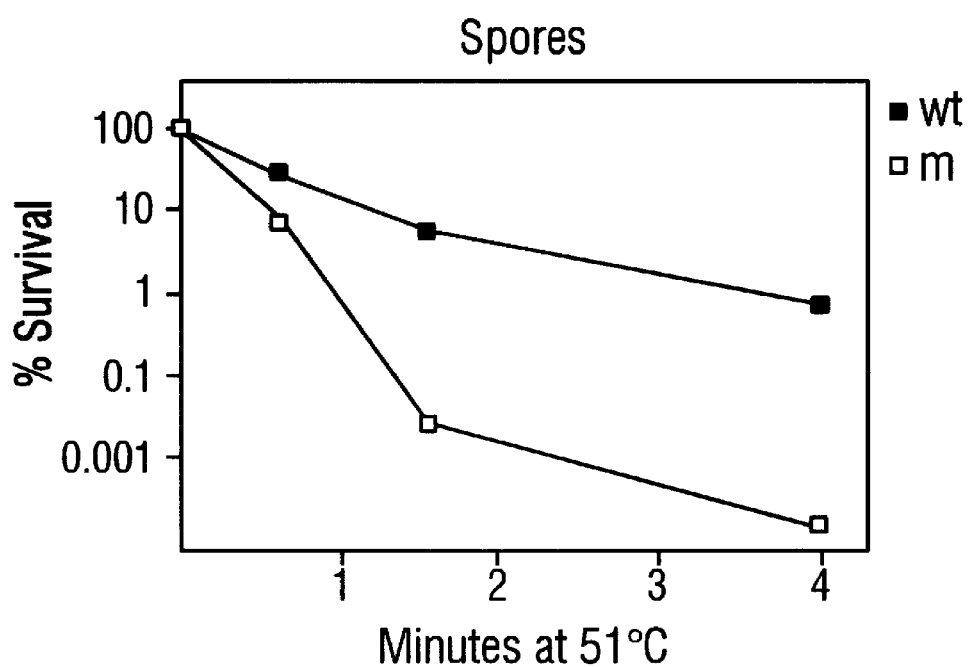
Figure 8A:
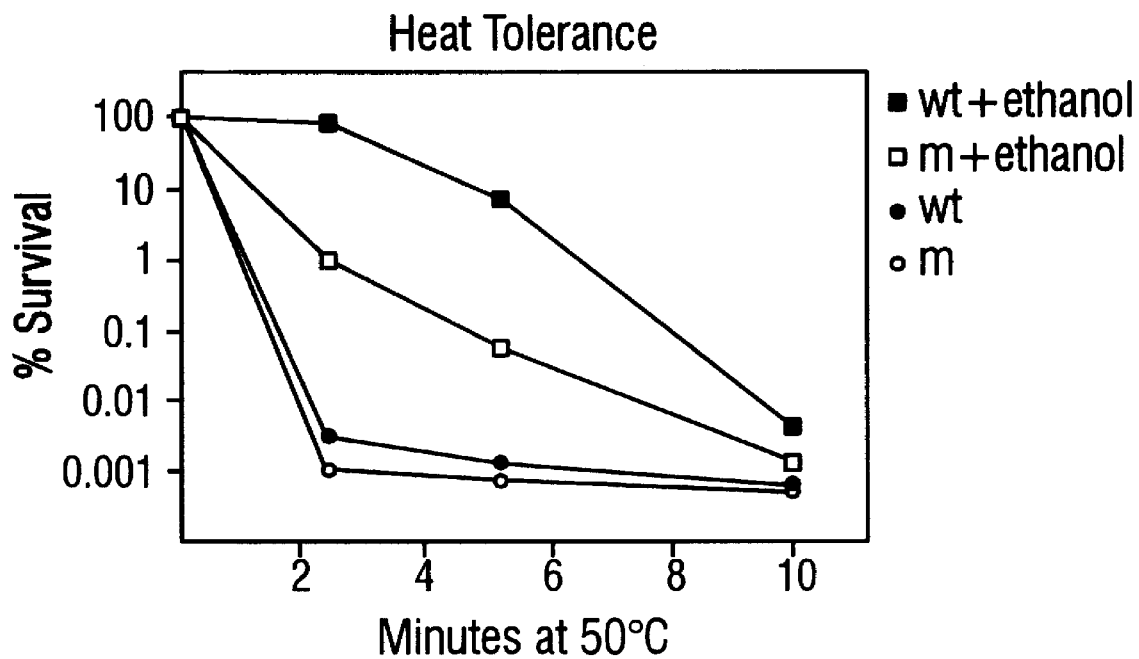
FIGS. 8A and 8B.
Figure 8B:
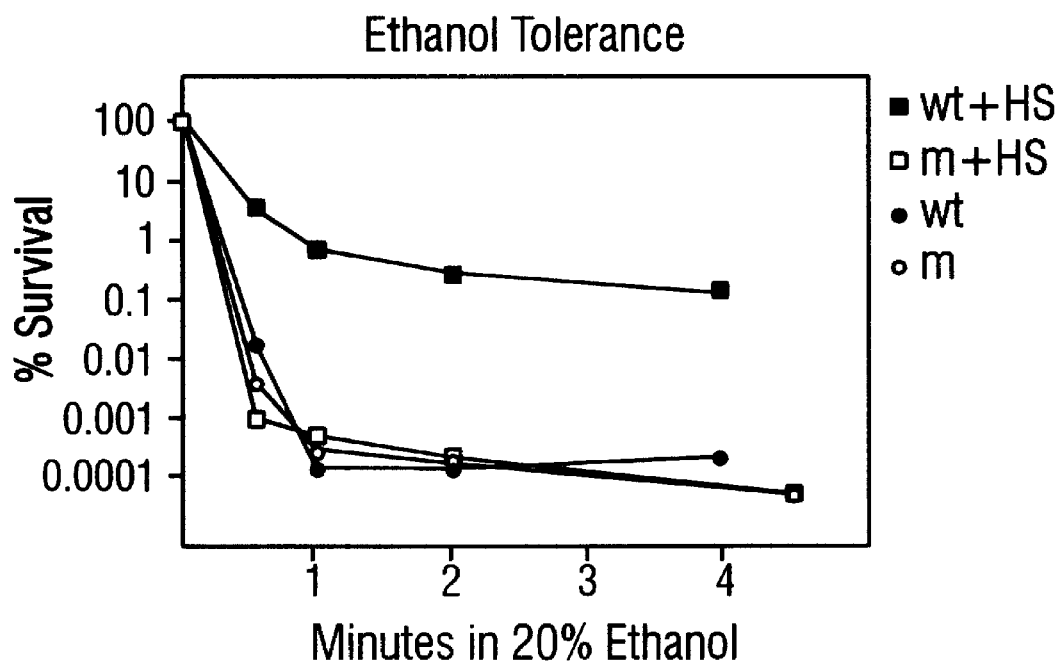
Figure 9A:
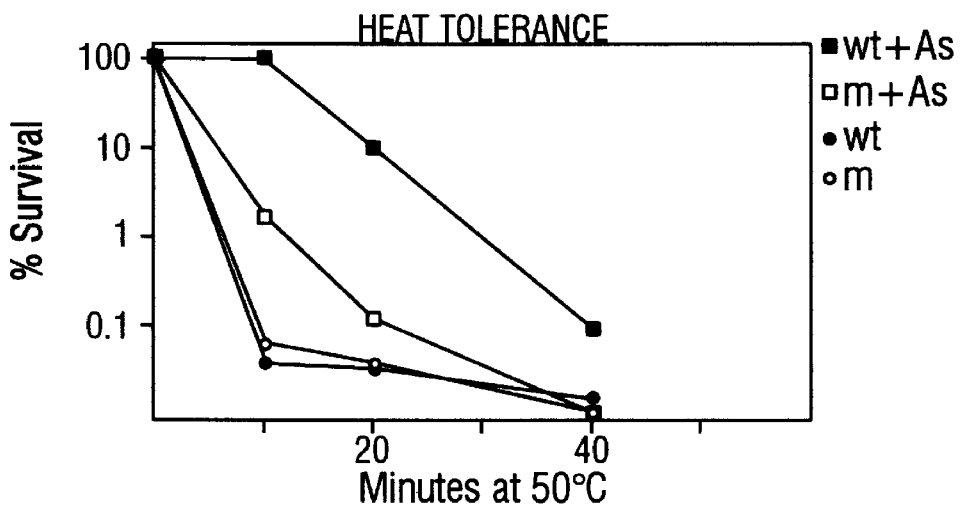
FIGS. 9A–9C.
Figure 9B:
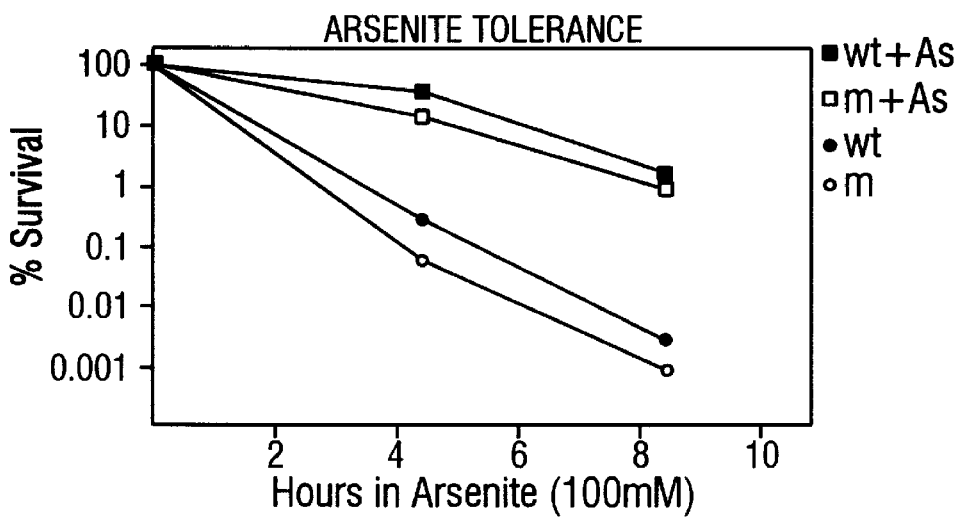
Figure 9C:
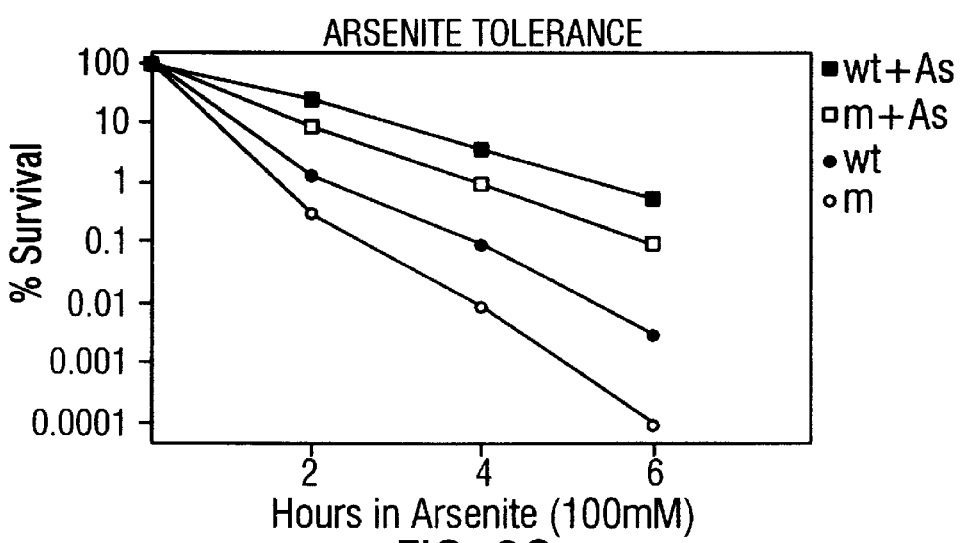

The ability of mutant and wild-type cells to tolerate several different types of physical stress was compared in a variety of different physiological states. Mutant cells were demonstrated to have a greatly reduced ability to survive after:

a) short-term exposure to extreme heat (5 minutes to 1 hour at 50° C.) in fermentative metabolism during growth on glucose medium (FIG. 6C and FIG. 6F);

b) short-term exposure to extreme heat in respiratory metabolism (during growth on galactose or on acetate media) (FIGS. 6A–6E);

c) short-term exposure to extreme heat in the stationary phase of growth (either after growth on glucose or on acetate media) (FIG. 7A);

d) short-term exposure to extreme heat after sporulation (that is, as mature spores) (FIG. 7B);

e) long-term exposure to much more moderate heat (30 minutes to 24 hrs. at 45° C.) in fermentative metabolism;

f) exposure to high concentrations of ethanol (12 to 20%) (FIG. 8B);

g) exposure to sodium arsenite (1 to 20 Mm for 2 to 12 or 24 hours) (FIG. 9B and FIG. 9C);

h) long-term storage in stationary phase cells in the cold (2 days to 4 weeks at 4° C.); and i) long-term storage as mature spores in the cold (6 months at 4° C.).

The same mutation was introduced into several different strains of Saccharomyces cerevisiae. All showed greatly reduced levels of thermotolerance.

The complete amino acid sequence of the gene was determined (FIGS. 1A–1E). The amino acid sequence predicts that the protein contains two ATP binding domains. Based upon the supposition that these regions would be likely to be functionally important, site-directed mutations were introduced in individual amino acids codons in these regions. These mutations had the same effect as the original deletion mutation, greatly decreasing the ability of the cells to tolerate extreme temperatures (FIGS. 15A–15F). These tests were performed in both log and stationary phases of metabolism. Thus, there are several different methods available for inactivating the hsp104 protein.

An extra copy of the wild-type hsp104 gene was added to wild-type cells. Cells carrying the extra copy of the gene had an increased ability to survive extreme temperatures.

Figure 16A:
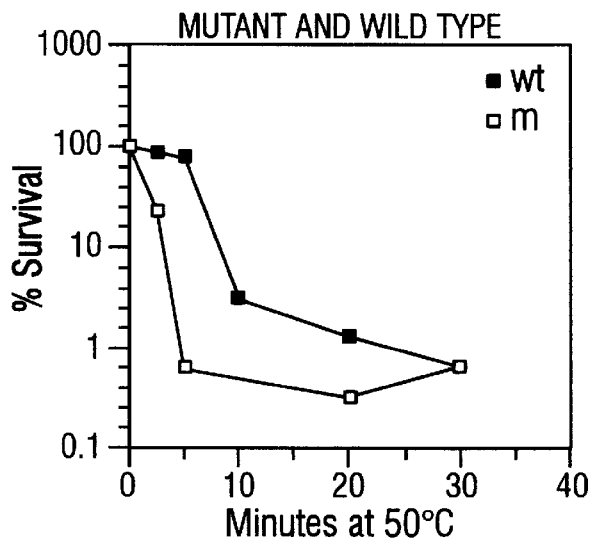
FIGS. 16A–C. In cells carrying mutations in the wild-type hsp104 gene and a chimeric gene for hsp104 in which coding sequences were placed under the control of the galactose-inducible promoter gal 1, survival at high temperatures depends upon the presence or absence of the sugar galactose.
Figure 16B:
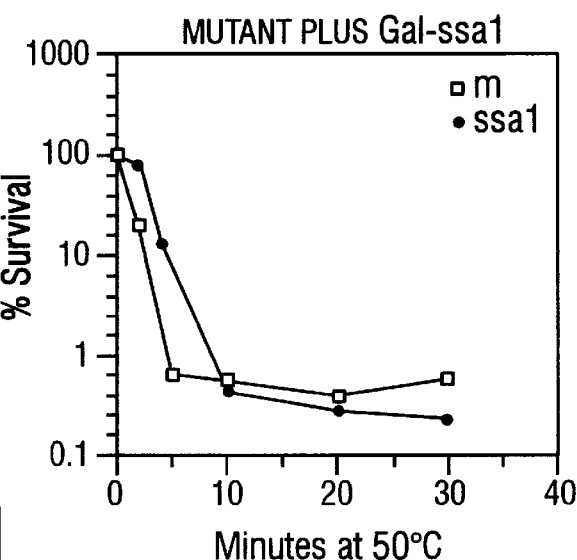
Figure 16C:
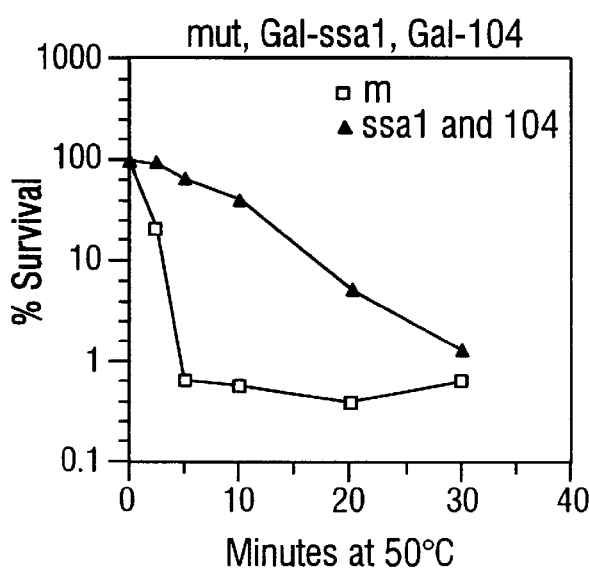
Figure 17:
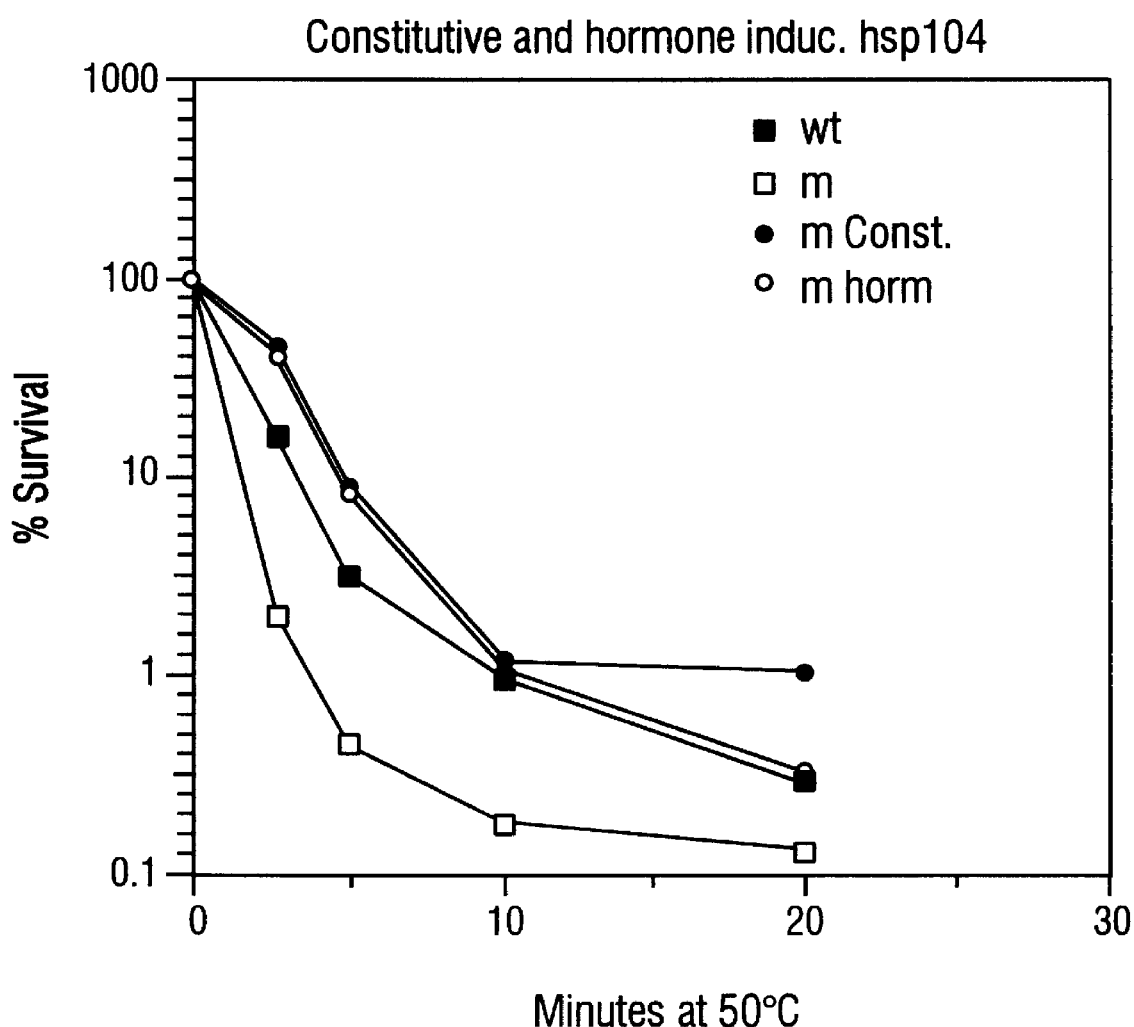
FIG. 17. Thermotolerance is increased by enhancing the expression of hsp104. Chimeric genes in which hsp104 coding sequences were placed under the control of a hormone inducible promoter were transformed into wild-type cells. Continuous incubation with the hormone or a 1 hour induction with the hormone increased thermotolerance.
Figure 18A:
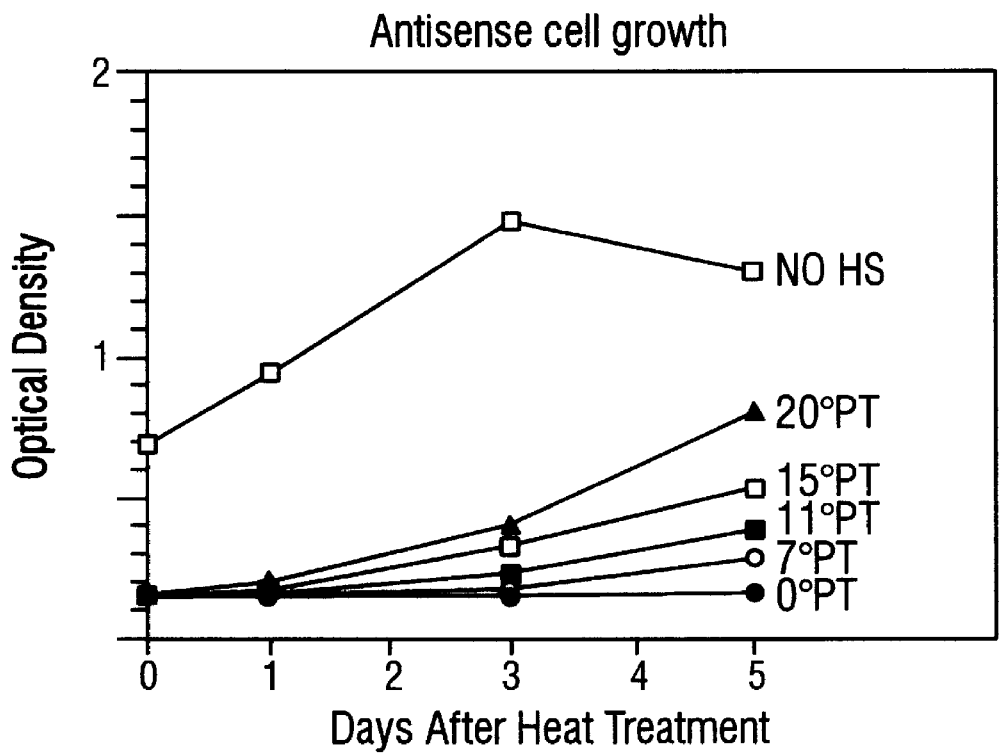
FIGS. 18A–18D. Effect of extra hsp70 on cell growth.
Figure 18B:
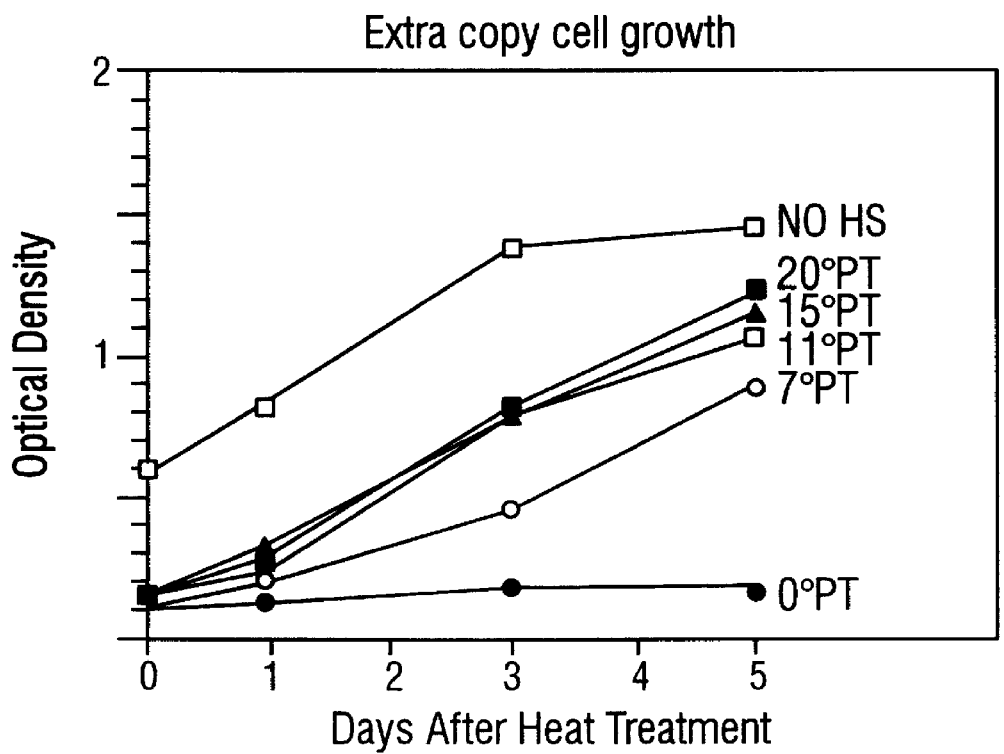
Figure 18C:
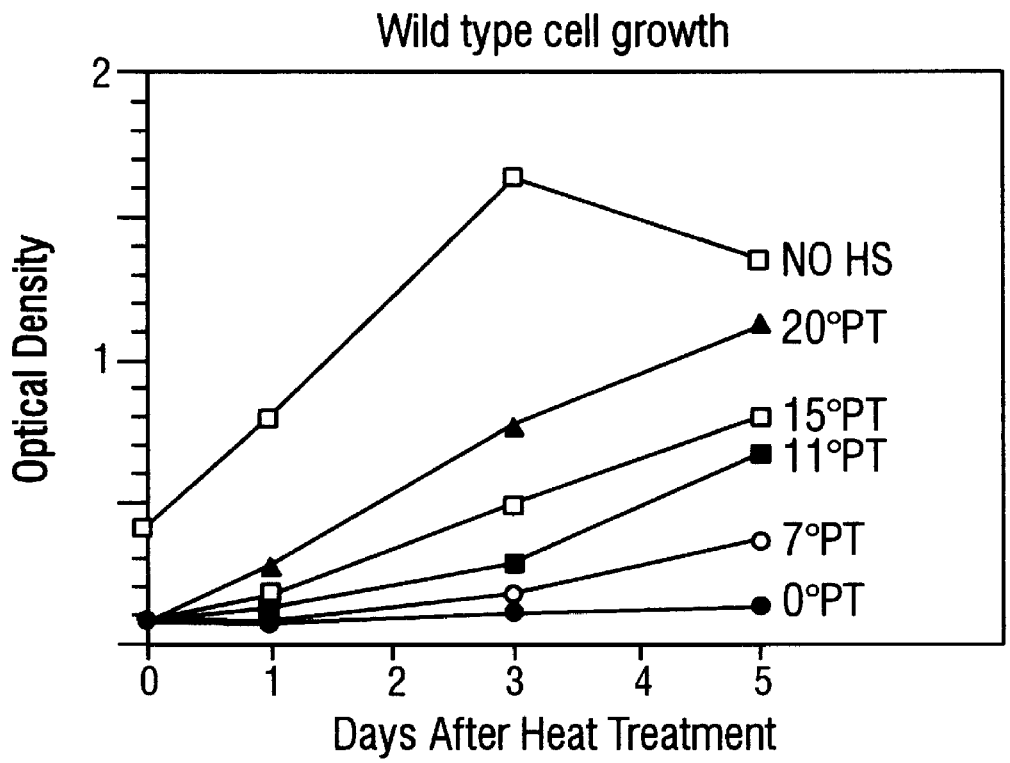
Figure 18D:
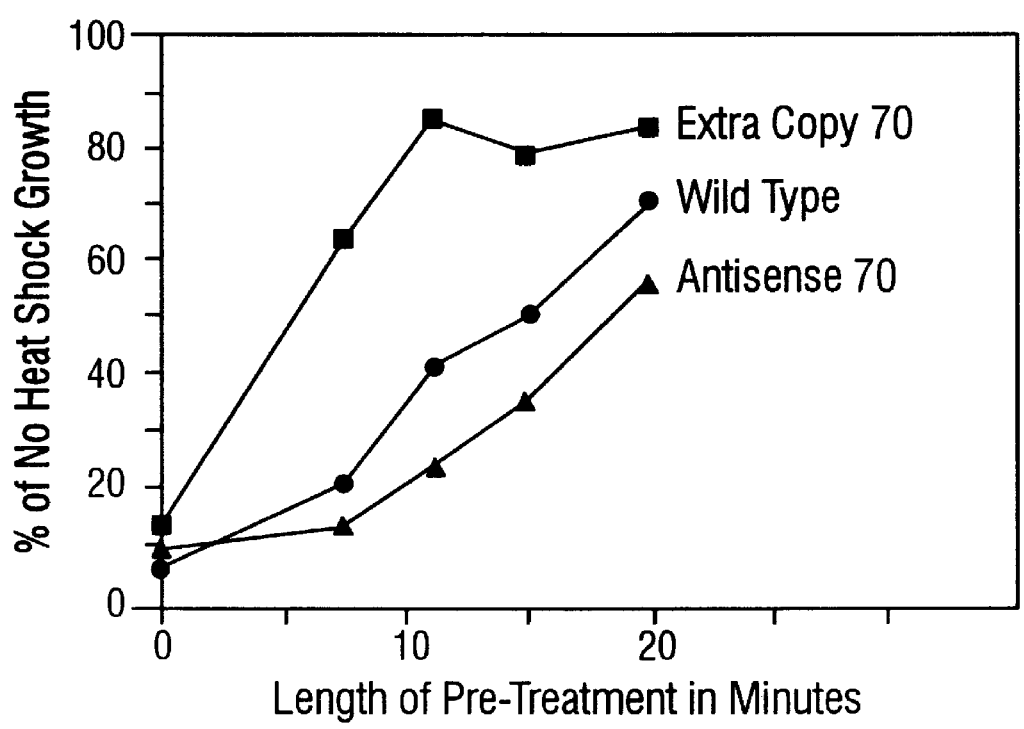

The coding sequences from the hsp104 gene were placed under the control of heterologous regulatory sequences, e.g. 1) the gal 1 promoter, or 2) the glucocorticoid inducible promoter. These promoters are regulated by the presence or absence of 1) the sugar galactose, or 2) hormones of the glucocorticoid class. In cells carrying these chimeric genes and a deletion of their normal hsp104 gene, their ability to survive high temperatures depended upon the presence or absence of the sugar galactose or the hormone deoxycorticosterone (FIG. 16A, FIG. 16B, FIG, 16C and FIG. 17) Thus, the ability of cells to survive at high temperatures can be controlled by heterologous inducers using chimeric genes.

Wild-type cells carrying a normal HSP104 gene were transformed with chimeric constructs in which HSP104 coding sequences were placed under the control of a hormone inducible promoter. When these cells were treated with hormones before being exposed to high temperatures, their ability to survive was increased. Thus, expressing the hsp100 proteins at higher than normal levels confers increased thermotolerance.

Other organisms, very distantly related to yeast, contain heat-inducible genes closely related to hsp104. Because most organisms produce a heat shock protein of the same size class as the yeast hsp104 protein, other organisms were tested and found to produce a messenger RNA that hybridizes with the yeast hsp104 gene. In two cases, in human cells and in cells of very distantly related fungus, hybridization to a heat-inducible poly-A containing RNA of exactly the expected size was detected. Thus, two organisms separated from S. cerevisiae by approximately a billion years of evolution contain genes that are very similar in sequence and patterns of expression to the yeast hsp104 gene. Furthermore, antibodies raised against portions of the S. cerevisiae protein cross-reacted with heat-inducible proteins of the appropriate size from human cells, chinese hamster cells, the very distantly related fungus Schizosaccharomyces pombe, and the bacterium E. coli (FIG. 14A, FIG. 14B, FIG. 14C, FIG. 14D, FIG. 14E and FIG. 14F).

EXAMPLE 1

Hsp104 is a Member of the hsp100 Family of Stress Response Proteins

In Saccharomyces cerevisiae, a member of the hsp100 family is the protein designated hsp104. This protein is required to protect log-phase fermenting cells from death at extreme temperatures. Hsp104 plays a vital role in thermotolerance under many different physiological conditions and a major role in tolerance to other types of stress. It is constitutively expressed in respiring cells, and is in large part responsible for the higher basal levels of thermotolerance in such cells. Its expression in stationary-phase cells and spores is crucial for the naturally high thermotolerance of these cells as well as for their long-term viability at low temperatures. The protein also appears to be of critical importance in effecting tolerance to ethanol and sodium arsenite. That a single protein is responsible for survival under such different conditions, indicates that the underlying causes of lethality are similar in an extraordinary variety of circumstances. The protein is of little or no importance, however, in providing tolerance to copper and cadmium. Thus, all agents that elicit the heat-shock response may not depend upon the same mechanisms for protection.

The hsp104 protein was purified by ion exchange chromatography and SDS gel electrophoresis and used to produce a highly specific polyclonal antiserum in rabbits by methods disclosed herein. As may be seen in FIG. 11A, FIG. 11B and FIG. 11C, hsp104 is constitutively expressed at an appreciable level during log phase growth in minimal acetate-containing media. In rich medium, constitutive expression was also observed. This was in marked contrast with glucose-grown cells, in which mutant and wild-type cells grow at the same rate and in which hsp104 is expressed at very low levels during log-phase growth, in rich or minimal media (FIG. 10A, FIG. 10B, FIG. 10C, FIG. 10D, FIG. 11A, FIG. 11B and FIG. 11C). The antiserum (FIG. 10A) was used to screen an expression library of yeast genomic DNA fragments in NftII (Young and Davis, 1983). Those that gave positive signals after repurification were selected. Of $3 \times 10^5$ recombinant phages screened, seven gave positive results. Restriction endonuclease mapping showed that these clones share overlapping fragments. A clone containing the biggest insert (YS121) (FIG. 2) was chosen. This clone has a 3.6 kb yeast DNA fragment between the $\Lambda$ arms. Heat inducible sequences were localized within this clone.

The stress response system leads to the production of a protein which does not play a vital role in the organism in the absence of stress, yet is instrumental in protecting the organism against extreme levels of stress. It is also capable of inducing tolerance to stress further by initial pretreatment at lower levels of the stress factor. It is likely that the concentration of the protein is directly proportional to the degree of protection provided until a saturating level of expression is obtained. The stress response system has capability of inducing tolerance to stress after a pretreatment comprising an initial exposure to the stress or to some other regulatory mechanism. The only requirement for the regulatory mechanism is that it be able to induce the expression of the structural gene.

An observed PI's of 6.2 is obtained by 2-dimensional gel electrophoresis with carboxymethylated albumin included as an internal standard. On such gels the protein appears as a single major spot with a minor, more acidic spot, suggesting that the protein is subject to modification. This pattern does not change after heat shock, during stationary phase, or when the protein is expressed in the absence of heat shock from a galactose inducible promoter.

In examples disclosed herein, a wild-type strain of the budding yeast *Saccharomyces cerevisiae* was compared with a strain isogeneic to it, except that it carried a mutation in the hsp104 gene. In several cases, a third strain was employed, which carried this same mutation but also carried a new copy of the wild-type gene on an extra-chromosomal plasmid. This third strain was employed to prove absolutely that the effects observed in the mutant strain were, in fact, due to the mutation that had been introduced into the hsp104 gene. That is, the effects of the mutation disappeared when the wild-type gene was added back to the cells. In all tests, mutant and wild-type cells were grown under identical conditions and exposed to the same stress at the same time. After the treatment, the cultures were diluted and plated onto rich glucose media to determine the number of live cells, that is the number of cells which were capable of forming colonies.

Cells carrying a deletion mutation in the HSP104 gene grow at the same rate as wild-type cells in glucose at both 25° C. and 37° C. (FIG. 4A). They also die at the same rapid rate when shifted directly to 50° C. (FIG. 5A). However, when they are given a conditioning pre-treatment at 37° C. prior to the 50° C. exposure, wild-type HSP104 and mutant hsp104 cells behave very differently. Although both exhibit induced tolerance, in the mutant this tolerance is extremely transient. Within 10 minutes of a shift to 50° C. a 1000-fold difference in the viability of mutant and wild-type cells is apparent. Thus, analysis of the hsp104 mutation has established two points: 1) hsp104 plays a vital role in induced thermotolerance 2) in the absence of hsp104 other factors in the cell can provide at least transient thermotolerance. The importance of hsp104 in providing tolerance to heat under different physiological conditions and at different stages in the life cycle was determined as was its role in protecting the organism from a variety of other types of stress.

EXAMPLE 2
The Amino Acid and Nucleotide Sequence of HSP104

The amino acid sequence of the hsp104 protein, deduced from the sequence of the HSP104 gene, is displayed in FIG. 1A–FIG. 1E. The sequence predicts a protein of 908 amino acids with a molecular weight of 102.1 kD. These results are in good agreement with a previous size estimate of 104 kd, which was based upon the electrophoretic behavior of the protein on SDS-polyacrylamide gels. The amino acids composition of the protein contains no tryptophan residues. A region of particularly high charge density is found between amino acids 410 and 530. This region is highly divergent between different members of the family and, because it is highly charged provides an immunodominant epitope. However, it is unlikely to be a region that is important for function of the protein.

Two putative ATP binding sites were identified in the hsp104 protein by comparison of the sequence with a previously defined adenine nucleotide-binding consensus sequence. These sequences, underlined in FIG. 1, occur between residues 212–284 and residues 614–685 of hsp104. Both sites contain a Gly-$X_4$-Gly-Lys-Thr sequence which has been shown, in other ATP-binding proteins, to form a glycine-rich flexible loop. This loop undergoes a conformational change which may be important in modulating the nucleotide's access to or affinity for the binding site (Walker, et al. 1985, Fry et al. 1985, 1986). The conserved lysine residue in this loop interacts with one of the phosphoryl groups of the bound MgATP. In addition to the loop consensus, in the appropriate position downstream, both sites contain a stretch of at least four hydrophobic amino acids terminated by an aspartate residue. X-ray crystallographic studies of ATP-binding pockets in other proteins suggest that these hydrophobic residues form a β-strand which flanks the triphosphate chain of the bound nucleotide and functions to minimize its hydrolysis by excluding water from the pocket. The aspartate at the end of the β-strand is likely to interact with the $Mg^{2+}$ of the bound MgATP (Walker et al. 1985, Fry et al. 1985, 1986). Other functional contacts come from different regions of the binding pocket in different proteins, but tend to be conserved in particular protein groups, presumably because they modulate the activity of the site. The first potential ATP-binding site in hsp104 most closely resembles the catalytic site in the β subunit of $F_1$-ATPase, while the second site most closely resembles the ATP binding site of myosin. Since one member of the hsp100 family (ClpA) is known to bind and hydrolyze ATP, it is likely that all proteins in the family do so. However, the proteins might also be able to bind and employ other nucleotides in their functions.

EXAMPLE 3
Functional Significant of the ATP Binding Sites

Figure 15A:
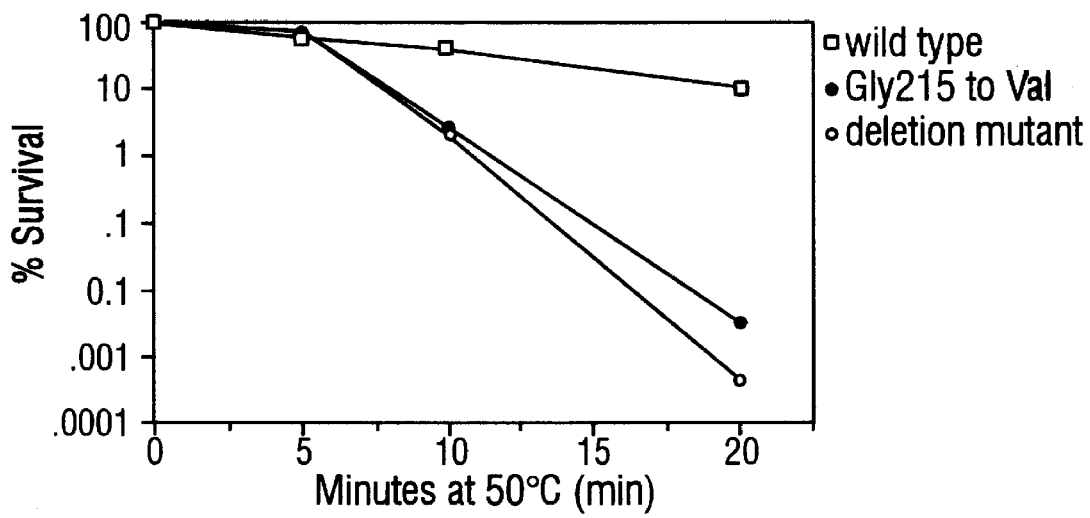
FIGS. 15A–F. HSP104 protein is inactivated by base substitutions.
Figure 15B:
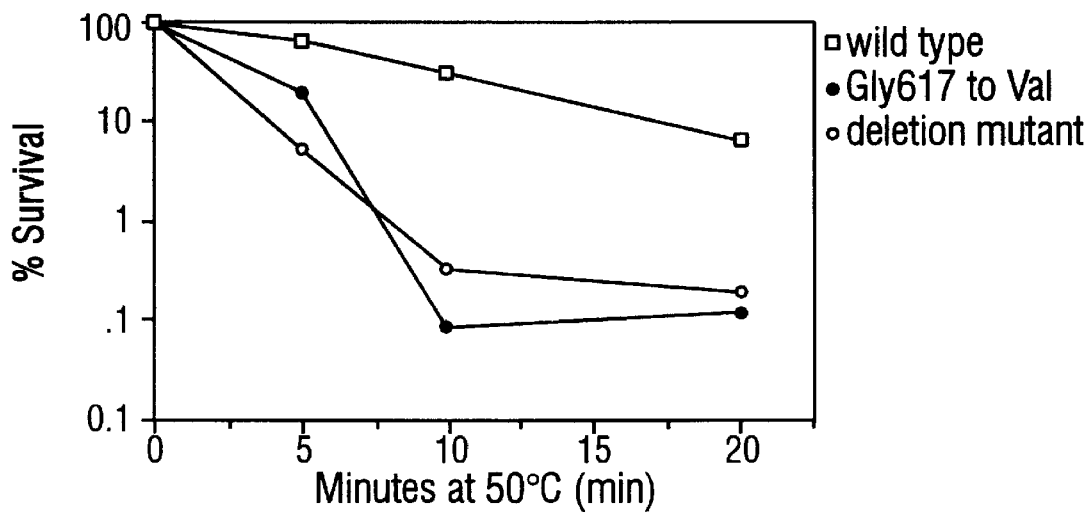

To determine if the putative ATP binding sites of hsp104 are essential for the function of the protein, site-directed mutations were introduced into the gene which resulted in single amino acid substitutions in each of the glycine-rich flexible loop sequences. Based upon published mutational analysis of other ATP binding pockets four substitutions were designed to inactivate the sites without disrupting the global structural stability of the protein. The second glycine in each of the putative flexible loops of hsp104 was replaced with valine and the conserved lysine in each loop was replaced with threonine. As shown in FIGS. 15A and F, the ability of the hsp104 protein to protect the cell from extreme heat was destroyed by all of these substitutions. In addition, by Western blotting, it was demonstrated that these substitutions do not affect the amount of hsp104 made, its intracellular proteolytic susceptibility, or its mobility on SDS-polyacrylamide gels. These results strongly suggest that the single amino acid substitutions which abolish the function of hsp104 do not do so indirectly by destabilizing the global structure of the protein or by increasing its sensitivity to proteolysis in vivo. Rather, it was concluded that they destroy the function of the protein by compromising its ability to use bound nucleotides.

Figure 15C:
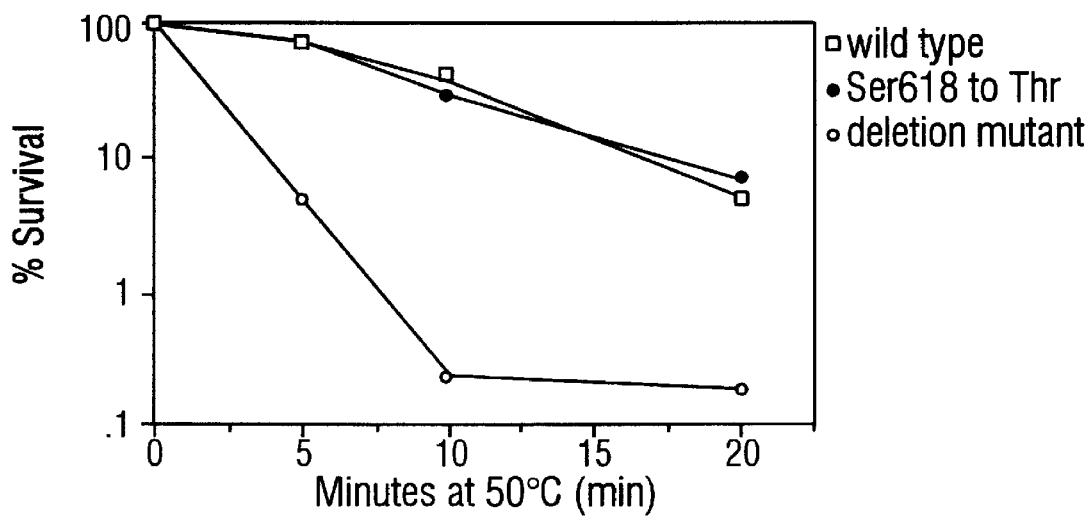
Figure 15D:
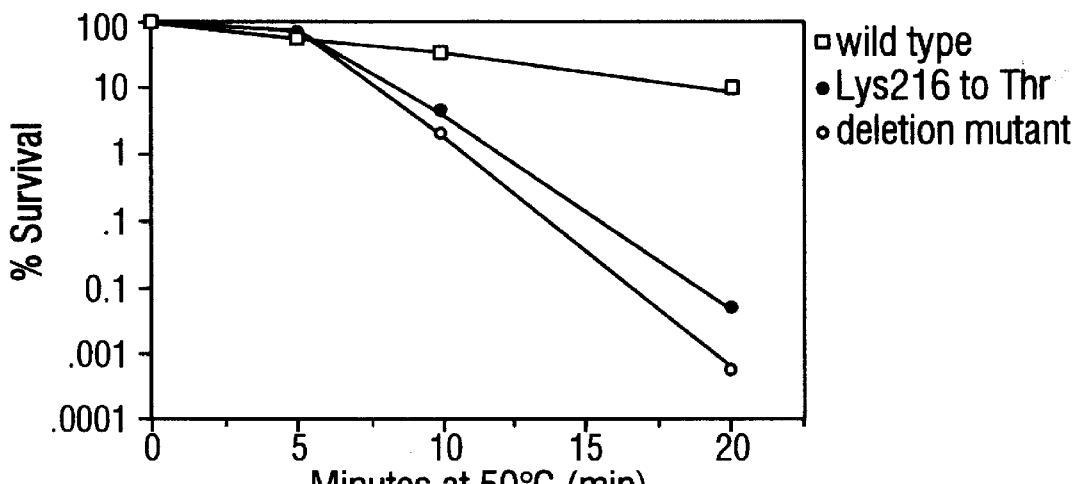
Figure 15E:
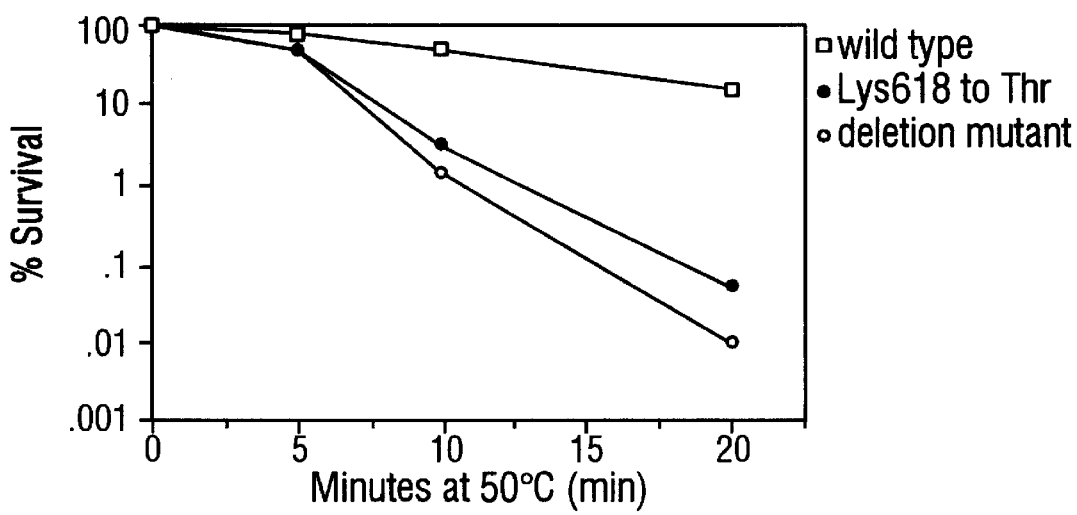
Figure 15F:
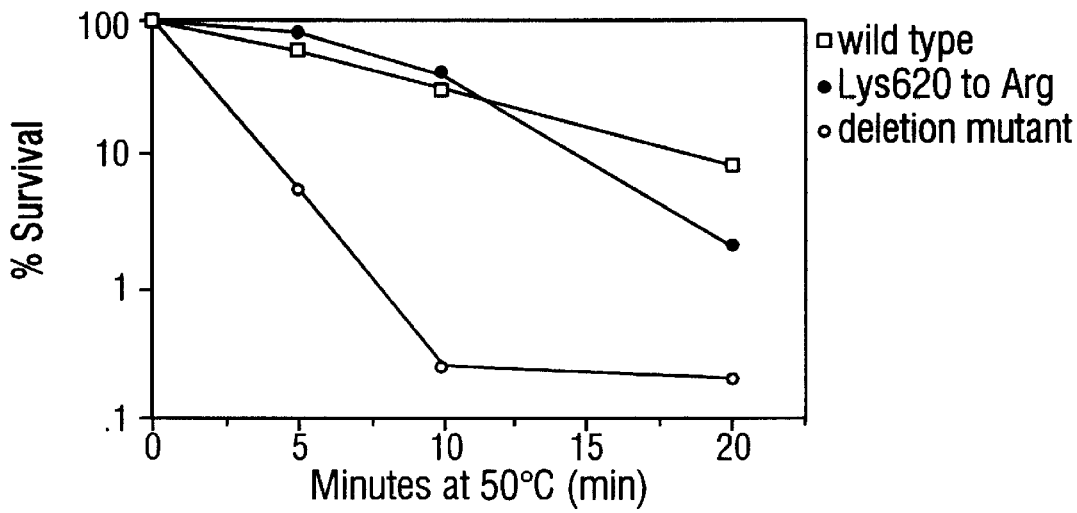

Two additional hsp104 variants were made with single amino acid substitutions in the second potential ATP binding site that were expected to be less deleterious to the function of the protein. First, Ser618 was changed to a threonine and, as shown in FIG. 15C, yeast cells expressing this variant of hsp104 exhibit no defect in induced thermotolerance. This finding is consistent with the fact that Ser618 occupies one of the non-conserved positions in the flexible loop of the second ATP binding site. Presumably the structure of this loop is not significantly perturbed by variation in the side chain of the residue in this position. Thermotolerance assays conducted on yeast cells expressing an hsp104 variant containing a Ser618→Pro substitution yielded similar results. Second, the conserved lysine at position 620 was replaced with arginine. This substitution has a very moderate effect on induced thermotolerance (FIG. 15F). The lysine at position 620 of the wild-type protein is postulated to be important in interacting with one of the phosphate groups of MgATP when it is bound to the second ATP binding site. Because arginine is also positively charged, it may be able to function in a manner similar to the wild-type residue, albeit somewhat less efficiently. The levels of these variants are similar to that of the wild-type protein based on Western analysis. Since mutations which are expected to compromise the nucleotide binding sites compromise hsp104 function in thermotolerance while those that are not expected to compromise nucleotide binding functions do not compromise, it was concluded that both conserved sites are in fact nucleotide binding sites.

EXAMPLE 4
The role of hsp104 in respiring cells

Yeast cells grow most rapidly in media containing glucose as the primary carbon source. In such media, respiratory metabolism is largely repressed and the cells grow primarily by fermentation (Lagunas, 1986; Kappelli, 1986). A role of hsp104 in thermotolerance was initially detected under such conditions. To determine if the protein would play an equally important role in respiring cells, cells were grown in media containing acetate as a sole carbon source, which forces them into respiratory metabolism. Mutant cells grew faster than the wild-type cells in acetate at normal temperatures. This phenomenon was observed in at least three different strain backgrounds. In rich acetate medium (YAc), the average generation time for wild-type cells of the W303 strain was 2.8 and for the mutant 2.3 hrs. (TABLE 1). In minimal media (Sac) a similar difference was observed (4.1 vs 3.7 hours). Mutant cells also grew to higher stationary-phase plateau densities in both media.

To determine if higher levels of hsp104 expression were accompanied by higher thermotolerance, log-phase cells growing in glucose or acetate at 25° C. were exposed at 50° C. for various lengths of time and survival was measured as colony forming ability. Basal levels of tolerance in glucose-grown cells are the same for mutant and wild-type (FIG. 5A, FIG. 5B, FIG. 5C, FIG. 6A, FIG. 6B, FIG. 6C, FIG. 6D, FIG. 6E and FIG. 6F). In contrast, in acetate-grown cells basal tolerance was much higher for wild-type cells (HSP104) than for the isogeneic (hsp104) strain, and the shapes of the killing curves were very different. In the early stages of exposure to 50° C., the difference in survival between mutant and wild-type cells was more than 100-fold. The shape of the killing curve for hsp104 cells grown in acetate closely resembles the curves for both mutant and wild-type cells grown in glucose.

Hsp104 is required for both basal and induced thermotolerance in respiring cells (FIG. 6A–FIG. 6F). Cells were grown at 25° C. to mid-log phase (2–3×10$^6$ cells/ml) in YP-Ac, S-Gal or S-Glu. Prior to exposure to 50° C., matched cultures were either maintained at 25° C. (FIG. 6A, FIG. 6B and FIG. 6C) or preincubated at 37° C. for 30 minutes (FIG. 6D, FIG. 6E and FIG. 6F). Following heating at 50° C., cells were transferred to ice, diluted in ice-cold YPDA, and immediately plated on YPDA.

Similar experiments were performed with cells growing in galactose, in which both fermentative and respiratory metabolism are active. In wild-type cells, hsp104 was constitutively expressed at a level that was a few fold higher than observed in glucose. Growth rates of mutant and wild-type cells were indistinguishable in galactose, but, as with acetate, basal thermotolerance was several-fold higher in wild-type cells. Thus, differences in basal thermotolerance correlate with differences in hsp104 expression rather than with differences between the growth rates of mutant and wild-type cells. The shape of the killing curve in the hsp104 mutant was similar to that of both mutant and wild-type in glucose. The conclusion from these observations is that the constitutive expression of hsp104 in respiring cells provides them with higher basal levels of thermotolerance.

To examine induced thermotolerance, log-phase cells growing on acetate, glucose or galactose were incubated at 37° C. for 30 minutes before being shifted to 50° C. A dramatic increase in survival was observed in both mutant and wild-type strains in all media (FIG. 6A, FIG. 6B, FIG. 6C, FIG. 6D, FIG. 6E and FIG. 6F). However, the tolerance of mutant cells was very transient. Within 20 minutes, a 100-fold difference in the survival of mutant and wild-type cells was apparent. Thus, hsp104 plays a crucial role in induced thermotolerance during both fermentative and respiratory metabolism.

EXAMPLE 5
Hsp104 in stationary phase cells and spores

In many organisms hsps are highly induced not only in response to heat, but also during the course of normal development. In Saccharomyces, hsp26, hsp82, hsp104, and one member of the hsp70 family are induced in two cell types that are naturally thermotolerant, in stationary phase cells and in spores (Scheberg-Frascino and Moustacchi, 1972; Plesset et al., 1987; Kurtz et al., 1986). The biological significance of developmental hsp inductions has been unclear. For example, deletion of the HSP26 or the HSP82 gene of yeast has no effect on sporulation itself nor on the long-term viability or thermotolerance of stationary phase cells and spores. The hsp104 mutation, however, has a profound effect on these cell types. They are severely compromised in their ability to withstand heat. Moreover, they do not withstand long term storage as well as wild-type cells, even at 4° C.

Hsp104 is induced in late stationary phase, right after the diauxic shift when glucose levels go down (FIG. 7A). During sporulation, hsp104 is strongly induced very early, prior to meiosis, and remains at a high level in mature spores (FIG. 7B).

Figure 11A:
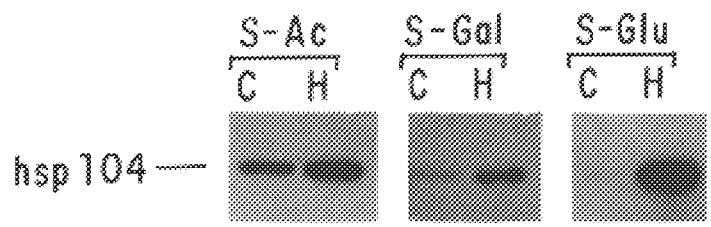
FIGS. 11A–11C. Expression of hsp104 under different conditions.
Figure 11B:
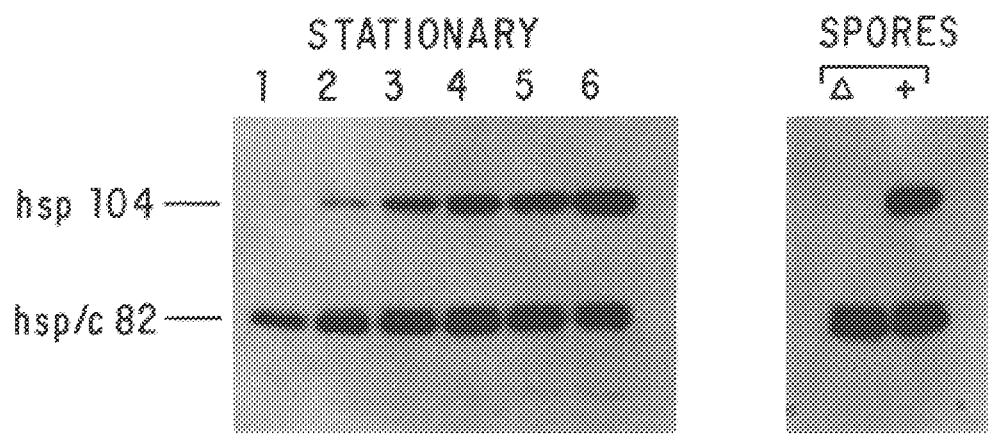
Figure 11C:
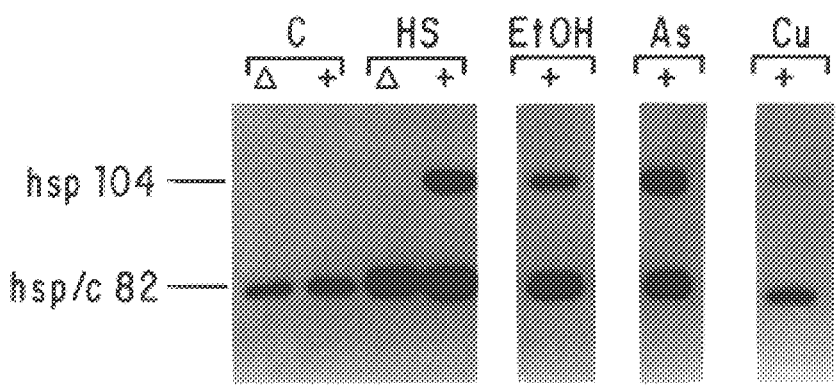

Expression of hsp104 under different conditions is shown in FIGS. 11A and 11C. To provide a basis of comparison, the blot was also reacted with an antibody that recognizes both the hsp82 and hsc82 proteins. Hsp82 migrates just above hsc82 and its induction parallels that of hsp104. Total cellular proteins from equal numbers of cells were prepared by glass bead lysis in ethanol. After electrophoretic separation on 7.5% SDS-polyacrylamide (PAGE) gels, proteins were transferred to nylon membranes, stained with Coomassie blue to ensure equal loading, and reacted with a rabbit antiserum specific for hsp104. Immune complexes were visualized by reaction with [$^{125}$I] labeled-protein A.

(FIG. 11A) wild-type cells (+) of strain W303 (Rothman, 1989), were grown at 25° C. to mid-log phase in liquid medium: SGlu (2% glucose, 0.67% bacto-yeast nitrogen base without amino acids and the appropriate supplements), SGal (same as Sglu but replacing glucose with 2% galactose) and Sac (replacing glucose with 1% potassium acetate). The cultures were divided and maintained at 25° C. or heat-shocked at 39° C. for 30 minutes.

(FIG. 11B) Left, wild-type cells were grown from log-phase to late stationary phase in YPDA. Proteins were harvested at different culture densities: 2×10$^7$ cell/ml (1), 7.3×10$^7$ cell/ml (2), 1×10$^8$ cell/ml (3), 1.5×10$^8$ cell/ml (4), 1.8×10$^8$ cell/ml (5), and 2.5×10$^8$ cell/ml (6) and adjusted to represent equal numbers of cells.

Right, mutant (Δ) and wild-type cells (+) were sporulated in liquid culture (1% potassium acetate) (Kurtz et al., 1986). After 4 days asci were digested with 0.6 mg/ml of zymolyase 20T and mature spores were collected in a percoll gradient as described (Esposito et al., 1991).

(FIG. 11C) mutant (Δ) and wild-type cells (+) were grown to mid-log phase in YPDA and maintained at 25° C. or exposed to 37° C. for 30 minutes, 6% ethanol for 1 hour (EtOH), 0.75 mM sodium arsenite for 1 hour (As) or 11 mM copper sulphate for 30 minutes (Cu).

To examine thermotolerance in stationary phase, cells were grown at 25° C. in glucose-containing medium to plateau density and maintained with aeration for an additional 24 hours. Mutant (hsp104) and wild-type cells (HSP104) were then exposed directly to 50° C. for various times prior to plating (FIG. 6A, FIG. 6B, FIG. 6C, FIG. 6D, FIG. 6E and FIG. 6F). Stationary-phase cells were far more thermotolerant than log-phase cells that had been grown in acetate, glucose or galactose. In fact, wild-type cells grown to stationary-phase at 25° C. were as tolerant of heat as log-phase cells that had been given a conditioning pre-treatment at 37° C.

The thermotolerance of mutant cells in stationary phase was much lower than that of wild-type cells. After 60 minutes at 50° C., a 100-fold difference in survival was observed (FIG. 6A, FIG. 6B, FIG. 6C, FIG. 6D, FIG. 6E and FIG. 6F). As with log-phase cells, this effect was able to be rescued by a plasmid carrying the HSP104 gene on a centromeric vector, confirming that the difference between wild-type and mutant cells is due to the absence of the HSP104 protein. Thus, HSP104 plays a vital role in protecting stationary phase cells from high temperatures. However, mutant stationary phase cells were more tolerant than mutant log-phase cells. Thus, other factors can provide at least partial tolerance in the absence of hsp104.

Because HSP104 is induced early in sporulation, it was possible that the HSP104 mutation had an effect on the sporulation process itself. Homozygous mutant diploids sporulated at nearly the same rate as wild-type diploids and to the same extent. Levels of sporulation varied between experiments (60% to 75%) but, within any given experiment, mutant and wild-type cells behaved similarly. Furthermore, the wild-type spores and the mutant spores germinated at similar rates and showed equally high levels of viability when dissected at 25° C.

As expected, wild-type spores showed very high levels of thermotolerance when exposed to 51° C. The mutant was much more sensitive. Within 90 minutes, the viability of mutant spores was 100 fold less than that of wild-type spores (FIG. 11B). Thus, although spores may have many mechanisms for providing protection against heat, the role of hsp104 remains crucial.

Another difference between mutant and wild-type cells became apparent during long-term maintenance of the cells. For stationary-phase cells, viability was maintained at 25° for many days with no apparent difference between the mutant and wild-type. However, when cells began to die, after about 10 days, mutant cells died 10 to 15 times more rapidly than wild-type cells (TABLE 2). The ability of spores to tolerate long-term storage is much greater than that of stationary-phase cells. However, even during storage at 4° C., a difference was detected between mutant and wild-type spores. After 6 months, no loss of viability was detected in wild-type spores. In the same period, 50 to 75% of mutant spores died.

EXAMPLE 6
Function of HSP104 as a Protection Against Heat

Extreme temperatures (50°–55° C.) kill cells in a matter of minutes. At less severe temperatures (e.g., 44° C.), cells survive for many hours. Whether the lethal lesions produced at the less severe temperatures are the same as those occurring during rapid killing at extreme temperatures, was not known. Mutant (hsp104) and wild-type cells were grown to log-phase, pre-treated at 37° C. for 30 minutes and shifted to 44° C. The cells differed only in that mutant cells were not capable of producing functional heat shock proteins 104. They were maintained at this temperature with aeration for 4, 8, 16, 24 or 48 hours. During the course of the subsequent observations the survival of wild-type cells varied from 71% after 3 hours to 1% after 24 hours. At nearly every time point, the viability of wild-type cells was 10-fold greater than that of mutant cells. Although these differences in killing are not as extreme as they are at more severe temperatures, it is clear that the majority of cells in the culture depend upon hsp104 for survival at 44° C.

The role of hsp104 was also tested under very extreme heat. At 58° C., wild-type cells lose viability very rapidly, but mutant cells lose viability even more rapidly. After two minutes of exposure, 1% of wild-type cells survived but only 0.01% of mutant cells survived.

EXAMPLE 7
The Role of hsp104 in Other Forms of Stress; Ethanol

Mutation of the HSP104 gene affects both ethanol-induced tolerance to heat and heat-induced tolerance to ethanol.

Under the culture conditions disclosed herein the strongest inductions of hsp under alcohol as a stress were observed after 1 hour in 6% ethanol. To determine whether the hsp104 protein that is induced by ethanol is capable of providing tolerance to heat, log-phase cells were incubated with or without 6% ethanol at 25° C. for 1 hour and were then exposed to 50° C. Although pre-treatments with ethanol induced thermotolerance in both mutant and wild-type cells, the tolerance of mutant cells was 100-fold less than that of wild-type cells (FIG. 8A). Thus, the thermotolerance that is induced by ethanol is dependent upon hsp104 to approximately the same extent as the thermotolerance that is induced by mild heat treatments. To examine heat-induced tolerance to ethanol, log-phase cells growing in glucose were exposed to toxic concentrations of ethanol (20%), with or without a pre-heat treatment at 37° C. (FIG. 8B). Without the pre-treatment, cells were killed extremely rapidly, with no appreciable difference between mutant and wild-type cells. With the pre-treatment, wild-type cells showed high levels of tolerance to ethanol. The hsp104 mutant showed none. Clearly, hsp104 plays a vital role in protecting cells against killing by ethanol.

Specific conditions employed in these experiments were as follows:

(A) Cells were incubated with or without 6% ethanol at 25° C. for 1 hour. Equal portions of the culture were exposed to 50° C. for various lengths of time and cell survival was determined by plating cells on YPDA.

(B) Cells were maintained at 25° C. or incubated at 37° C. for 30 minutes before being exposed to 20% ethanol. Cells were washed to remove the ethanol before being plated to measure colony forming ability.

EXAMPLE 8
The Role of hsp104 in Other Forms of Stress; Heavy Metal Ions

An inducer of the heat-shock response in a wide variety of organisms is sodium arsenite. In yeast cells, a previous report had indicated that arsenite does not induce most hsps in S. cerevisiae (Change et al., 1989). However, after 60 minutes of incubation in 0.75 Mm arsenite, hsp104 was induced to a level comparable to its induction by ethanol or heat-shock (FIG. 9A, FIG. 9B and FIG. 9C). In fact, all of the hsps were induced by this treatment, as determined by the incorporation of radio-labelled amino acids. To determine if the proteins induced by arsenite were capable of providing thermotolerance, log-phase cells were incubated in the presence or absence of 0.75 mM arsenite for 60 minutes. The arsenite pre-treatments greatly increase thermotolerance in both mutant and wild-type cells. However tolerance in the wild-type was 100-fold greater than in the mutant. Thus, when induced by arsenite, hsp104 is in a state that is fully capable of functioning in thermotolerance.

To further examine the role of hsp104 in protecting against arsenite, the concentration of arsenite required to kill 99.9% of the cells in less than 3 hours was determined. Cells were then exposed to this concentration of arsenite (100 mM) for 1, 2 or 4 hours, with or without a 37° C. pretreatment. Surprisingly, a five-fold difference was seen in the survival of mutant and wild-type cells in arsenite, even without a pre-treatment (FIG. 9A, FIG. 9B and FIG. 9C). The most likely explanation is that hsp104 protein, induced during the course of the incubation, provided partial tolerance as the incubation continued. Pre-treatments at 37° C. induced high levels of tolerance to arsenite. Mutant cells died more rapidly than wild-type cells at every time point, but the effect was relatively small, only 2 to 3 fold.

The effects of arsenite pre-treatments on arsenite tolerance were examined (FIG. 9B and FIG. 9C). In cultures that did not receive the pre-treatment the mutant died faster than the wild-type. With an arsenite pre-treatment, tolerance was increased. Mutant cells died more rapidly than wild-type cells. The differences between mutant and wild-type cells in this case were on the order of 10 fold. Thus, hsp104 plays an important role in protecting cells against killing by arsenite.

The conditions employed in this experiment were as follows:

(A) Cells maintained at 25° C. in the presence or absence of 0.75 mM arsenite for 30 minutes were washed, resuspended in fresh media, and exposed to 50° C.

(B) Cells were maintained at 25° C. or incubated at 37° C. for 30 minutes. Arsenite was added to 100 mM arsenite and cultures were maintained with vigorous aeration. At various times, cells were washed to remove the arsenite before being plated to measure colony forming capacity.

(C) Preincubated with or without 0.75 mM arsenite for 30 minutes at 25° C. Cells were then killed using 100 mM arsenite.

Finally, tolerance to copper and cadmium was examined. First the concentration of copper required to induce a substantial quantity of hsp104 was determined. A very slight induction was observed at 5 mM and a more substantial induction at 11 Mm. When cells were treated with 11 mM copper for one hour, a significant loss of colony forming ability was observed. The treatment, however, produced a increase in the ability of wild-type cells to tolerate heat. Because little or no thermotolerance was induced in the mutant, the hsp104 protein induced by copper is highly likely functional. On the other hand, this protein is not able to protect cells against killing by copper. Thus, although the protein has broadly protective functions, it does not protect cells against all stresses which induce it.

EXAMPLE 9
Hsp104 is a Member of the ClpA Protein Family

A search of the GENBANK data base revealed that hsp104 belongs to a family of proteins known as the ClpA family (Gottesman et al. 1989, 1990). These proteins share extensive blocks of homology of more than 200 amino acids, centered around two ATP binding domains. The only member of this group with a characterized function is the product of the E. coli ClpA gene itself, which encodes the regulatory subunit of the ATP-dependent Clp protease. E. coli contains another gene, ClpB, which has 63% amino acid similarity to ClpA overall and 85% similarity within the two large conserved regions (Gottesman et al. 1989, 1990). Other members of the ClpA family were identified fortuitously by noting sequence homology to previously cloned genes in the prokaryotes *Bacteriodes nodosus, Rhodospeudomonas blastica, Streptococcus mutans*, and in the eukaryotes *Trypanosoma brucei* and tomato (Gottesman et al. 1989, 1990). The sequence homologies reported by Gottesman and co-workers suggest that these proteins fall into two subfamilies, with most of them showing a higher degree of similarity to ClpB than to ClpA. Prior to the present invention, there was no indication that any of these proteins was inducible by heat. Indeed, studies of the ClpA protein suggested that it was not heat-induced. Furthermore, there was no indication in the literature that any of these proteins would be able to protect cells against stress.

Figure 2A:
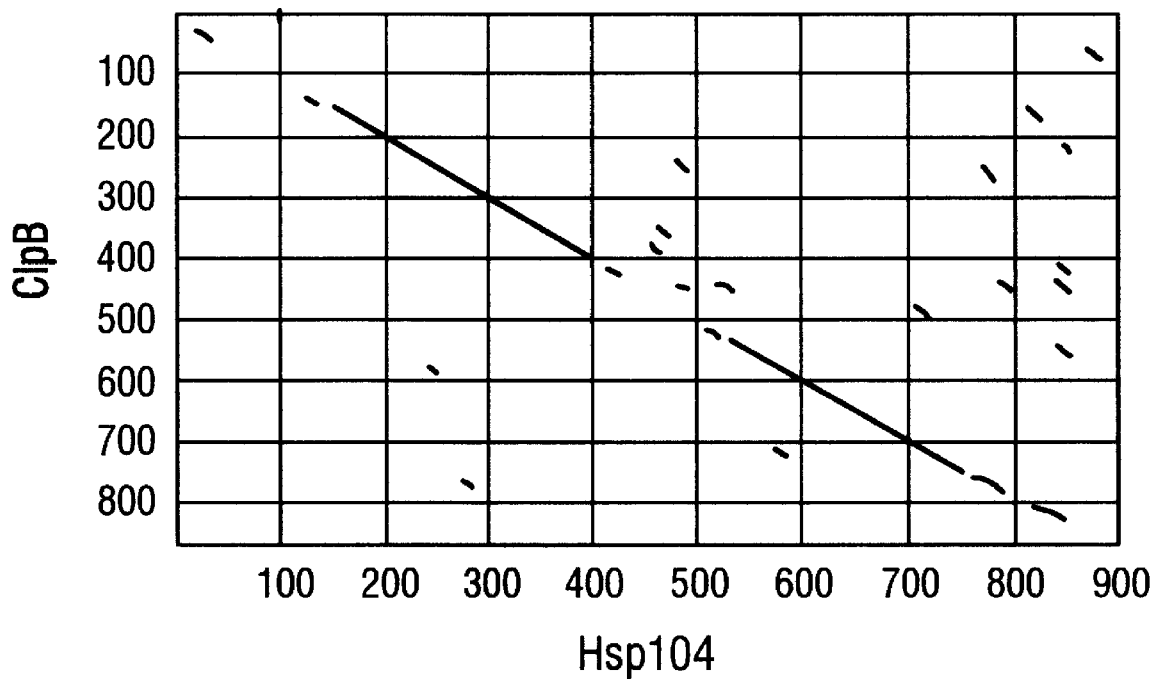
FIGS. 2A, and 2B and FIG. 2C. Comparisons of ClpA (FIG. 2B and FIG. 2C) and ClpB (FIG. 2A and FIG. 2C) with hsp104.
Figure 2B:
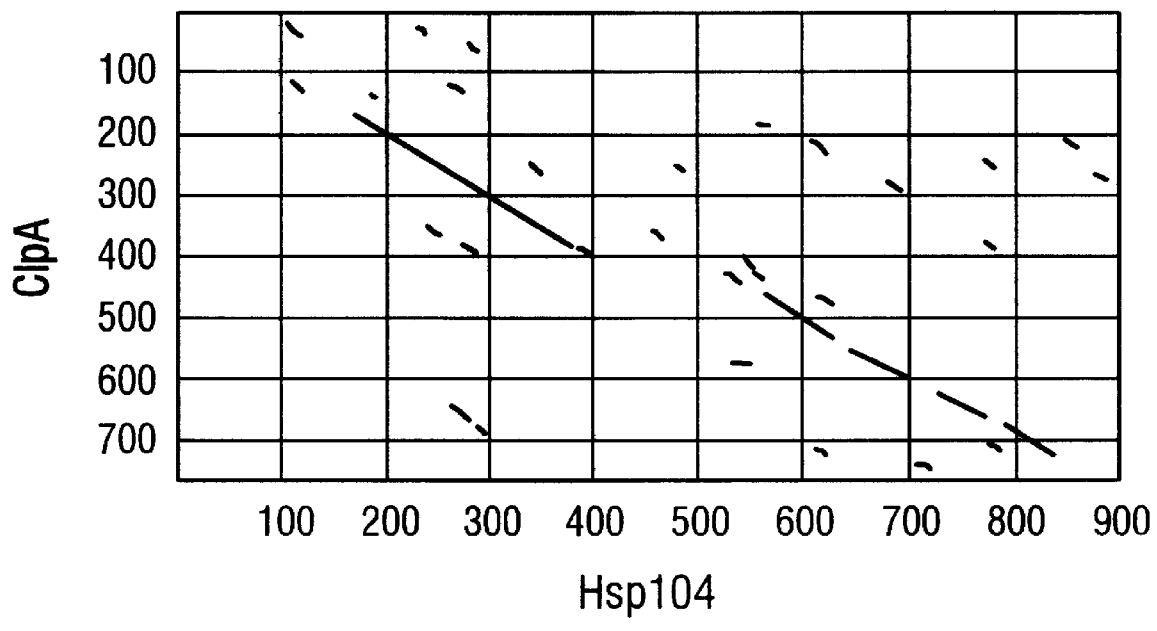
Figure 2C:
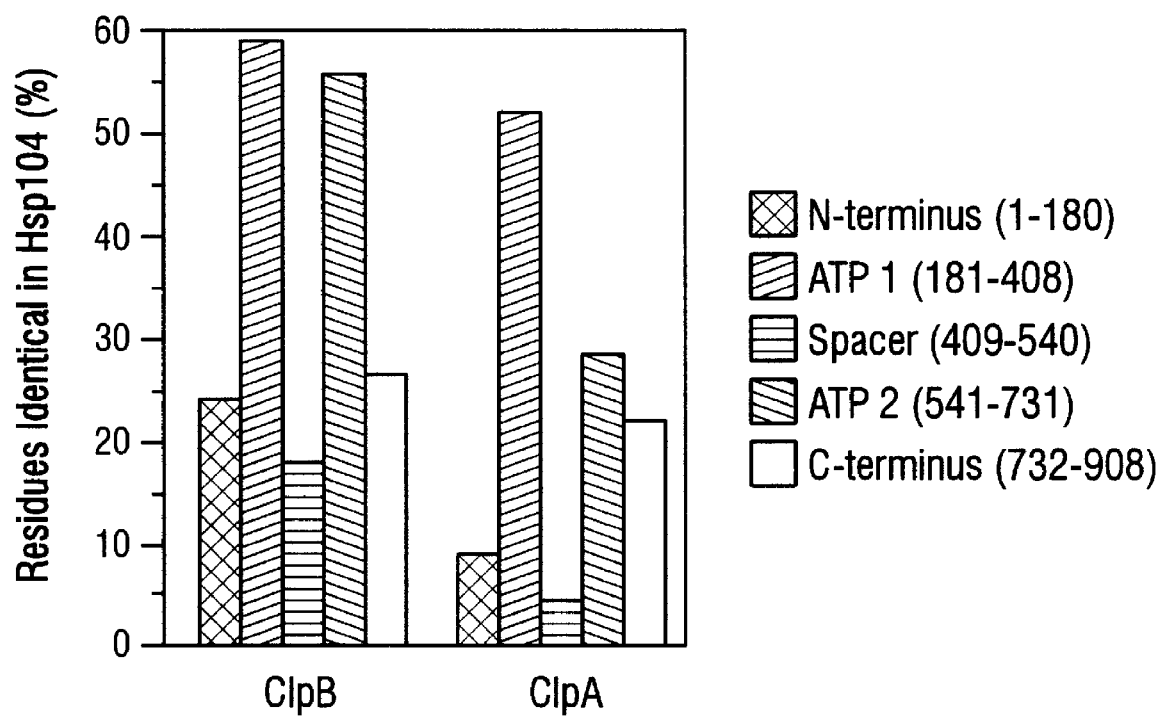
Figure 3A:
FIGS. 3A–3E. Maps of HSP104 clones and constructs.
Figure 3B:
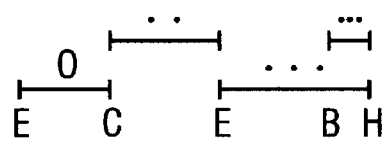
Figure 3C:
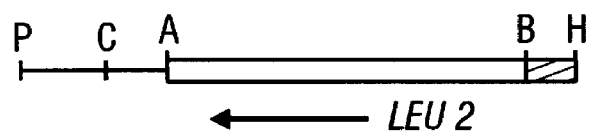
Figure 3D:
Figure 3E:
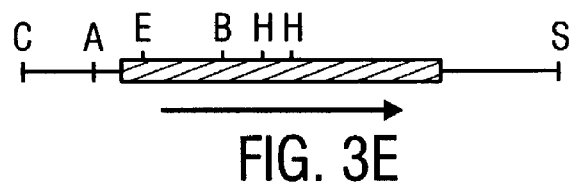

Hsp104 shows greater homology with the ClpB protein than with ClpA. Matrix plots comparing ClpA and ClpB with hsp104 are shown in FIG. 2A and FIG. 2B. Hsp104 and the ClpB protein are collinear and homologous throughout. The alignments distinguish five regions with varying degrees of homology. In region 1 (hsp104 residues 1–180) the yeast protein shows 23% identity with the ClpB protein and 9% with the ClpA protein. In region 2 (amino acids 181–408, and including the first ATP binding consensus sequence) the yeast protein is 59% identical to ClpB and 51% identical to ClpA. Region 3 (residues 409–540), termed the spacer region by Gottesman et al. 1989, 1990) is largely missing in ClpA but exhibits 18% identity between hsp104 and ClpB. Interestingly, this region corresponds to the highly charged domain of hsp104. Region 4 of hsp104 (amino acids 541–731, and including the second ATP binding consensus sequence) is 55% identical to the corresponding region of ClpB, but only 28% identical to that of ClpA. In region 5, the carboxy terminal portion of the protein (residues 732–908), the yeast hsp104 shares 25% and 22% identity with the ClpB and ClpA proteins respectively.

As pointed out by Gottesman and co-workers, the two putative ATP binding sites in the Clp protein family are highly conserved between species and distinctly different from each other. Gottesman noted that the first site is most similar to the catalytic site of $\beta$-F1ATPase. As an aspect of the present invention, it was noted that the second site most closely resembles the ATP binding site of myosin.

EXAMPLE 10
Biochemical Characterization of Hsp104 and the Clp Proteins

Although the biochemical properties of the ClpB protein have not been examined, the ClpA protein has been studied in detail. In developing the present invention, it was noted that the yeast hsp104 protein shares certain physical properties with ClpA. Both proteins precipitate in ammonium sulfate at 40 to 60% saturation, which is common to many polypeptides in the cell. More significantly, the two proteins bind to the same chromatographic resins and elute similarly from both anionic and cationic exchangers. They elute from phosphocellulose at different concentrations, perhaps due to the absence of the negatively charged, middle domain in the ClpA protein which is not present in hsp104.

Another property the hsp104 and ClpA proteins may share is an ability to interact with other proteins to form large oligomeric complexes. The ClpA protein oligomerizes and forms a complex with the proteolytic subunit of the Clp protease, the 12 subunit ClpP complex. The complete, ATP-dependent proteolytic complex has a molecular weight of more than 500 kd. When heat-shocked yeast cells were lysed by enzymatic digestion of the cell wall followed by gentle vortexing with glass beads, approximately ¼ of the hsp104 protein was released into the supernatant and the remainder of the protein was found in the pelleted debris following low speed centrifugation (12,000×g, 10 min, 4° C.) Because the primary function of hsp104 is to protect cells from extreme physical stresses such as high temperatures and high concentrations of ethanol, given the very gentle lysis conditions used, it seems unlikely that this pelleted material is simply heat-denatured. Rather, it almost certainly reflects the ability of hsp104 to interact with other proteins. Unlike the ClpA protein, however, which is proposed to interact only with the ClpP protein, we believe that the hsp104 protein and other members of the hsp100 family interact with many proteins in the cell in order to protect them from damage by stress or to repair damage done to the proteins and other protein-containing structures by the stress. The evidence for this assertion comes from several different experiments.

First, the phenotype of the hsp104 mutation suggests it has a very general protective role. Second, immunofluorescent localization suggests it functions throughout the cell. Third, electron microscopy demonstrates that the protein is required to prevent massive aggregation and denaturation of cellular components throughout the cell. Fourth, the phenotype of the hsp104 deletion can be partially repressed by over expression of hsp70. This protein is known to function in a variety of protein folding and unfolding processes. This experiment suggests that the two proteins have partially overlapping functions. However, because the hsp70 protein is only partially effective in restoring thermotolerance, it appears that the hsp104 function is more highly specialized for protecting cells from extreme stress. Fifth, the protein is required for rapid recovery of RNA processing after heat shock. It is very unlikely that this function reflects proteolytic activity. We believe the restoration of RNA processing represents one of many biological processes which the protein is able to enhance. The enhancement is envisioned to operate through a very general role in protecting cellular components from denaturation or in helping to repair denatured components before they have formed aggregates or are irreversibly destroyed.

Figure 13A:
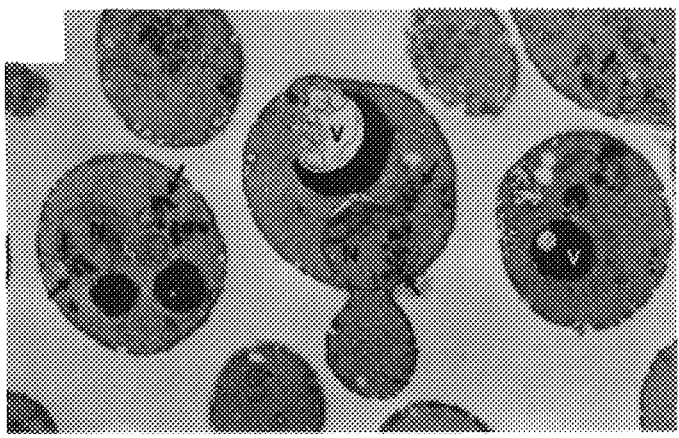
FIGS. 13A–13C. Electron microscopy of FIG. 13A) mutant cells at high temperature.
Figure 13B:
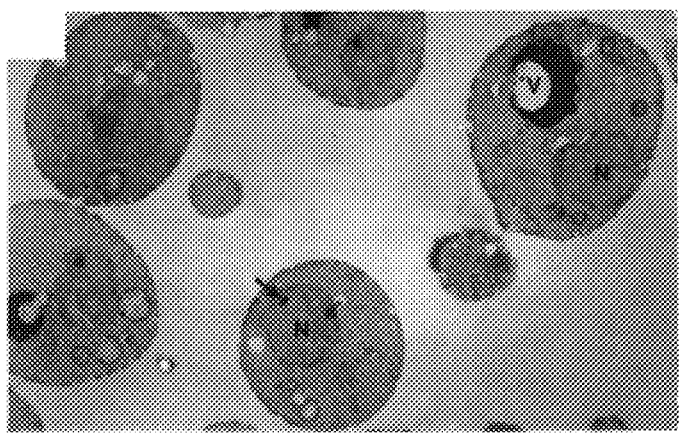
Figure 13C:
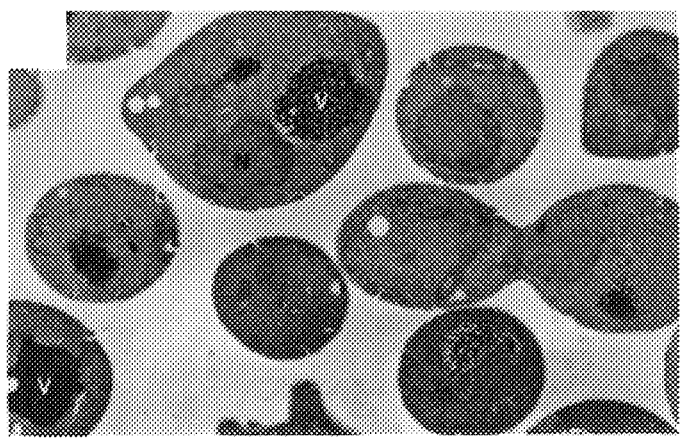

As illustrated in FIG. 13A, FIG. 13B and FIG. 13C, (electron micrographs), massive aggregation of cellular components occurs at high temperatures in (FIG. 13A) mutant cells but not (FIG. 13B) in wild-type cells nor (FIG. 13C) in mutant cells at normal temperatures. To obtain this evidence of the action of ths hsp104, yeast cells were raised gradually to 43° C. by increasing the temperature in stepwise fashion from 37° C., in 2° C. increments every 30 mintues. A portion of the culture was plated to ensure that cells still retained high levels of viability. Cells were fixed for electron microscopy by standard methods, sectioned, and stained with uranyl acetate. Similar results were obtained when cells were shifted directly from 25° C. to 38.5° C.

EXAMPLE 11
Microscopic Analysis of Mutant and Wild-Type Cells

Figures 12A, 12B:
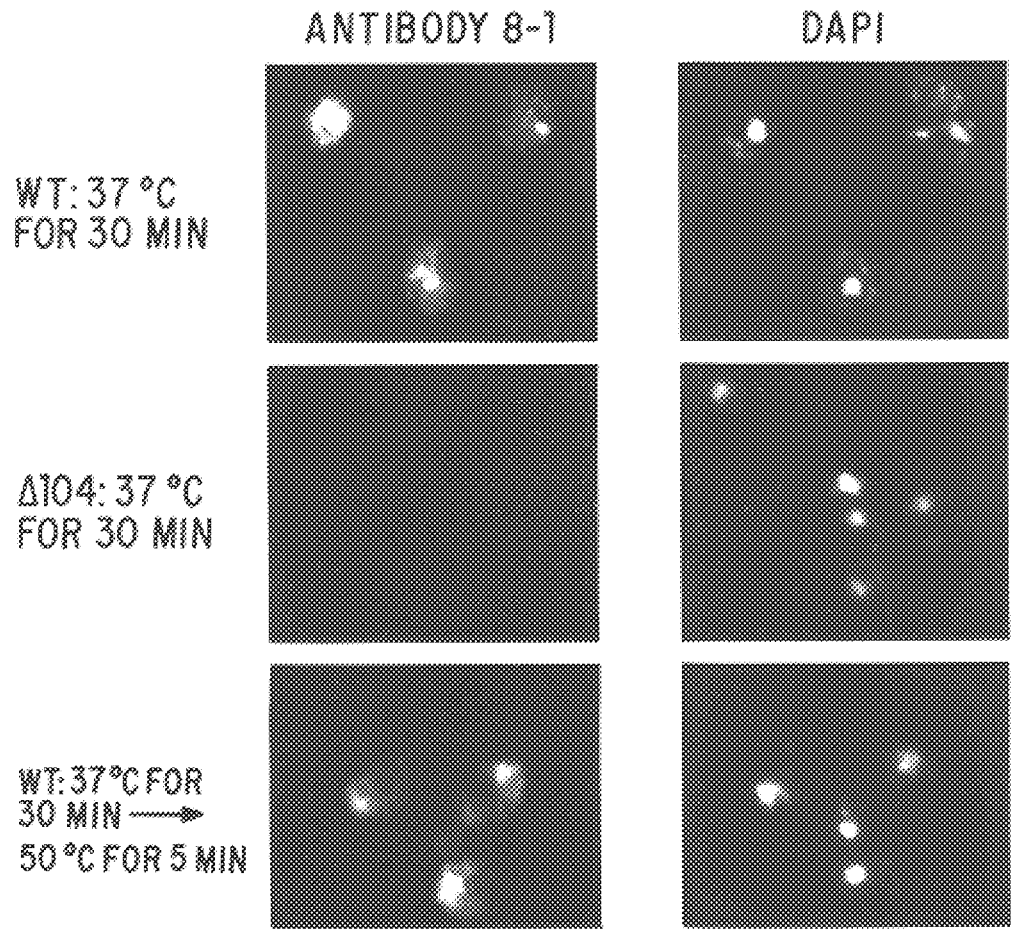
FIG. 12A and FIG. 12B. Cellular distribution of hsp104 after moderate heat shock temperatures.

The intracellular localization of hsp104 was determined by immunofluorescent analysis with antibodies raised against the carboxy terminal region of the protein. At moderate heat shock temperatures, hsp104 is distributed throughout the cell, but its staining is not diffuse (FIG. 12A and FIG. 12B). Rather, it appears to be present in many small points of high concentration both in the nucleus and the cytoplasm. The specificity of the staining for hsp104 was demonstrated by the absence of staining in an hsp104 deletion strain. The staining changes somewhat when cells are shifted to the higher temperatures at which tolerance is observed. In particular, the staining in the nucleus remains intense, but the distribution is noticeably shifted.

Electron microscopy of mutant and wild-type cells provides an important clue to the function of the protein. At normal temperatures, mutant and wild-type cells have indistinguishable morphologies. When the cells are exposed to high temperatures, however, they are very different. Mutant cells show massive accumulation of aggregated cellular components. These are most prominent in the nucleus but are present in the cytoplasm as well. Wild-type cells contain similar aggregates but at a very greatly reduced frequency. This indicates that a major function of the hsp104 protein is to prevent the accumulation of aggregated, and presumably, non-functional cellular components at high temperature. Presumably, the protein either prevents intracellular structures from denaturing under conditions of stress or helps to repair structures which have been denatured or partially denatured. It seems to share certain functions with previously identified chaperone proteins, except that it is more specialized to protect cells under conditions of stress.

EXAMPLE 12
ClpB is Heat-Inducible

Although the catalytic subunit of the Clp protease, ClpP, is heat-inducible (Kroh and Simon, 1990), the ClpA protein has been reported not to be (Katayama et al., 1988). Because of the heat-related functions of HSP104 in yeast cells and because it shares greater homology with ClpB then ClpA, the heat inducibility of the ClpB gene was examined. The ClpB message is strongly heat-inducible.

Antisera produced against a conserved peptide, amino acids 209–224 of the yeast sequence, was reacted with electrophoretically separated proteins from a 43° C., heat-shocked *E. coli* lysate. Two heat-inducible proteins did not react with the pre-immune serum, but strongly reacted with the antiserum. These proteins migrated on gels with apparent molecular weights of approximately 100 kD and 80 Kd. The larger protein is of the size expected for the ClpB protein.

EXAMPLE 13
Cross Hybridization of HSP104 Sequences with Human and Drosophila mRNAs Polyclonal antibodies raised against the mammalian 110 kD protein do not cross react with the yeast protein and those raised against the yeast hsp104 protein do not cross react with any non-fungal species. This is likely to be because the most divergent domain in hsp104 is also the most highly charged and is immunodominant. Polyclonal antibodies raised against the yeast hsp82 protein, which also contains a highly charged, divergent region, do not cross hybridize with the mammalian hsp90 protein although these proteins share 60% amino-acid identity overall. The hsp82 and hsp90 genes, however, do cross-hybridize at low stringency.

To determine if homologs of the yeast HSP104 gene were heat-inducible in other eukaryotic cells, radiolabelled probes from the amino-terminal and the carboxy-terminal halves of the coding sequence were hybridized at low stringency to total cellular RNAs from control and heat-shocked cells of widely divergent species. As may be seen in FIG. 14C, the amino-terminal half of the yeast gene hybridized to a heat-inducible RNA of approximately 3.2 kb from HeLa cells, exactly the size expected for a protein of 110 Kd. An identical band of hybridization was obtained using the carboxy-terminal half of the gene as a probe. A more diffuse band of hybridization was observed at the position of the large ribosomal RNA. Hybridization at this position did not change with heat-shock and provided a convenient means of standardizing the blot. That both the amino-terminal and the carboxy-terminal HSP104 probes hybridized to heat-inducible RNAs of the correct size strongly suggests that 1) human cells carry a gene related to the yeast HSP104 gene and 2) both the sequence and the regulation of this gene have been highly conserved.

Figure 14A:
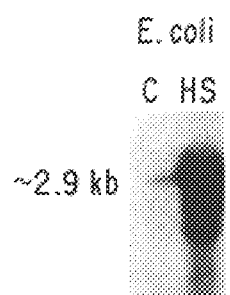
FIGS. 14A–14F.
Figure 14B:
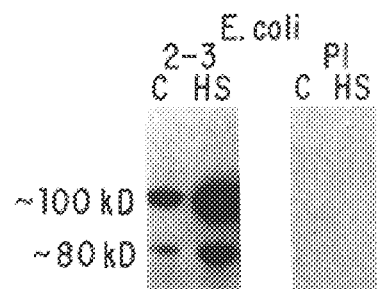
Figure 14C:
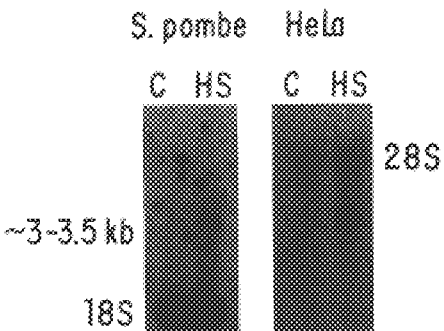
Figure 14D:
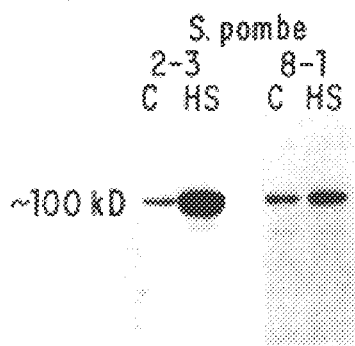
Figure 14E:
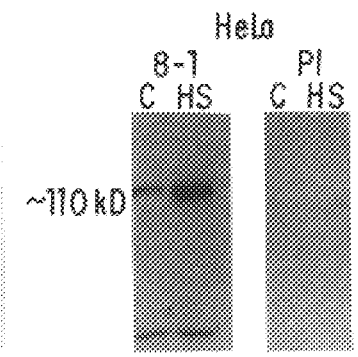
Figure 14F:
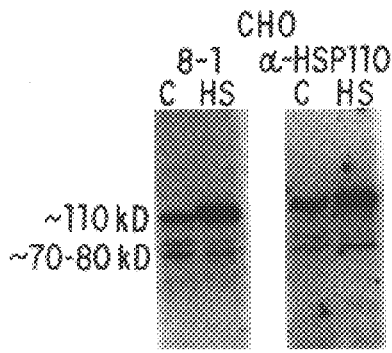

To confirm that HeLa cells produced a homologous, heat-inducible protein, antibodies raised against yeast hsp104 peptides were reacted with proteins from HeLa cells. As shown in FIG. 14E, an antibody raised against the C-terminal 15 residues of hsp104 cross reacts with two high molecular weight HeLa proteins. One of these proteins is strongly heat inducible and the other is mildly heat inducible. Similarly, two strongly cross reacting proteins are observed in electrophoretically separated lysates from Chinese hamster ovary cells. Both are approximately 100 kD in size and both a heat-inducible and a constitutive species are observed. As previously reported, hsp100 concentrates in nucleoli. The intense subnuclear (nucleoi) staining of the yeast protein provides an additional criteria for functional homology between the yeast and mammalian proteins.

Drosophila melanogaster is one of the few eukaryotic organisms that does not appear to produce a protein in the 100 kd size class. Indeed, the fact that investigations of the heat-shock response began in Drosophila probably accounts for the relative lack of interest in this particular heat-shock protein until the current series of investigations. The Clp gene of E. coli cross hybridizes with DNA from Drosophila cells at low stringency. To examine the transcriptional behavior of the putative Drosophila homolog, yeast probes were hybridized at low stringency to RNAs from control and heat-shocked cells. Two heat-inducible bands of hybridization were observed, one of the size expected to encode a protein of 100 kd, the other less than half that size. Both bands were retained by oligo-dT cellulose, indicating that they are both polyadenylated. However, only the smaller RNA was found on polysomes in appreciable quantities. Using anti-peptide antibodies which cross react with the S. cerevisiae, S. pombe, HeLa, and Chinese hamster ovary cells, no definite bands of cross reactivity formed with Drosophila proteins. Thus, although Drosophila cells contain a homologous gene, it appears to have undergone some change that severely reduces its expression during heat shock.

With several organisms, we have also noted the production of smaller RNAs which hybridize specifically with the hsp104 probe. This suggests that smaller related proteins might also have stress-protective functions. For example, it is possible that individual nucleotides binding domains relates to the hsp100 family by amino acid homology could function themselves in stress protection, or in regulating the function and/or activity of the larger hsp100 family member.

EXAMPLE 14
Detection of a Candidate Inhibitor Substance

In still further embodiments, the present invention concerns a method for identifying new inhibitors of stress protector proteins which may be termed "candidate substances." It is contemplated that this screening technique will prove useful in the general identification of any compounds that will serve the purpose of inhibiting the stress protector protein. It is further contemplated that useful compounds in this regard will in no way be limited to proteinaceous or peptidyl compounds.

Thus, in these embodiments, the present invention is directed to a method for determining the ability of a candidate substance to inhibit a stress protector protein, the method including generally the steps of:

(a) obtaining a composition comprising a cell capable of responding to stress;

(b) admixing a candidate substance with the stress protector protein composition; and (c) determining the subsequent ability of the cell to produce active stress protector protein and survive in the presence of the candidate substance.

Two broadly defined methods for identifying a substance which will interfere with the stress protector proteins function are as follows. The first assay depends upon the ability to prepare a stress protein composition in a relative purified form, for example, by ammonium sulfate precipitation and ion exchange chromatography. (See also Materials and Methods herein.) This is an important aspect of the candidate substance screening assay in that, in some cases, a relatively purified preparation is required to distinguish between stress protector protein inhibition, as opposed to indirect inhibition of other substances in the extract which then might affect the stress protein. In any event, the successful isolation of the stress protector protein now allows for the first time the ability to identify new compounds which can be used for inhibition screening.

The candidate screening assay is quite simple to set up and perform, and is related in many ways to the assay discussed above for determining stress protein activity. Thus, after obtaining a relatively purified preparation of the stress protector protein, one will desire to simply admix a candidate substance such as nucleotide analog with the stress protein preparation, preferably under conditions which would allow the stress protein to perform its protective functions but for the inclusion of an inhibitory substance.

Accordingly, one will desire to measure or otherwise determine the activity of the relatively purified stress protector protein in the absence of the assayed candidate substance relative to the activity in the presence of the candidate substance in order to assess the relative inhibitory capability of the candidate substance. For example, one might measure its ability to protect an enzyme activity at high temperatures.

In still further embodiments, the present invention is concerned with a method of inhibiting a stress protector protein which includes subjecting the stress protein to an effective concentration of a stress protector protein inhibitor such as one of the family of peptidyl compounds discussed above, or with a candidate substance identified in accordance with the candidate screening assay embodiments. This is, of course, an important aspect of the invention in that it is believed that by inhibiting the stress protein, the cell will become susceptible to stress.

The second assay for inhibitory substances of heat shock protein function is an in vivo assay. For example, mutations in the HSP104 gene can be produced by treating the gene with a mutagen in vitro. The genes are then transformed back into yeast cells under the control of an inducible promoter such as the galactose inducible promoter gal 1. Cells are then plated onto glucose and then replica plated onto galactose. Cells which live on glucose but die on galactose harbor mutations which have a dominant negative effect on the function of the hsp104 protein. That is the mutated version of the hsp104 protein inhibits the wild-type protein by, for example, forming mixed, non-functional multimeric complexes with the wild-type protein or by competing with it for targets of function. This method is by no means limited to mutated versions of the hsp104 gene but comprises over-expressed or mutated target proteins, over-expressed or mutated cofactors, and proteins which can specifically bind the stress protein, its gene, or its messenger RNA.

EXAMPLE 15
Use of hsp100 Mutations to Improve Pasteurization of Beer

A yeast disclosed herein, *S. cerevisiae* is a derivative of a brewer's yeast. To improve methods for pasteurization of beer, preferred brewers strains of yeast have HSP104 mutations introduced into their genomes e.g., by site specific mutagenesis. These mutant strains are employed to seed fermentation vats instead of the routine isogenic wild-type strains. Because the HSP104 mutation does not interfere with the ability of yeast to grow at normal temperatures, nor to tolerate and produce concentrations of ethanol routinely encountered or required in beer processing, the mutant strains should not deleteriously affect beer production. The strains, however, are much more sensitive to heat. Therefore, pasteurization after the beer is formed may be performed at temperatures that are several degrees below that of the normal process, for example, at 45° C. instead of 55° C. and for a shorter period of time. This improves the quality of the beer by not subjecting it to temperatures that adversely affect quality. This method should be generally applicable to any process in which deliberately introduced strains of microorganisms are employed. The method comprises the production of foods and beverages as well as commercial processes such as metal scavenging and waste treatment.

EXAMPLE 16
Use of Methods and Compositions of the Present Invention to Facilitate Survival of Plants at High Temperatures For the production of plants with increased thermotolerance, the yeast HSP104 gene, or a functionally equivalent plant homolog is placed under the control of the $^{35}$S cauliflower mosaic virus promoter or another inducible or constitutive promoter that is active in plant cells, to form a genetic construct. Functionally equivalent plant homologues into plant comprise nucleic acid segments having at least one nucleotide binding site and at least 25% homology with sequences shown in FIG. 1A, FIG. 1B, FIG. 1C, and FIG. 1D. Several methods of transformation may be employed to introduce the genetic construct into a plant cell. For plants that are relatively easy to transform, for example, tobacco, brassica (cannola oil production), potatoes, tomatoes, and the like, the HSP104 gene can be inserted into an agrobacteria vector which is employed for a standard transformation procedure into a host plant cell.

For corn, rice and other species generally more difficult to transform, a particle accelerator gun is the currently preferred method for transformation. For this method, solutions of HSP104 DNA are coated onto tungsten pellets and embryonic or pollen tissue are bombarded. The successful transformations may be selected by co-expression of a selectable gene included in the DNA used for transformation.

It is contemplated that additional copies of the wild-type plant gene or a functional equivalent from another organism will increase the ability of plants to tolerate heat, desiccation, and other stresses. In some cases, tolerance might be achieved with smaller modules of the protein. These might even be assembled separately and brought together only in the final composition. For example, the two nucleotide binding domains which contribute to hsp100 function may be brought into the cells on separate vectors and the proteins themselves may directly co-assemble into a functional unit. It is also envisioned that the coding sequences for the stress protective protein may be placed under a variety of other regulatory systems so that they would be expressed only at particular times in development or in particular cells or tissues.

EXAMPLE 17
The HSP100 Protein Prevents Accumulation of Aggregated Cellular Components In Vitro The ability of the hsp104 protein to prevent the accumulation of aggregated cellular components in vivo will be of benefit in the production of valuable proteins in vitro in heterologous systems. A common problem with such production is the aggregation of the products in the cell. For example growth factors, enzymes, and structural proteins produced in *E. coli* often form massive aggregates called inclusion bodies. Such aggregates form in both bacterial and eukaryotic expression systems and, as methods for the production of such proteins in cell-free systems are developed, it is expected that aggregation of the components will be a major limitation. Expressing hsp100 or a functional equivalent thereof, during or after the synthesis of these constituents will help prevent the formation of aggregates of proteins or help to resolve them into functional species once they have formed.

EXAMPLE 18
Stress Protector Proteins as Chaperones

Other heat shock proteins have been shown to be capable of providing their chaperoning functions in vitro in both complex and simple biological systems. For example, hsp70 family members can promote the transport of other proteins into mitochondria or across biological membranes (see Lindquist and Craig, 1988 for review). Hsp70 family members can also protect core RNA polymerase from denaturation by heat (Skonra et al., 1990). The family of hsp100 protein apparently is specialized to provide protection under more stressful conditions than is the hsp70 proteins. Indeed, overexpression of the hsp70 protein provides only a transient partial compensation for loss of hsp100 protein in the hsp104 mutation. Thus, including a member of the hsp100 family in a reaction involving biological components in vitro is a powerful method for protecting them from inactivation. Inactivation might occur at random over time due to random protein denaturation or might occur in particular components of the system exposed to stress such as heat, alcohol, or heavy metal ions. The inclusion of hsp100 proteins or fragments thereof also aids in preserving biological functions during long term storage of biological components. The stress protective protein could be added to the system directly in purified or partially purified form. Alternatively, components for assembling the protein in vitro could be added to the system. The system could be used to protect processes such as in vitro photosynthesis, in vitro manufactures of metabolites, the processing and detoxifications of noxious agents, enzymatic catalysis and proteinaceous assembly.

EXAMPLE 19
Reduction in Acquired Thermotolerance Due to Antisense Mutations in hsp70

It was apparent that the antisense line acquired thermotolerance more slowly than wild-type cells and that the extracopy line hsp70 acquired thermotolerance more rapidly than wild-type cells. For example, in comparing cells that had been given an 11 minute pretreatment prior to the severe heat shock, the wild-type line had reached 40% of confluent cell density by day five, the antisense line 22%, and the extra-copy line 84%. For easier comparison of the different cell lines, cell densities on day 5 (normalized to maximal densities for that cell line) are plotted on the composite graph in panel D (FIG. 18A, FIG. 18B, FIG. 18C and FIG. 18D). Here it is clear that the extra-copy line achieved a maximum protective effect from the pretreatment with 11 minutes. The antisense cells achieved maximum protection only after a 30 minute pretreatment. The wild-type cells achieved maximum protection after 20 minutes.

TABLE 1

Growth in Respiratory Media

|  | HSP104 | Δhsp104 |
|---|---|---|
| Log Phase Duplication times (hours) | | |
| YPAc | 2.8 | 2.3 |
| SAc | 4.1 | 3.7 |
| Stationary Plateau Densities (cells/ml) | | |
| YPAc | $1.4 \times 10^8$ | $1.9 \times 10^8$ |
| SAc | $6.8 \times 10^7$ | $9.2 \times 10^7$ |

TABLE 2

Long-Term Viability

|  | HSP104 | Δhsp104 |
|---|---|---|
| Stationary Phase Viability at 25° C. | | |
| 3 days | $5.88 \times 10^7$ | $5.90 \times 10^7$ |
| 20 days | $4.85 \times 10^7$ | $3.57 \times 10^7$ |
| 55 days | $1.80 \times 10^4$ | $1.50 \times 10^3$ |
| 66 days | $1.60 \times 10^3$ | $1.00 \times 10^2$ |
| Spores Viability at 4° C. | | |
| 1 day | $1.21 \times 10^8$ | $1.27 \times 10^8$ |
| 6 months | $1.25 \times 10^8$ | $0.35 \times 10^8$ |

MATERIALS AND METHODS

1. A Method for Yeast Culture Conditions

Unless otherwise indicated, yeast liquid cultures were grown aerobically in a New Brunswick Psycrotherm incubated shaker at 25° C. and 200 rpm. Cultures were always grown with a minimum air-to-culture volume ration of 5 to 1.

Rich medium (YPDA: 1% yeast extract, 2% Bactopeptone, 2% dextrose) and minimal medium (SD: 0.68% yeast nitrogen base without amino acids, 2% dextrose, 1% phthalic acid, Ph 5.5, supplemented with appropriate amino acids) were prepared as described (Sherman et al., 1986). Acetate-based rich (YPAc) and minimal (SAC) media were prepared by replacing the dextrose with 1% Potassium acetate. Glycerol-based medium was prepared by replacing the dextrose with 3% glycerol. Agar plates were prepared by adding 1.8% agar prior to autoclaving. Drop-out (omission) plates and sporulation plates (SPIII-22) were prepared as described (Klapholz and Esposito, 1982).

When log-phase cultures were desired, overnight stationary-phase cultures, in YPDA, were used to inoculate media, according to the formula:

$$\frac{\text{(desired cell density, cell/ml)} \times \text{(culture volume, ml)}}{2^{(incubation\ time,\ hrs)/(doubling\ time,\ hrs\ per\ doubling)}}$$

To circumvent day-to-day variations in growth rate, cultures were routinely inoculated at ½, 1, and 2 times the calculated density. At the time of the experiment, the culture which was nearest the desired density was used. Because heat shock proteins are induced a few generations prior to stationary-phase, and heat shock proteins are long lived, it is preferred that cultures go through several doublings prior to their use in log phase. Cultures which had overgrown were never simply diluted to the desired density. Rather, when necessary, they were diluted back and allowed to go through at least 2 doublings prior to use.

2. A Method for Yeast Transformations

Yeast were transformed using the lithium salt method (Ito et al. 1983). Cells were grown aerobically to mid-log phase ($1-2\times10^7$ cells/ml) in liquid YPDA medium. Cells were harvested by centrifugation, washed and resuspended in 100 mM lithium acetate to a final concentration of $1-2\times10^8$ cell/ml and incubated at room temperature for 2–4 hours with gentle shaking. Cells were pelleted by centrifugation and resuspended at $2-4\times10^9$ cell/ml in 100 mM lithium acetate. 15 μl, containing 1–5 μg CsCl purified DNA and 5 μl each, 10 μg/ml dextran sulfate, 10 μg/ml BSA was added to 50 μl aliquots of the cell suspension and incubated at room temperature for 30 minutes. Polyethylene glycol, 0.5 ml of 40%, was then added to each sample and incubation was continued for an additional 30 minutes at room temp. The cells were briefly spun down, heated at 42° C. for 5 minutes, and spun down again. The cells were washed with 1 ml sterile water, resuspended in 100 μl water, and plated on an appropriate selective plate. Colony formation generally required 3 to 5 days at 30° C.

3. Methods of Preparing the Proteins of the Present Invention

Recombinant vectors are useful both as a means for preparing quantities of the stress proteins, or as a means for preparing the encoded proteins. It is contemplated that where proteins of the invention are made from recombinant means, one may employ either prokaryotic or eukaryotic expression systems.

Where expression of nucleic acid segments in a eukaryotic host is contemplated, it may be desirable to employ a vector, such as a plasmid, that incorporates a eukaryotic origin of replication, as exemplified by vectors of the pCMV series, like pCMV4. Additionally, for the purposes of expression in eukaryotic systems, one will desire to position the stress protein encoding sequence adjacent to and under control of an effective eukaryotic promoter, such as an SV40 or CMV promoter. To bring a coding sequence under the control of a promoter, whether it be a eukaryotic or prokaryotic promoter, all that is generally needed is to position the 5' end of the transcription initiation site of the transcriptional reading frame of the protein between about 1 and about 50 nucleotides downstream of the promoter chosen.

Furthermore, where eukaryotic expression is contemplated, one will desire to incorporate into the transcriptional unit which includes the desired peptide or protein, an appropriate translation initiation site and polyadenylation site (e.g., 5'-AATAAA-3'). Typically, the poly A site is placed about 30 to 2000 nucleotides "downstream" of the termination site of the protein at a position prior to transcription termination.

Prokaryotic expression is an alternative which can be employed where desired. Although not required, where prokaryotic expression is envisioned, one will generally desire to employ a transcriptional unit which incorporates a reading frame corresponding only to the desired peptide itself, represented by embodiments in FIG. 1A, FIG. 1B, FIG. 1C, FIG. 1D and FIG. 1E, so that further processing will not be required. Typically, prokaryotic promoters which may be employed include $P_L$, T7 and lac promoter. Other preferred bacterial expression vectors include plasmid PKK233-2 and PKK233-3, available from Pharmacia LKB Technology. These utilize the tac and trc promoters, respectively.

Of course, even where a eukaryotic hook-up and expression is used, one will sometimes desire to include a prokaryotic origin of expression, as well as selective markers operable in prokaryotic systems, to allow "shuttling" of sequences from construction in prokaryotic to expression in eukaryotes.

In certain embodiments, one may desire to simply prepare stress proteins or fragments of proteins in accordance with the present invention by non-recombinant synthetic means, such as by chemical synthesis of peptides or cell-free ribosomal "machines." Suitable peptide synthesizers are also commercially available (Applied Biosystems), and may be employed.

In certain embodiments of the invention it is contemplated that DNA fragments both shorter and longer which incorporate sequences from FIG. 1A, FIG. 1B, FIG. 1C and FIG. 1D will find additional utilities, including uses in the preparation of short active peptides or even as short DNA fragment hybridization probes, e.g., in screening clone banks. In any event, fragments corresponding to the FIG. 1A, FIG. 1B, FIG. 1C and FIG. 1D sequence for stretches of as short as 14–20 or so nucleotides, will find utility in accordance with these or other embodiments. By having stretches of at least about 14 nucleotides in common with the nucleic acid segments of FIG. 1A, FIG. 1B, FIG. 1C and FIG. 1D, or their complements, a DNA segment will have the ability to form a preferential hybrid with stress protein DNA, particularly under more stringent conditions such as 0.15M NaCl and 0.02M sodium citrate PH 7.4 at 50° C. While a complementary or common stretch of about 14 or so nucleotides will ensure the ability to form a stable hybrid, longer stretches of complementarily may prove more desirable for certain uses. Thus, one may desire for certain uses DNA segments incorporating longer stretches of complementarily, for example, on the order of 18, 22 or even 25 or so bases.

4. Antibodies Against the Proteins of the Present Invention

In other embodiments, the invention concerns the preparation of antibodies to the stress protein and species derived therefrom, either recombinant or non-recombinantly prepared. For example, it is contemplated that antibodies prepared against the proteins of FIG. 1A, FIG. 1B, FIG. 1C, FIG. 1D and FIG. 1E, or other non-human species such as bovine or porcine, will have certain advantages over antibodies prepared against the human species, particularly in embodiments where an immuno-binding of reduced strength is desired.

Compositions which include monoclonal antibodies of the present invention may be prepared by first fusing spleen cells of a rodent with myeloma cells from the same rodent species, wherein the rodent providing the spleen cells has been immunized with the stress protein, precursor, or related peptides. The rodent species utilized will generally be a mouse, particularly where one seeks to make an antibody against the protein of FIG. 1A, FIG. 1B, FIG. 1C, FIG. 1D and FIG. 1E. Of course, where a protein is prepared which incorporates structural variations over the one will likely be able to successfully employ a hybridoma system according to the species of interest.

In addition, the present invention provides a method for isolating stress proteins from other species which may be found antigenically cross-reactive with that of yeast. This method includes preparing an immunoadsorbent material having attached thereto an antibody to the protein. Numerous immunoadsorbent materials are known to those skilled in the art and include, for example, Affi-Gel, Cn-Sepharose, protein A=Sepharose, and numerous other well known immunoadsorbent techniques. All such techniques are applicable to the present invention and should prove useful in the isolation of the immuno cross-reactive species (for a more complete listing, see *Monoclonal Hybridoma Antibodies: Techniques and Applications*, John G. Hurrell, ed., CRC Press, 1982, incorporated herein by reference).

Moreover, kits may be provided in accordance with the present invention to allow for a detection of the stress protein in a biologic sample. Such kits would include polyclonal or monoclonal antibodies having specificity for the stress proteins or immunologically related protein, in combination with an immunodetection reagent. An immunodetection reagent is defined as any reagent for detecting or quantifying the formation of antibody/antigen complexes. Typical immunodetection reagents include the use of radiolabelled or enzyme-labeled antigens or antibodies. Techniques which incorporate labeled antibodies include, for example, RIA (radioimmunoassay) and ELISA (enzyme-linked immuno assay). However, numerous other techniques are known which may be employed in immunodetection kits in accordance with the present invention. Patents which teach suitable techniques include, for example, U.S. Pat. Nos. 4,446,232; 4,407,943; 4,399,299; and 454,233.

Neutralizing antibodies are also contemplated which, when bound to the protein or a segment thereof, render the proteolytic capability of the protease non-functional.

5. Host Cell Cultures and Vectors

In general, prokaryotes are preferred for the initial cloning of DNA sequences and constructing the vectors useful in the invention. For example, *E. coli* K12 strain 294 (ATCC No. 314460) is particularly useful. Other microbial strains which may be used include *E. coli* strains such as *E. coli* B, and *E. coli* X 1776 (ATTC No. 31537). These examples are, intended to be illustrative rather than limiting.

Prokaryotes may also be used for expression. The aforementioned strains, as well as *E. coli* W3110 (F-, lambda-, prototrophic, ATCC No. 273325), bacilli such as *Bacillus subtilus*, or other enterbacteriacea such as *Salmonella typhimurium* or *Serratia marcesans*, and various Pseudomonas species may be used.

In general, plasmid vectors containing replicon and control sequences which are derived from species compatible with the host cell are used in connection with these hosts. The vector ordinarily carries a replication site, as well as marking sequences which are capable of providing phenotypic selection in transformed cells. For example, *E. coli* is typically transformed using PBR322, a plasmid derived from an *E. coli* species pBR 322 contains genes for ampicillin and tetracycline resistance and thus provides easy means for identifying transformed cells. The PBR plasmid, or other microbial plasmid or phage must also contain, or be modified to contain, promoters which can be used by the microbial organism for expression of its own proteins.

The promoters most commonly used in recombinant DNA construction include the B-lactamase (penicillinase) and lactose promoter systems and a tryptophan (trp) promoter system. While these are the most commonly used, other microbial promoters have been discovered and utilized, and details concerning their nucleotide sequences have been published, enabling a skilled worker to ligate them functionally with plasmid vectors.

In addition to prokaryotes, eukaryotic microbes, such as yeast cultures may also be used. *Saccharomyces cerevisiae*, or common baker's yeast is the most commonly used among eukaryotic microorganisms, although a number of other strains are commonly available. For expression in Saccharomyces, the plasmid Yrp7, for example, is commonly used. This plasmid already contains the trpl gene which provides a selection marker for a mutant strain of yeast lacking the ability to grow in tryptophan, for example ATCC No. 44076 or PEP4-1. The presence of the trpl lesion as a characteristic of the yeast host cell genome then provides an effective environment for detecting transformation by growth in the absence of tryptophan.

Suitable promoting sequences in yeast vectors include the promoters for 3-phosphoglycerate kinase or other glycolytic enzymes, such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. In constructing suitable expression plasmids, the termination sequences associated with these genes are also ligated into the expression vector 3' of the sequence desired to be expressed to provide polyadenylation of the mRNA termination. Other promoters, which have the additional advantage of transcription controlled by growth conditions are the promoter region for alcohol dehydrogenase 2, isocytochrome C, acid phosphatase, degradative enzymes associated with nitrogen metabolism, and the aforementioned glyceraldehyde-3-phosphate dehydrogenase, and enzymes responsible for maltose and galactose utilization. Any plasmid vector containing a yeast-compatible promoter, origin of replication and termination sequences is suitable.

In addition to microorganisms, cultures of cells derived from multicellular organisms may also be used as hosts. In principle, any such cell culture is workable, whether from vertebrate or invertebrate culture. However, interest has been greatest in vertebrate cells, and propagation of vertebrate cells in culture (tissue culture) has become a routine procedure in recent years. Examples of such useful host cell lines are AtT-20 VERO and HeLa cells, Chinese hamster ovary (CHO) cell lines, and W138, BHK, COS-7 293 and MDCK cell lines. Expression vectors for such cells ordinarily include (if necessary) an origin of replication, a promoter located in front of the gene to be expressed, along with any necessary ribosome binding sites, RNA splice sites, polyadenylation site, and transcriptional terminator sequences.

For use in mammalian cells, the control functions on the expression vectors are often provided by viral material. For example, commonly used promoters are derived from polyoma, Adenovirus 2, Cytomegalovirus and most frequently Simian Virus 40 (SV40). The early and late promoters of SV40 virus are particularly useful because both are obtained easily from the virus as a fragment which also contains the SV40 viral origin of replication. Smaller or larger SV40 fragments may also be used, provided there is included the approximately 250 bp sequence extending from the Hind III site toward the Bgl site located in the viral origin of replication. Further, it is also possible, and often desirable, to utilize promoter or control sequences normally associated with the desired gene sequence, provided such control sequences are compatible with the host cell systems.

An origin of replication may be provided either by construction of the vector to include an exogenous origin, such as may be derived from SV40 or other viral (e.g., Polyoma, Adeno, HSV, BPV, CMV source, or may be provided by the host cell chromosomal replication mechanism. If the vector is integrated into the host cell chromosome, the latter is often sufficient.

6. Nucleic Acid Hybridization to Detect the sequences Capable of Coding for the Stress Response Proteins or their Biologically Functional Equivalents The nucleic acid sequence information provided by the invention allows for the preparation of relatively short DNA (or RNA) sequences having the ability to specifically hybridize to gene sequences capable of coding for at least the protective domain of the stress proteins. In these aspects, nucleic acid probes of an appropriate length are prepared based on a consideration of the sequence shown in FIG. 1A, FIG. 1B, FIG. 1C, FIG. 1D and FIG. 1E. The ability of such nucleic acid probes to specifically hybridize to the stress proteins lend them particular utility in a variety of embodiments. Most importantly, the probes can be used in a variety of assays for detecting the presence of complementary sequences in a given sample. Other uses are envisioned, including the use of the sequence information for the preparation of mutant species primers, or primers for use in preparing other genetic constructions.

To provide certain of the advantages in accordance with the invention, the preferred nucleic acid sequence employed for hybridization studies or assays includes sequences that are complementary to at least a 14 base nucleotide stretches of the sequence shown in FIG. 1A, FIG. 1B, FIG. 1C and FIG. 1D. A size of at least 14 nucleotides in length helps to ensure that the fragment will be of sufficient length to form a duplex molecule that is both stable and selective. Such fragments may be readily prepared by, for example, directly synthesizing the fragment by chemical means, by application of nucleic acid reproduction technology, such as the PCR technology of U.S. Pat. No. 4,603,102, or by introducing selected sequences into recombinant vectors for recombinant production. Segments of from 18 to 25, or even 30 to 40 bases are also within the scope of this invention.

Accordingly, the nucleotide sequences of the invention are important for their ability to selectively form duplex molecules with complementary stretches of the gene. Depending on the application envisioned, varying conditions of hybridization may be employed to achieve varying degree of selectivity of the probe toward the target sequence. For applications requiring a high degree of selectivity, relatively stringent conditions may be employed to form the hybrids, for example, selecting relatively low salt and/or high temperature conditions, such as provided by 0.02M–0.15M NaCl at temperatures of 50° C. to 70° C. These conditions are particularly selective, and tolerate little, if any, mismatch between the probe and the template or target strand.

Of course, for some applications, for example, preparation of mutants employing a mutant primer strand hybridized to an underlying template, or to isolate stress protein sequences from related species, functional equivalents, or the like, less stringent hybridization conditions are called for in order to allow formation of the heteroduplex. In these circumstances, conditions employed would be, e.g., such as 0.15M–0.9M salt, at temperatures ranging from 20° C. to 55° C. Cross-hybridizing species can thereby be readily identified as positively hybridizing signals with respect to control hybridizations. In any case, it is generally appreciated that conditions can be rendered more stringent by the addition of increasing amounts of formamide, which serves to destabilize the hybrid duplex in the same manner as increased temperature. Thus, hybridization conditions can be readily manipulated, and thus will generally be a method of choice depending on the desired results.

In certain embodiments, it will be advantageous to employ nucleic acid sequences of the present invention in combination with an appropriate means, such as a label, for determining hybridization. A wide variety of appropriate indicator means are known in the art, including radioactive, enzymatic or other ligands, such as avidin/biotin, which are capable of giving a detectable signal. In preferred diagnostic embodiments, an enzyme tag such as urease, alkaline phosphatase or peroxidase, may be employed instead of radioactive or other environmental undesirable reagents. In the case of enzyme tags, colorimetric indicator substrates are known which can be employed to provide a means visible to the human eye or spectrophotometrically, to identify specific hybridization with complementary nucleic acid-containing samples.

In general, it is envisioned that the hybridization probes described herein will be useful both as reagents in solution hybridization as well as in embodiments employing a solid phase. In embodiments involving a solid phase, the test DNA (or RNA) is adsorbed or otherwise affixed to a selected matrix or surface. This fixed, single-stranded nucleic acid is then subjected to specific hybridization with selected probes under desired conditions. The selected conditions will depend on the particular circumstances based on the particular criteria required (depending, for example, on the G+C contents, type of target nucleic acid, source of nucleic acid, size of hybridization probe, etc.). Following washing of the hybridized surface so as to remove nonspecifically bound probe molecules, specific hybridization is detected, or even quantified, by means of the label.

One method of making molecules for detection of cell extracts is to use fluorescent probes. Fluorescent probes are well known to those skilled in the art. An example of a method is to bind fluorescein-labeled avidin (Vector Laboratories, Burlingame, Calif.) to a biotin-labeled protein. The signal may be enhanced.

7. Using a Frame Shift Mutation to Produce a Dominant-Negative Effect on Thermotolerance An approach which was employed to examine the function of hsp70 was to transform cells with mutated versions of the Hsp70 gene. Becauses hsp70 is believed to function by interaction with other proteins, a substantial alteration in the structure of the protein would, in some cases, be expected to have a dominant-negative effect on the function of the wild-type protein (Herskowitz, 1987). Three mutations were examined: Mutations 110 and 402 are overlapping deletions in the amino-terminal portion of the protein, with the 110 mutation deleting codons 114 to 337 and the 402 mutation deleting codons 6 to 337. Mutation 300fs is a frame shift at codon 337 resulting in the premature termination of translation shortly thereafter.

The mutated genes were transformed into cells at different copy numbers and transformants that synthesized the mutant proteins at a slightly higher rate than the endogenous wild-type protein were chosen for further analysis. Proteins produced by the amino-terminal deletions were also shown to accumulate to a slightly higher level than the endogenous hsp70 protein by Western blot analysis. Accumulation was not tested for the frame-shift mutation because it did not react with available antibodies, but labelling experiments suggest it is stable.

Figure 19:
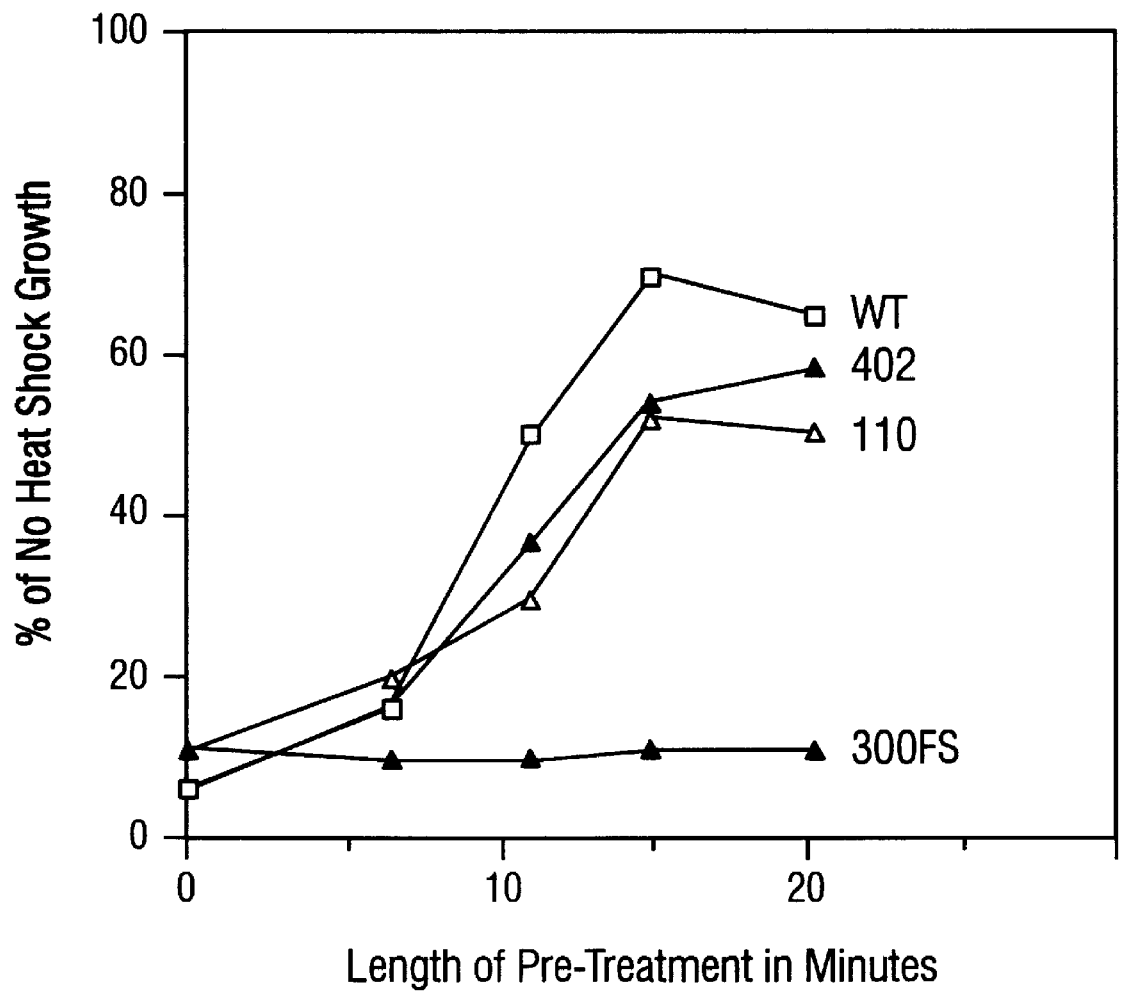
FIG. 19. Thermotolerance tests on mutants of HSP70.

FIG. 19 shows the results of thermotolerance tests on such cells. In this composite graph, cell densities on day 5 are plotted against the length of the 35° C. pretreatment. Neither of the deletions in the amino-terminal domain had a substantial effect on thermotolerance. The 300fs mutation, however, drastically inhibited the acquisition of thermotolerance.

It is possible that the loss of thermotolerance in cells transformed with the 300fs mutation is an indirect effect, due to an alteration in the genome produced by the insertion of the transforming plasmid. Since the lines employed in these experiments are polyclonal and should contain a mixture of insertion sites, this seems unlikely. However, to insure that the thermotolerance effect was due to the production of the 300fs protein and not to any peculiarity of the transformation, additional transformants were established. Even in transformants that carried fewer copies of the gene and expressed the 300fs construct a lower rates, the development of thermotolerance was very severely impaired. It was concluded that expression of the 300fs mutation has a dominant-negative effect on thermotolerance.

8. A Method for Construction of HSP104 Deletion Strains

Strains 747Δ104 and 27βΔ104 were constructed by one-step gene replacement (Rothstein, 1983). Plasmid pYS-U2 was provided by Yolanda Sanchez. It contains the HSP104 coding region, upstream regulatory sequences, and an upstream open reading frame. The ≈1.2 kb ApaI/BglII fragment of pYS104 (Sanchez and Lindquist, 1990) is replaced by a ≈1.6 kb HindIII fragment containing the URA3 gene. This removes ≈200 bp of upstream untranslated sequences and ≈750 bp of coding region. Although the remaining coding region (≈8 kb) is potentially capable of encoding the ≈64 kd carboxy terminus of the protein, this fragment has not been detected.

The plasmid was digested with ClaI and HindIII endonucleases, following manufacturers' recommendations. The digested plasmid was electrophoresed through 1% agarose dissolved in 1× TAE buffer. The ≈2.20 kb fragment, containing the URA disrupted HSP104 gene, was excised from the gel and frozen at −20° C. for 30 minutes. The gel slice was then thawed at 37° C., macerated, and transferred to a Millipore Ultrafree-MC microcentrifugal filtration unit (0.45 μm pore) and spun in a microcentrifuge for 5 minutes. The gel fragments were resuspended in $^{200}$ μl TE (10 mM Tris, 1 mM EDTA, pH 8.0) and respun. The filtrate was extracted with phenol and chloroform and then precipitated in 0.3M sodium acetate, 70% ethanol at −20° C. Strains DBY 747 W303A, W303B and K396-27B were transformed, as described above, with 10 μg of the isolated DNA fragment containing the URA3-disrupted HSP104 gene. As a control, these strains were also transformed with a URA3 DNA fragment, isolated from plasmid YCp50. URA$^+$ transformants were screened for the lack of HSP104 synthesis by pulse labelling with $^3$H-Isoleucine at 37° C. and separation of labelled proteins on 8% SDS-PAGE gels.

In order to create an HSP104 disruption in another low-thermotolerant background, strains 4053-1-4 and 4053-3-4 were also transformed as described. URA$^+$ transformants were only rarely obtained, and did not contain the HSP104 disruption. In previous experiments, the 4053 strains were seen to transform poorly (Rosenberg, unpublished observations). Thus, HSP104 disruptions could not be obtained by transformation. In order to get the HSP104 disruption into the 4053 background, strain 4053-3-4 was crossed to the low-thermotolerant, HSP104 disruption strain, 27βΔ104. The diploid was sporulated, and tetrads were dissected. In each tetrad URA$^+$ and ura segregated 2;2, and protein gels showed that the URA$^+$ strains failed to make a 104 kd heat shock protein (data not shown). One such strain was designated at 3-4Δ104. Normally, this strain would have been backcrossed several times so that the disruption strain would be isogeneic to the parental strain. However, the diploid formed in the cross of 3-4Δ104 and 4053-1-4 sporulated very poorly and did not form 4-spored asci (Rosenberg, unpublished observation). Therefore, backcrosses could not be done.

9. Identification and Use of Stress Protein Inhibitors

If the action of the protein is inhibited, the cell becomes suspectable to stress. This inhibition may be either at the level of transcription, translation, or protein action. Interference with transcription would necessitate interference with mRNA formation on a DNA template. Interference with translation would necessitate interfering with the synthesis of proteins on the mRNA template. Alternatively, the action of the protein may itself be disrupted by destroying the structure of the proteins, in particular its protective domains, by binding the protein to irreversible inhibitors, by obstructing the targets with which it interacts, or by preventing its access to essential cofactors.

Specifically designed peptides which block the function of the proteins are extremely valuable. Methods for identifying suitable protein inhibitors from candidate substances are disclosed herein.

It is an additional object of the present invention to provide a ready means for producing the stress proteins for use in detecting inhibitors, to develop treatment modalities, based on inhibition of the proteins, to develop antibodies for detection of proteins, and to develop inactive mutants of the stress protector genes.

An exemplary embodiment for preparing the proteins is to prepare a nucleic acid segment which includes a nucleic acid sequence capable of encoding the desired protein or polypeptide. This segment may be that which encodes the entire protein or only some portion of it, for example, one of the nucleotide binding domains of the protein. The segment may be as small as that capable of triggering a positive signal with an antibody, thereby, identifying its presence. Segments functionally equivalent to those shown in FIG. 1A, FIG. 1B, FIG. 1C, FIG. 1D and FIG. 1E, which were developed in the present invention, may also be selected depending on the desired polypeptide to be produced. Functional equivalence may be determined by testing whether the segment effects stress protection.

The nucleic acid segment selected is transferred into an environment appropriate for expression of the segment as a polypeptide. This environment may be a vessel containing a mixture capable of inducing expression. Alternatively, the segment may be transferred to a host cell by transformation, microinjection, transfection via a recombinant expression vector, lipofection, electroporation, or a "gene gun." The host cell may be selected from BHK cells, Vero, Hela, *E. coli*, tobacco and the like.

The recombinant expression vector may include a promoter as disclosed herein.

In another embodiment, the nucleic acid segment may be prepared by obtaining genomic nucleic acids from cells, amplifying a conserved nucleic acid sequence region within the genomic nucleic acids, preparing recombinant clones which include said amplifying nucleic acid sequences, and selecting clones which comprise the desired amplified nucleic acid sequence.

The stress proteins may also be prepared by obtaining a sample which contains the protein, homogenizing the sample, and fractionating the homogenate to obtain a stress protein fraction.

10. A Method for Total Yeast DNA Extraction 50 ml cultures were grown to stationary phase in SD lacking uracil. The cells were collected by centrifugation, washed with distilled water, and resuspended in 1.5 ml of 1M Sorbitol, 100 mM EDTA, pH 7.5, 60 $\mu$l of 2.5 mg/ml zymolyase 20,000 (Kirin Brewery, Japan) was added, and the culture was incubated at 37° C. for 1 hr. Cells were spun down and resuspended in 1.5 ml 50 mM Tris, 25 mM EDAT, pH 7.5, 150 $\mu$l 10% SDS was added and the culture was incubated at 65° C. for 1 hr. 600 $\mu$l of 5M potassium acetate, pH 4.5 was added and the culture was incubated on ice for 40 minutes. Cellular debris was pelleted, and the supernatant transferred to a clean tube. Total nucleic acids were precipitated with 0.6 volumes isopropanol, incubated 5 minutes at room temperature. The nucleic acids were pelleted, washed with 70% ethanol, and vacuum dried. After resuspension, the DNA was reprecipitated by adding $\frac{1}{10}$ volume 3M sodium acetate and 2 volumes of ethanol, incubated –20° C. for 30 minutes. The final pellet was typically resuspended on 50 $\mu$l 10 mM tris, 1 mM EDTA, pH 8.0.

11. A Method for Yeast Protein Extraction

Cultures were grown aerobically at 25° C. to an appropriate cell density. $1 \times 10^6$ to $1 \times 10^7$ cells were collected in 10×75 mm pyrex tubes by centrifugation at 3000 rpm for 3 minutes. Cells were resuspended in 200 $\mu$l absolute ethanol containing 2 mM phenylmethyl sulfonyl fluoride and 0.2 g glass beads (0.5 mm diameter) were added. Cells were lysed by vigorous shaking at 4° C. for 4 minutes on a rack vortex mixer. Samples were chilled at –20° C. for 30 minutes in order to precipitate the proteins. Precipitated proteins were collected by centrifugation at 5000 rpm for 5 minutes at 4° C. in a Beckman J-6 centrifuge. The supernatant was removed and the residual ethanol removed by desiccation in a Savant Speed Vac. Protein pellets were resuspended in at least 100 $\mu$l 1× Laemmli sample buffer. In most cases, equal numbers of cells were loaded on each lane of a gel. Strains growing in acetate-based media typically produce smaller cells. For this reason, it was often necessary to load gels by equal protein amounts, rather than equal cell amounts. In this case, protein pellets were resuspended in 1% SDS. Protein concentrations were determined with the BCA system (Pierce) and sample concentrations adjusted accordingly.

12. A Method of Electrophoresis of Proteins

Proteins were separated by SDS-PAGE as described by Laemmli (1970). The separating gel consisted of 7.5% acrylamide in 0.75M Tris-HCl, pH 8.8 and 0.2% SDS. The stacking gel consisted of 3.75% acrylamide in 0.25M Tris-HCl, pH 6.8 and 0.2% SDS. To polymerize the acrylamide solution, 10 mg of ammonium persulfate and 6 $\mu$l TEMED, per 25 ml of gel solution was added. Lyophilized protein samples were dissolved in 1× Laemmli sample buffer (0.083M Tris-HCl, pH 6.8, 2% SDS, 10% glycerol, 5% $\beta$-mercapto ethanol, 0.01% bromophenol blue), vortexed for 10 seconds, and heated at 95° C. for 5 minutes in order to resuspend the proteins. Gel running buffer contained (per liter): 3 g Tris-base, 14.375 g glycine, and 0.5 g SDS. Gels were run at constant wattage and were typically run until the dye front had migrated to the bottom of the gel. Length of the gel varied with the size of the proteins to be maximally separated.

13. A Method for Flurography

To detect $^3$H labelled proteins after electrophoresis, gels were fixed in 7% acetic acid for 3 minutes. The gel was then dehydrated with 3 changes of glacial acetic acid, 2 minutes each. Gels were then soaked in 20% PPO, in glacial acetic acid, for 45 minutes. Gels were then rinsed in deionized water for 15 minutes and then dried under vacuum and exposed to X-ray film at –80° C.

14. A Method for Western Blot Analysis

Following SDS-PAGE, proteins were transferred to Immobilon-P polyvinylidene difluoride microporous membrane (Millipore) by electrophoresis in a Bio-Rad Trans-Blot electroblotting chamber at 100 volts for 1 hour at 4° C. Transfer buffer consisted of 30.2 g Tris-base, 144.2 glycine, 2.5 l methanol per 12.5 l. Transferred proteins were visualized by staining with coomassie brilliant blue (10 g coomassie, 4.5 l methanol, 1 l glacial acetic acid per 10 l) and destaining with 45% methanol, 7% acetic acid.

Protein blots were incubated in 5% non-fat dry mil in 1× PBS for 30 minutes to block non-specific binding of antibodies to the filter. After a brief rinse in PBS the blot was reacted with polyclonal rabbit antiserum, diluted 1;250 for αHSP83 and 1:200 for αHSP104, in 20% serum, 0.02% thimerosal, 1× PBS for 1 hr. Blots were rinsed twice in PBS for 5 minutes each and then reacted with 3 $\mu$Ci $^{125}$I-protein A in 50 ml 5% milk in PBS for 1 hr. Blots were washed once with 50 ml 1× PBS, 5 minutes, and once with 200 ml 1× PBS, 45 minutes. Blots were then exposed to pre-flashed x-ray film with an intensifying screen at −80° C.

15. A Method for In vivo Protein Labelling

Strains were grown to mid-log (1–3×10$^6$ cell/ml) phase in minimal liquid medium (SD or SAc) as described above. 1×10$^6$ cells, in a volume of 100–200 $\mu$l were transferred to 10×75 mm pyrex tubes and labelled with 1.5 $\mu$Ci $^3$H-Leucine or Isoleucine (Amersham, 1 mCi/ml). 1 ml medium (SD-complete or SAc-complete) was added to stop the incorporation of label. The cells were pelleted for 3 minutes at 3000 rpm and the supernatant was removed by aspiration. The proteins were extracted as described above.

16. Thermotolerance Experiments Standard Thermotolerance Assay

In the standard assay, stationary phase cultures were heated at 50° C. for 9 minutes. At stationary phase, thermotolerance is naturally induced, and strain differences in thermotolerance are easily detected. Although similar results can be obtained at log phase, in acetate medium, stationary phase cultures are more convenient to use.

It is preferred that cells be in the same stage of their growth curve to obtain an accurate relative increase of thermotolerance. Cultures were started from single colonies on plates, inoculated into 3 ml YPDA, and grown overnight at 25° C. in order to reach stationary phase. These stationary phase starter cultures were used to inoculate fresh cultures at 1.10$^6$ cell/ml, in 3 ml YPDA. Incubation was at 25° C. with vigorous shaking for 40 to 44 hours. In all cases, cultures reached stationary phase within 24 hours. For haploid strains, this was generally 1–3–10$^8$ cell/ml. Diploid strains typically reach lower densities; 0.8–1.5×10$^8$ cell/ml. At this point in the growth cycle, thermotolerance is maximally induced and stable for several days. The cultures were sonicated at room temperature for 5 seconds, at a setting of 3 (relative output=0.6), using an Artek Sonic Dismembranator model 302 (Dynatech Laboratories) equipped with a microtip (5/32" diameter) in order to disperse cell clumps and separate mature buds from mother cells. 0.3 or 0.4 ml of culture was transferred to a 10×75 mm pyrex tube and heated at 50° C. for 9 minutes in a circulating water bath, without shaking. Tubes were immediately chilled on ice and held until they could be plated (up to 2 hours). 10 fold serial dilutions were made and immediately plated on UPDA, in duplicate. All dilutions were made with room temperature, sterile, glass distilled water. An unheated control sample was similarly plated. After 2 or 3 days at 30° C. plates with 40–300 colonies were counted and the proportion of surviving cells was calculated. Strains DBY 747 and 4053-3-4 were included as high-thermotolerant and low-thermotolerant standards, respectively, in all experiments.

A common variation of this procedure was the killing curve. For stationary-phase killing curves, cultures were prepared as above, but individual tubes containing 0.4 ml were used for each time point. All samples to be heat treated were placed in a 50° C. water bath at the same time. At intervals, a single tube for each culture was removed and placed on ice. Platings were done as above, and the proportion of surviving cells was calculated by comparison to an unheated control sample.

For log-phase killing curves, overnight starter cultures, in YPDA, were used to inoculate cultures, as described. Cultures were grown for at least 4 generations, and used at density of 0.5×10$^7$ cell/ml, for YPDA cultures, or 3–5×10$^6$ cells/ml, for YPAc cultures. Cultures were sonicated, 0.4 ml distributed to tubes, and either heated at 50° C. or first given a pre-heat treatment at 37° C. for 30 minutes and then heated at 50° C. At intervals, a tube was removed and handled as above.

REFERENCES

The references listed below are incorporated herein by reference to the extent that they supplement, explain, provide a background for, or teach methodology, techniques, and/or compositions employed herein.

Reference 1. Andrews, G. K., Harding, M. A., Calvet, J. P. and Adamson, E. D. (1987). The heat shock response in HeLa cells is accompanied by allocated expression of the c-fos proto-oncogene. *Mol. Cell. Biol.* 7, 3452–3458.

Reference 2. Ashburner, M. (1970). Patterns of puffing activity in the salivary gland chromosomes of Drosophila. v. Responses to environmental treatments. *Chromosoma* 31, 356–376.

Reference 3. Borkovich, K. A., Farrelly, F. W., Finkelstein, D. B., Taulien, J., Lindquist, S., HSP82 is an essential protein that is required by cells in higher concentrations for growth at higher temperatures. *Mol Cell Biol* 9, 3919–30 (1989).

Reference. Bourouis, M. and Bruno, J. (1983). Vectors containing a prokaryotic dihydrofolate reductase gene transform Drosophila cells to methotrexate-resistance. *EMBO* 2, 1099–1104.

Reference. Brawerman, G. (1987). Determinants of messenger RNA stability. *Cell* 48, 5–6. Chomyn, Al, Moller, G. and Mitchell, H. K. (1979). Patterns of protein synthesis following heat shock in pupae of Drosophila melanogaster. *Devel. Genet.* 1, 77–95.

Reference 4. Carper, S. W., Duffy, J. J., Gerner, E. W., *Cancer Res* 47, 5249–55 (1987).

Reference 5. Chang, E. C., Kosman, D. J., Willsky, G. R., *J Bacteriol* 171, 6349–52 (1989).

Reference 6. Cheng, M. Y. et al., *Nature* 337, 620–5 (1989).

Reference 7. Chirico, W. J., Waters, M. G., Blobel, G., *Nature* 332, 805–10 (1988).

Reference 8. Craig, et al., (1984). Mutations of the heat inducible 70 kilodalton genes of yeast confer temperature sensitive growth. *Cell* 38: 841–849.

Reference 9. Craig, E. (1985). The heat shock response. *CRC* 181, 239–280.

Reference 10. Deshaies, R. J., Koch, B. D., Werner-Washburne, M., Craig, E. A., Schekman, R., *Nature* 332, 800–5 (1988).

Reference 11. DiDomenico, B. J., Dugaisky, G and Lindquist, S. L. (1982a). Heat shock and recovery are mediated by different translational mechanisms. *Proc. Nat. Acad. Sci. (USA)* 78, 3531–3535.

Reference 12. DiDomenico, B. J., Dugaisky, G and Lindquist, S. L. (1982b). The heat shock response is self-regulated at both the transcriptional and post-transcriptional levels. *Cell* 31, 593–603.

Reference 13. Dourious, M. and Druno, J. (1983). Vectors containing a prokaryotic dihydrofolate reductase gene transform Drosophila cells to methotrexate-resistance. *EMBO* 2, 1099–1104.

Reference 14. Drawerman, G. (1987). Determinants of messenger RNA stability. *Cell* 48, 5–6. Chomyn, Al, Moller, G. and Mitchell, H. K. (1979). Patterns of protein synthesis following heat shock in pupae of *Drosophila melanogaster. Devel. Genet.* 1, 77–95.

Reference 15. Esposito, R. E., Dresser, M., and Breitenbach, M., in *Method Enzymol* 194, 110–131 (1991).

Reference 16. Finley et al. (1987). The yeast polyribiquitin gene is essential for resistance to high temperatures, starvation and other stresses. *Cell* 48: 1035–1046.

Reference 17. Fry, D. C. (1986) ATP-binding site of adenylate kinase: Mchanistic implications of its homology with ras-encoded p21, $F_1$-ATPase, and other nucleotide-binding proteins. PNAS 583: 907–911.

Reference 18. Fry, D. C. (1985) NMR studies of the MgATP binding site of adenylate kinase and of a 45-residue peptide fragment of the enzyme. *Biochem.* 24: 4680–4694.

Reference 19. Gottesman, S. et al. (1989) "The ATP-dependent Clp Protease of *Escerichia coli. J. Biol. Chem.* 265: 7886–7893.

Reference 20. Gottesman, S. (1990) Conservation of the regulatory subunit for the Clp ATP-dependent protease in prokaryotes and eukaryates. PNAS 587: 3513–3517.

Reference 21. Gilmour, D. S. and Lis, J. (1986). RNA polymerase 11 interacts with the promoter region of the noninduced HSP70 gene in *Drosophila melano-gaster* cells. *Mol. Cell Biol.* 6, 3984–2989.

Reference 22. Graves, R. A., Pandey, N. B., Chodchoy, N. and Marzluff, W. F. (1987). Translation is required for regulation of histone mRNA degradation. *Cell* 48, 615–626.

Reference 23. Hall, B. G., *J Bacteriol* 156, 1363–5 (1983).

Reference 24. Hemmingsen, S. M. et al., *Nature* 333, 330–4 (1988).

Reference 25. Hultmark, D., Klemenz, R. and Gehring, W. J. (1986). Translational and transcriptional control elements in the untranslated leader of the heat shock gene hsp22. *Cell* 44, 429–438.

Reference 26. Ingolia, T. D., Craig, E. A. and McCarthy, B. J. (1980). Sequence of three copies of the gene for the major Drosophila heat shock induced protein and their flanking regions. *Cell* 21, 669–679.

Reference 27. Kabnick, K. S. and Housman, D. E. (1988). Determinants that contribute to cytoplasmic stability of human c-fos and B-globin mRNAs are located at several sites in each mRNA *Mol. Cell. Biol.* 8, 3244–3250.

Reference 28. Kang, P. J. et al., *Nature* 348, 137–43 (1990).

Reference 29. Kappeli, O., *Adv. Microb. Physiol* 28, 181–209 (1986).

Reference 30. Katayama, Y. et al (1988). The Two-component, ATP-dependent Clp Protease of *Escherichia coli, J. Biol. Chem.* 295: 18,226–18,334.

Reference 31. Klemenz, R. Hultmark, D. and Gehring, W. J. (1985). Selective translation of heat shock mRNA in *Drosophila melanogaster* depends on sequence information in the leader. *EMBO* 4, 2053–2060.

Reference 32. Kruger, C. and Benecke, B-J. (1981). In vitro translation of Drosophila heat-shock and non-heat-shock mRNAs in heterologous and homologous cell-free systems. *Cell* 23, 595–603.

Reference 33. Kurtz, S., Rossi, J., Petko, L., Lindquist, S., *Science* 231, 1154–7 (1986).

Reference 34. Laemmli, U. K. (1970). Cleavage of structural proteins during the assembly of the head of the bacteriophage T4. *Nature* 227, 680–685.

Reference 35. Lagunas, R., *Yeast* 2, 221–8 (1986).

Reference 36. Lewis, M., Helmsing, P. J. and Ashburner, M. (1975). Parallel changes in puffing activity and patterns of protein synthesis in salivary glands of Drosophila. *Proc. Nat. Acad. Sci. USA* 72, 3604–3608.

Reference 37. Li, G. C., Laszlo, A., in *Changes in Eukaryotic Gene Expression in Resp;onse to Environmental Stress*, Atchison, B. J. and Walden, D. B., Eds. (Academic Press, New York, 1985), p. 227.

Reference 38. Lindquist, S. (1980a). Varying patterns of protein synthesis in Drosophila during heat shock; implications for regulation. *Dev. Biol.* 77, 463–479.

Reference 39. Lindquist, S. (1980b). Translational efficiency of heat induced messages in *Drosophila melanogaster* cells. *J. Mol. Biol.* 137, 151–158.

Reference 40. Lindquist, S. and DiDomenico, B. (1985). Coordinate and noncoordinate gene expression during heat shock: A module for regulation. *Academic Press.*

Reference 41. Lindquist, S. L. (1986). The heat shock response. *Ann. Rev. Biochem.* 55, 1151–1191.

Reference 42. Lindquist, S. and Craig, E. (1988) The heat shock proteins, *Ann Rev Genet* 22: 263–277.

Reference 43. Lindquist, S., Craig, E. A., *Ann Rev Genet* 22, 631–77 (1988); *Stress-Induced Proteins, UCLA Symposium on Molecular and Cellular Biology*, Pardue, M. L., Feramisco, J. R., Lindquist, S. L., Eds (A. R. Liss, Inc., New York, 1988); *Stress Proteins in Biology and Medicine*, Morimoto, R. I., Tissieres, A., Georgopoulos, C., Eds. (Cold Spring Harbor Laboratory Press, New York, 1990); *Heat Shock and Other Stress Response Systems of Plants*, Nover, L., Neumann, D., Scharf, K.-D., Eds. (Springer-Verlag 1989).

Reference 44. McAlister, L., Finkelstein, D. B., Biochem *Biophys Res Commun.* 93, 819–24 (1980).

Reference 45. McGarry, T. (1986). Genetic analysis of heat shock protein synthesis. *Ph.D. Thesis*, University of Chicago.

Reference 46. McGarry, T. and Lindquist, S. (1986). Translational control of heat shock proteins in Drosophila. In *The Translational Control of Protein Synthesis*. Matthews, M.ed. Cold Spring Harbor Press. Cold Spring Harbor, N.Y., pp. 86–90.

Reference 47. McGarry, T. J. and Lindquist, S. L., (1985). The preferential translation of Drosophila hsp70 mRNA requires sequences in the untranslated leader. *Cell* 42 903–911.

Reference 48. McKenzie, S. and Meselsohn, M. (1977). Translation in vitro of Drosophila heat shock messages. *J. Mol. Biol.* 117,279–283.

Reference 49. McKenzie, S. L., Henikoff, S. and Meselsohn, M. (1975). Localization of RNA from heat-induced polusomes at puff sites in *Drosophila melanogaster. Proc. Nat. Acad. Sci. (USA)* 72, 1117–1121.

Reference 50. McMaster, G. K. and Carmichael, G. G. (1977). Analysis of single-and-double-stranded nucleic acids on polyacrylamide and agarose gels by using glyoxal and acridine orange. *Proc. Natl. Acad. Sci. (USA)* 74, 4835–4838.

Reference 51. Parcell, D. et al., manuscript in preparation.

Reference 52. Pelham, H. R., *Cell* 46, 959–61 (1986).

Reference 53. Petersen, R. and Lindquist, S. (1988). The Drosophila hsp70 message is rapidly degraded at normal temperatures and stabilized by heat shock. *Gene* 72, 161–168.

Reference 54. Petko, L., Lindquist, S., (1986) HSP26 is not requjired for growth at high temperatures, nor for thermotolerance spore development or germination. *Cell* 45, 885–94.

Reference 55. Picard, D., et al., *Nature* 348, 166–8 (1990).
Reference 56. Plesset, J., Ludwig, J. R., Cox, B. S., McLaughlin, C. S., *J Bacteriol* 169, 779–84 (1987).
Reference 57. Reading, D. S., Hallberg, R. L., Myers, A. M., *Nature* 337, 655–9.
Reference 58. Riabowol, K. T., Mizzen, L. A., Welch, W. J., *Science* 242, 433–6 (1988).
Reference 59. Rio, D. C. and Rubin, G. M. (1985). Transformation of cultured *Drosophila melanogaster* cells with a dominant selectable marker. *Mol. Cell. Biol.* 5, 1833–1838.
Reference 60. Rothman, J. E., *Cell* 59, 591–601 (1989).
Reference 61. Rothstein, R. J. (1983), One-step gene disruption in yeast *Meth. in Enz.* 101: 202–211.
Reference 62. Rougvie A. E. and Lis, J. T., (1988). The RNA polymerase 11 molecule at the 5' end of the uninduced hsp70 gene of *D. melanogaster* is transcriptionally engaged. *Cell* 54, 795–804.
Reference 63. Sadis, S., Hickey, E. and Weber, L. A. (1988). Effect of heat shock on RNA metabolism in HeLa cells. *J. Cell. Phys.* 135, 377–386.
Reference 64. Sanchez, Y., S. L. Lindquist, *Science* 248, 1112–5 (1990).
Reference 65. Schenberg-Frascino, A. and Moustacchi, E., *Mol. Gen Genet* 115, 243–257 (1972).
Reference 66. Scott, M. P. and Pardue, M. L. (1981). Translational control in lysates of *Drosophila melanogaster* cells. *Proc. Natl. Acad. Sci. USA* 78, 3353–3357.
Reference 67. Shaw, G. and Kamen, R. (1986). A conserved AU sequence from the 3' untranslated region of GM-CSF mRNA mediates selective mRNA degradation. *Cell* 46, 659–667.
Reference 68. Shyy, T.-T., Subjeck, J. R., Heinaman, R., Anderson, G. (1986). Effect of growth state and heat shock on nucelolar localization of the 110,000-Da heat shock protein in mouse embryo fibroblasts. *Cancer Research* 46: 4738–4745.
Reference 69. Simcox, A. A., Cheney, C. M. Hoffman, E. P. and Shearn, A. (1985). A deletion of the 3' end of the *Drosophila melanogaster* HSP70 gene increases stability of mutant mRNA during recovery from heat shock. *Mol. Cell Biol.* 5, 3397–3402.
Reference 70. Skowyra, C., Georgopoulos, M., Zylicz, *Cell* 62, 939–44 (1990).
Reference 71. Storti, r. V., Scott, M. P., Rich, A. and Pardue, M. L. (1980). Translational control of protein synthesis in response to heat shock in *D. melanogaster* cells. *Cell* 22, 825–834.
Reference 72. Subjeck, J. R., Shyy, T., Shen, J., Johnson, R. J. (1983). Association between the mammalian 110,000-dalton heat-shock protein and nucleoi. *J. Cell Biol.* 97: 1389–1395.
Reference 73. Theodorakis, N. G. and Morimoto, R. I. (1987). Posttranscriptional regulation of hsp70 expression in human cells: effects of heat shock, inhibition of protein synthesis, and adenovirus infection on translation and mRNA stability. *Mol. Cell. Biol.* 7, 4357–4368.
Reference 74. Tissieres, A., Mitchell, H. K. and Tracy, U. M. (1974). Protein synthesis in salivary glands of *Drosophila melanogaster:* Relation to chromosome puffs. *J. Mol. Biol.* 84, 389–398.
Reference 75. Velasquez, J. Sonoda, S. Bugaisky, G. E. and Lindquist, S. (1983). Is the major Drosophila heat shock protein present in cells that have not been heat shock? *J. Cell. Biol.* 96, 286–290.
Reference 76. Walker, J. E. (1985). Primary structure and subunit stoichiometry of $F_1$-ATPase from bovine mitochondria. *J. Mol. Biol.* 184: 677–701.
Reference 77. Welch, W. J., Suhan, J. P. (1986). Cellular and biochemical events in mammalian cells during and after recovery from physiological stress. *J. Cell Biol.* 103: 2035–2052.
Reference 78. Werner, W. M., Becker, J., Kosic, S. J., Craig, E. A., *J Bacteriol* 171, 2680–8 (1989).
Reference 79. Widelitz, R. B., Magun, B. E., Gerner, E. W., *Mol Cell Biol* 6, 1088–94 (1986).
Reference 80. Yost, J. G. and Lindquist, S. L. (1986). RNA splicing is interrupted by heat shock and rescued by heat shock protein synthesis. *Cell* 45, 185–193.
Reference 81. Yost, H. J., Lindquist, S., *Mol Cell Biol* 11, 1062–8 (1991).

What is claimed is:

1. A genetic construct comprising:
   (a) a promoter; and
   (b) a structural gene coding for a stress protector protein having the amino acid residue sequence of FIG. 1B (SEQ ID NO:2).

2. The genetic construct of claim 1 wherein the promoter is further defined as an inducible promoter.

3. The genetic construct of claim 2 wherein the inducible promoter is further defined as inducible by an environmental stress factor.

4. The genetic construct of claim 3 wherein the promoter is inducible by heat, cold, ethanol, starvation or desiccation.

5. The genetic construct of claim 4 wherein the promoter is inducible by heat at temperatures at the upper end of an organism's natural growth range.

6. The genetic construct of claim 2 wherein the promoter is further defined as inducible by a hormone or a sugar.

7. The genetic construct of claim 6 wherein the promoter is inducible by glucose or galactose.

8. The genetic construct of claim 1 wherein the promoter comprises a promoter responsive to a first stress and the structural gene encodes an expression product that is responsive to a second stress.

9. An isolated nucleic acid segment, the segment encoding a member of the hsp100 family of stress protector proteins, said member having the amino acid residue sequence of FIG. 1B (SEQ ID NO:2).

10. The nucleic acid segment of claim 9 further defined as a DNA segment.

11. An isolated nucleic acid molecule, the molecule comprising a nucleotide sequence that is identical or complementary to a segment of at least 20 contiguous nucleotide bases of the DNA sequence of FIG. 1A (SEQ ID NO:1).

12. The nucleic acid segment of claim 11 further defined as comprising an approximately 30 nucleotide base long segment.

13. A stress protector protein comprising the amino acid residue sequence of FIG. 1B (SEQ ID NO:2).

14. An antibody that specifically binds the protein of claim 13.

15. The antibody of claim 14 further defined as a monoclonal antibody.

16. A recombinant host cell comprising a genetic construct in accordance with any of claims 1–8.

17. The recombinant host cell of claim 16 wherein the host cell is derived from a human, a bacteria, a yeast, a plant or an insect.

18. The recombinant host cell of claim 17 wherein the bacterial organism comprises *Escherichia coli*.

19. The recombinant host cell of claim 17 wherein the yeast organism comprises Saccharomyces.

20. A method of producing a stress protector protein, the method comprising the steps of:

(a) preparing a genetic construct in accordance with claim 1;

(b) incorporating the construct into a host cell; and (c) expressing the construct in the host cell to produce the protein.

21. A method for preventing or repairing protein denaturation and aggregation in a yeast cell, said method comprising introducing into the yeast cell a stress protector protein of the hsp100 family, said stress protector protein having the amino acid residue sequence of FIG. 1B (SEQ ID NO:2).

22. The method of claim 21 wherein th e stress protector protein is introduced into a yeast cell by means of a nucleotide sequence capable of encoding the stress protector protein, said sequence functionally linked to a promoter capable of regulating expression of said nucleotide sequence in said yeast cell.

23. A method for rendering a yeast cell sensitive to stress, said method comprising interfering with a stress protector protein member of a hsp100 family of the yeast cell, said member having the amino acid residue sequence of FIG. 1B (SEQ ID NO:2).

24. The method of claim 23 wherein the interfering is effected by inducing sufficient mutations in the nucleic acid sequence coding for the stress protector protein to interfere with transcription or to result in encoding of a non-functional stress protector protein.

25. The method of claim 23 wherein the interfering is effected by adding to the yeast cell inhibitors of, or neutralizing antibodies to, said protein.

26. A method for controlling yeast cell's response to stress, said method comprising:

(a) preparing a genetic construct comprising a stress protector gene encoding a member of the hsp100 protein family having the amino acid residue sequence of FIG. 1B (SEQ ID NO:2), said gene capable of being expressed, and a genetic promoter which directs the expression of the stress protector gene; and (b) incorporating the genetic construct into the yeast cell.

27. A genetic construct comprising a structural gene coding for a wide-type eukaryotic hsp100 stress protector protein, said protein recognized by a polyclonal antibody raised against the C-terminal 15 amino acid residues of hsp104, said structural gene encoded by an RNA segment that hybridizes to the DNA sequence of FIG. 1A (SEQ ID NO:1) under conditions including about 0.15M to 0.9M salt at a temperature of about 20° to 55° C.

28. The genetic construct of claim 27, wherein said structural gene comprises at least 14 contiguous nucleotide bases of the nucleic acid sequence of FIG. 1A (SEQ ID NO:1).

29. The genetic construct of claim 28, wherein said structural gene comprises at least 20 contiguous nucleotide bases of the nucleic acid sequence of FIG. 1A (SEQ ID NO:1).

30. The genetic construct of claim 27, further comprising a promoter.

31. The genetic construct of claim 30, wherein said promoter is further defined as an inducible promoter.

32. The genetic construct of claim 31, wherein said inducible promoter is further defined as inducible by an environmental stress factor.

33. A method for preparing a protein comprising expressing in a host cell the genetic construct of claim 27.

* * * * *

UNITED STATES PATENT AND TRADEMARK OFFICE
CERTIFICATE OF CORRECTION

PATENT NO. : 5,827,685

DATED : October 27, 1998

INVENTOR(S) : Susan Lindquist

It is certified that error appears in the above-identified patent and that said Letters Patent is hereby corrected as shown below:

In claim 26, column 60, line 9, after 'controlling', insert --a--.

Signed and Sealed this

Fourth Day of May, 1999

Attest:

Attesting Officer

Q. TODD DICKINSON

Acting Commissioner of Patents and Trademarks